US012765608B2

(12) United States Patent
Gallagher et al.

(10) Patent No.: US 12,765,608 B2
(45) **Date of Patent: *Oct. 20, 2026**

(54) NON-NICOTINE ELECTRONIC VAPING DEVICES HAVING AUTO SHUTDOWN

(71) Applicant: Altria Client Services LLC, Richmond, VA (US)

(72) Inventors: Niall Gallagher, Richmond, VA (US); Terrance Theodore Bache, Richmond, VA (US); Rangaraj S. Sundar, Richmond, VA (US); Jarrett Keen, Richmond, VA (US); Raymond W. Lau, Richmond, VA (US); Eric Hawes, Midlothian, VA (US)

(73) Assignee: Altria Client Services LLC, Richmond, VA (US)

( * ) Notice: Subject to any disclaimer, the term of this patent is extended or adjusted under 35 U.S.C. 154(b) by 516 days.

This patent is subject to a terminal disclaimer.

(21) Appl. No.: 16/929,539

(22) Filed: Jul. 15, 2020

(65) Prior Publication Data

US 2022/0015441 A1 Jan. 20, 2022

(51) Int. Cl.
*A24F 40/53* (2020.01)
*A24F 40/42* (2020.01)
(Continued)

(52) U.S. Cl.
CPC .............. *A24F 40/53* (2020.01); *A24F 40/42* (2020.01); *A24F 40/60* (2020.01); *A61M 15/06* (2013.01);
(Continued)

(58) Field of Classification Search
CPC .......... A24F 40/42; A24F 40/53; A24F 40/60; A61M 2205/52; A61M 2205/3653
See application file for complete search history.

(56) References Cited

U.S. PATENT DOCUMENTS 8,550,129 B2 10/2013 Bonner
9,158,302 B2 10/2015 Thompson
(Continued)

FOREIGN PATENT DOCUMENTS

CN 102396783 A 4/2012
CN 104120308 A 10/2014
(Continued)

OTHER PUBLICATIONS

International Preliminary Report on Patentability dated Jun. 24, 2022 issued in International patent application No. PCT/EP2021/069792.

(Continued)

*Primary Examiner* — Christopher M Rodd
*Assistant Examiner* — Ronnie Kirby Jordan
(74) *Attorney, Agent, or Firm* — Harness, Dickey & Pierce, P.L.C.

(57) ABSTRACT

A non-nicotine pod assembly includes a non-nicotine reservoir to hold non-nicotine pre-vapor formulation, and a heater configured to vaporize non-nicotine pre-vapor formulation drawn from the non-nicotine reservoir. A device body is configured to engage with the non-nicotine pod assembly, and includes a controller. The controller is configured to cause the device body to detect a fault event at the non-nicotine electronic vaping device, classify the fault event as one of a plurality of types of fault events, and perform at least one consequent action based on the classification of the fault event.

11 Claims, 44 Drawing Sheets

(51) Int. Cl.
*A24F 40/60* (2020.01)
*A61M 15/06* (2006.01)

(52) U.S. Cl.
CPC . *A61M 2205/3653* (2013.01); *A61M 2205/52* (2013.01)

(56) References Cited

U.S. PATENT DOCUMENTS

| | | | |
|---|---|---|---|
| 2013/0340775 A1 | 12/2013 | Juster et al. | |
| 2014/0014126 A1 | 1/2014 | Peleg et al. | |
| 2014/0020727 A1* | 1/2014 | Ampolini et al. | A24F 40/50 392/387 |
| 2014/0123990 A1 | 5/2014 | Timmermans | |
| 2014/0230835 A1 | 8/2014 | Saliman | |
| 2014/0251356 A1 | 9/2014 | Xiang | |
| 2014/0270727 A1 | 9/2014 | Ampolini et al. | |
| 2014/0283856 A1 | 9/2014 | Xiang | |
| 2015/0136155 A1 | 5/2015 | Verleur et al. | |
| 2015/0173124 A1 | 6/2015 | Qiu | |
| 2015/0250231 A1 | 9/2015 | Hon | |
| 2015/0305406 A1 | 10/2015 | Li et al. | |
| 2016/0050974 A1* | 2/2016 | Galloway et al. | A24F 40/40 |
| 2016/0057811 A1 | 2/2016 | Alarcon et al. | |
| 2017/0207499 A1* | 7/2017 | Leadley | H01M 10/44 |
| 2017/0245547 A1 | 8/2017 | Lipowicz | |
| 2018/0104214 A1 | 4/2018 | Raichman | |
| 2019/0104764 A1 | 4/2019 | Tucker et al. | |
| 2020/0029619 A1 | 1/2020 | Sundberg et al. | |
| 2020/0046025 A1* | 2/2020 | Otiaba et al. | A24F 40/57 |
| 2022/0015436 A1 | 1/2022 | Gallagher et al. | |

FOREIGN PATENT DOCUMENTS

| | | | |
|---|---|---|---|
| CN | 106231934 | A | 12/2016 |
| CN | 106604654 | A | 4/2017 |
| CN | 110639103 | A | 1/2020 |
| DE | 202012101880 | U1 | 7/2012 |
| EA | 034538 | B1 | 2/2020 |
| EP | 3711502 | A1 | 9/2020 |
| EP | 2563172 | B2 | 5/2022 |
| EP | 3997991 | A1 | 5/2022 |
| JP | 2016-517270 | A | 6/2016 |
| JP | 2017-532011 | A | 11/2017 |
| JP | 2020-505002 | A | 2/2020 |
| JP | 2020-068762 | A | 5/2020 |
| JP | 2020-099353 | A | 7/2020 |
| KR | 20010008162 | A | 2/2001 |
| KR | 20200021461 | A | 2/2020 |
| RU | 2683333 | C1 | 3/2019 |
| WO | 2015/156612 | A1 | 10/2015 |
| WO | WO-2016/020675 | A1 | 2/2016 |
| WO | 2016/150922 | A2 | 9/2016 |
| WO | 2019099539 | A2 | 5/2019 |
| WO | 2020/006311 | A1 | 1/2020 |
| WO | 2020/084757 | A1 | 4/2020 |
| WO | 2020/107394 | A1 | 6/2020 |
| WO | 2020/225541 | A1 | 11/2020 |
| WO | 2021/059377 | A1 | 4/2021 |
| WO | 2021/172715 | A1 | 9/2021 |
| WO | 2021/182730 | A1 | 9/2021 |

OTHER PUBLICATIONS

Charles Garner, et al., "E-Cigarette Task Force-Reference Report—a Brief Description of History, Operation and Regulation," Feb., 2014, Coresta.

S. Madgwick, "An efficient orientation filter for inertial and inertial/magnetic sensor arrays", x-io Technologies Limited, Apr. 2010, http://www.x-io.co.uk/res/doc/madgwick_internal_report.pdf.

Tim Mason, et al., "A practical approach to replicating human puff profiles on a mechanical smoking machine", CORESTA, Milton Keynes, *CORESTA Meeting, Smoke Science/Product Technology, Stratford-upon-Avon*, 2005, SSPT 35, UK.

"Application Guide-Electric Heaters-Power Calculations-calculations for Required Heat Energy", Watlow, 2006 <https://www.watlow.com/reference/files/powercalculations.pdf>, retrieved Jul. 2020.

International Search Report and Written Opinion dated Nov. 11, 2021.

U.S. Office Action for U.S. Appl. No. 16/929,371, dated Mar. 17, 2023.

U.S. Restriction Requirement for U.S. Appl. No. 16/929,371, dated Aug. 12, 2022.

U.S. Restriction Requirement for U.S. Appl. No. 16/929,371, dated Dec. 7, 2022.

International Preliminary Report on Patentability and Written Opinion for PCT Application No. PCT/US2021/037804, dated Jan. 26, 2023.

U.S. Office Action for U.S. Appl. No. 16/929,371, dated Oct. 11, 2023.

U.S. Office Action for U.S. Appl. No. 16/929,371, dated May 15, 2024.

Russian Office Action for Application No. 2023102868, dated Sep. 27, 2024, with English translation.

Russian Notice of Allowance for Application No. 2023102868, dated Nov. 8, 2024.

U.S. Office Action for U.S. Appl. No. 16/929,371, dated Nov. 21, 2024.

Japanese Office Action for Application No. 2023-502687, dated Feb. 25, 2025, with English Translation.

European Office Action issued in Application No. 21742953.9, dated Jun. 2, 2025.

Japanese Office Action for Application No. 2023-501266, dated Apr. 28, 2025, with English Translation.

Japanese Decision to Grant for Application No. 2023-502687, dated Aug. 12, 2025.

Japanese Office Action and English translation thereof for Japanese Application No. 2023-501266 mailed Oct. 27, 2025.

Office Action issued in U.S. Appl. No. 16/929,371 mailed Nov. 7, 2025.

Korean First Preliminary Rejection for Korean Application No. 10-2023-7005281 mailed Jan. 1, 2026.

European Notice of Opposition for Patent No. 4181714, dated Jun. 12, 2025.

U.S. Office Action for U.S. Appl. No. 16/929,371, dated Jul. 1, 2025.

Decision of Refusal issued Feb. 2, 2026 in Japanese Application No. 2023-501266.

Opposition Proceedings Brief Communication issued Jan. 28, 2026 in European Application No. 21743508.0.

First Office Action issued Jan. 28, 2026 in Chinese Applicatin No. 202180048325.5.

First Office Action issued Feb. 10, 2026 in Chinese Applicatin No. 202180053487.8.

Office Action issued Mar. 5, 2026 in Korean Application No. 10-2023-7004728.

Notice of Allowance issued May 7, 2026 in Korean Application No. 10-2023-7005281.

Summons to attend oral proceedings pursuant to Rule 115(a) issued Mar. 19, 2026 in European Application No. 21743508.0.

Final Office Action issued on Jun. 18, 2026 in U.S. Appl. No. 16/929,371.

Rejection Decision issued Jun. 10, 2026 in Chinese Application No. 202180048325.5.

Decision to Grant a Patent issued Aug. 3, 2026 in Japanese Application No. 2023-501266.

Second Office Action issued Aug. 8, 2026 in Chinese Application No. 202180053487.8.

* cited by examiner

NON-NICOTINE ELECTRONIC VAPING DEVICES HAVING AUTO SHUTDOWN

BACKGROUND

Field

One or more example embodiments relate to non-nicotine electronic vaping (non-nicotine e-vaping) devices.

Description of Related Art

Non-nicotine electronic vaping devices (or non-nicotine e-vaping devices) include a heater that vaporizes non-nicotine pre-vapor formulation material to produce non-nicotine vapor. A non-nicotine e-vaping device may include several non-nicotine e-vaping elements including a power source, a non-nicotine cartridge or non-nicotine e-vaping tank including the heater and a non-nicotine reservoir capable of holding the non-nicotine pre-vapor formulation material.

SUMMARY

At least one example embodiment provides a non-nicotine electronic vaping device comprising a non-nicotine pod assembly and a device body. The non-nicotine pod assembly includes a non-nicotine reservoir to hold non-nicotine pre-vapor formulation, and a heater configured to vaporize non-nicotine pre-vapor formulation drawn from the non-nicotine reservoir. The device body is configured to engage with the non-nicotine pod assembly, and includes a controller. The controller is configured to detect a fault event at the non-nicotine electronic vaping device, classify the fault event as one of a plurality of types of fault events, and perform at least one consequent action based on the classification of the fault event.

According to at least some example embodiments, the fault event may be one of a normal event, a soft fault pod event, a hard fault pod event, a soft fault device event, or a hard fault device event. The soft fault pod event and the hard fault pod event may be abnormal conditions at the non-nicotine pod assembly, and the soft fault device event and the hard fault device event may be abnormal conditions at the device body.

The at least one consequent action includes an auto off operation, a heater off operation, a vaping off operation, a charging stop operation, or a combination thereof.

The device body may further include at least one vaper indicator configured to output an indication that the fault event has occurred.

The device body may further include a memory.

The controller may be configured to perform the at least one consequent action by disabling power to the heater, logging an occurrence of the fault event in the memory, and causing the at least one vaper indicator to output the indication that the fault event has occurred.

The controller may be configured to perform the at least one consequent action by disabling a vaping function at the non-nicotine electronic vaping device, logging an occurrence of the fault event in the memory, and causing the at least one vaper indicator to output the indication that the fault event has occurred.

The controller may be configured to detect disengaging of the non-nicotine pod assembly from the device body, and disable the vaping function at the non-nicotine electronic vaping device in response to detecting disengaging of the non-nicotine pod assembly from the device body.

The controller may be configured to cause the device body to enter a sleep mode in response to determining that a corrective action has not occurred in response to the fault event.

The controller may be configured to perform the at least one consequent action by initiating an auto off operation in which the non-nicotine electronic vaping device enters a sleep mode, logging an occurrence of the fault event in the memory, and causing the at least one vaper indicator to output the indication that the fault event has occurred.

The controller may be configured to perform the at least one consequent action by disabling a vaping function, a charging operation, or the vaping function and the charging operation, at the non-nicotine electronic vaping device, logging an occurrence of the fault event in the memory, and causing the at least one vaper indicator to output the indication that the fault event has occurred.

The controller may be configured to initiate a reset timer in response to detecting the fault event, determine that the reset timer has lapsed, and perform a reset of the non-nicotine electronic vaping device in response to determining that the reset timer has lapsed. The reset may be one of a soft reset in which software applications running in the controller are reset, a hard reset in which software applications running on the controller and hardware of the non-nicotine electronic vaping device are reset, or a power on reset (POR). A POR may include generating a reset impulse to the all circuitry of the non-nicotine e-vaping device to clear the fault event.

The controller may be configured to determine that the fault event has been cleared by the reset, and enable the vaping function, the charging operation, or the vaping function and the charging operation, in response to determining that the fault event has been cleared by the reset.

The controller may be configured to detect a corrective action at the non-nicotine electronic vaping device, and enable the vaping function, the charging operation, or the vaping function and the charging operation, in response to detecting the corrective action.

The non-nicotine pod assembly may include a memory configured to store a threshold temperature value, and the controller is configured to detect the fault event by obtaining the threshold temperature value from the memory, estimating a temperature of the heater during operation of the non-nicotine electronic vaping device, and detecting the fault event in response to determining that the temperature of the heater is greater than or equal to the threshold temperature value.

The device body may further include a power supply configured to supply power to the non-nicotine electronic vaping device. The fault event may be a power supply low voltage fault event indicating that a voltage of the power supply is less than a minimum threshold value. The controller may be further configured to perform the at least one consequent action by disabling a vaping function at the non-nicotine electronic vaping device in response to detecting the power supply low voltage fault event.

The device body may further include a power supply configured to supply power to the non-nicotine electronic vaping device. The fault event may be a power supply temperature fault event indicating that a temperature of the power supply is greater than or equal to a maximum threshold value. The controller may be configured to perform the at least one consequent action by preventing charging of the power supply in response to detecting the power supply temperature fault event.

At least one example embodiment provides a method of operating a non-nicotine electronic vaping device, the method comprising: detecting a fault event at the non-nicotine electronic vaping device; classifying the fault event as one of a plurality of types of fault events; and performing at least one consequent action based on the classification of the fault event.

According to at least some example embodiments, the fault event may be one of a normal event, a soft fault pod event, a hard fault pod event, a soft fault device event, or a hard fault device event. The soft fault pod event and the hard fault pod event may be abnormal conditions at the non-nicotine pod assembly, and the soft fault device event and the hard fault device event may be abnormal conditions at the device body.

The at least one consequent action may include an auto off operation, a heater off operation, a vaping off operation, a charging stop operation, or a combination thereof.

The performing at least one consequent action may include: disabling power to a heater at the non-nicotine electronic vaping device; logging an occurrence of the fault event in a memory at the non-nicotine electronic vaping device; and outputting an indication that the fault event has occurred.

The performing at least one consequent action may include: disabling a vaping function at the non-nicotine electronic vaping device; logging an occurrence of the fault event in a memory at the non-nicotine electronic vaping device; and outputting an indication that the fault event has occurred.

The method may further include: detecting removal of a non-nicotine pod assembly from the non-nicotine electronic vaping device; and enabling the vaping function at the non-nicotine electronic vaping device in response to detecting removal of the non-nicotine pod assembly from the non-nicotine electronic vaping device.

The method may further include causing the non-nicotine electronic vaping device to enter a sleep mode in response to determining that a corrective action has not occurred in response to the fault event.

The performing at least one consequent action may include: initiating an auto off operation in which the non-nicotine electronic vaping device enters a sleep mode; logging an occurrence of the fault event in a memory at the non-nicotine electronic vaping device; and outputting an indication that the fault event has occurred.

The performing at least one consequent action may include: disabling a vaping function, a charging operation, or the vaping function and the charging operation, at the non-nicotine electronic vaping device; logging an occurrence of the fault event in a memory at the non-nicotine electronic vaping device; and outputting an indication that the fault event has occurred.

The method may further include: initiating a reset timer in response to detecting the fault event; determining that the reset timer has lapsed; and performing a reset of the non-nicotine electronic vaping device in response to determining that the reset timer has lapsed.

The method may further include: determining that the fault event has been cleared by the reset; and enabling the vaping function, the charging operation, or the vaping function and the charging operation, at the non-nicotine electronic vaping device in response to determining that the fault event has been cleared by the reset.

The method may further include: detecting a corrective action at the non-nicotine electronic vaping device; and enabling the vaping function, the charging operation, or the vaping function and the charging operation, at the non-nicotine electronic vaping device in response to detecting the corrective action.

The detecting a fault event may include: obtaining a threshold temperature value from a memory at the non-nicotine electronic vaping device; estimating a temperature of a heater at the non-nicotine electronic vaping device; and detecting the fault event in response to determining that the temperature of the heater is greater than or equal to the threshold temperature value.

The fault event may be a power supply low voltage fault event indicating that a voltage of a power supply at the non-nicotine electronic vaping device is less than a minimum threshold value. The performing the at least one consequent action may include disabling a vaping function at the non-nicotine electronic vaping device in response to detecting the power supply low voltage fault event.

The fault event may be a power supply temperature fault event indicating that a temperature of a power supply at the non-nicotine electronic vaping device is greater than or equal to a maximum threshold value. The performing the at least one consequent action may include preventing charging of the power supply in response to detecting the power supply temperature fault event.

BRIEF DESCRIPTION OF THE DRAWINGS

The various features and advantages of the non-limiting embodiments herein may become more apparent upon review of the detailed description in conjunction with the accompanying drawings. The accompanying drawings are merely provided for illustrative purposes and should not be interpreted to limit the scope of the claims. The accompanying drawings are not to be considered as drawn to scale unless explicitly noted. For purposes of clarity, various dimensions of the drawings may have been exaggerated.

DETAILED DESCRIPTION

Figure 1:
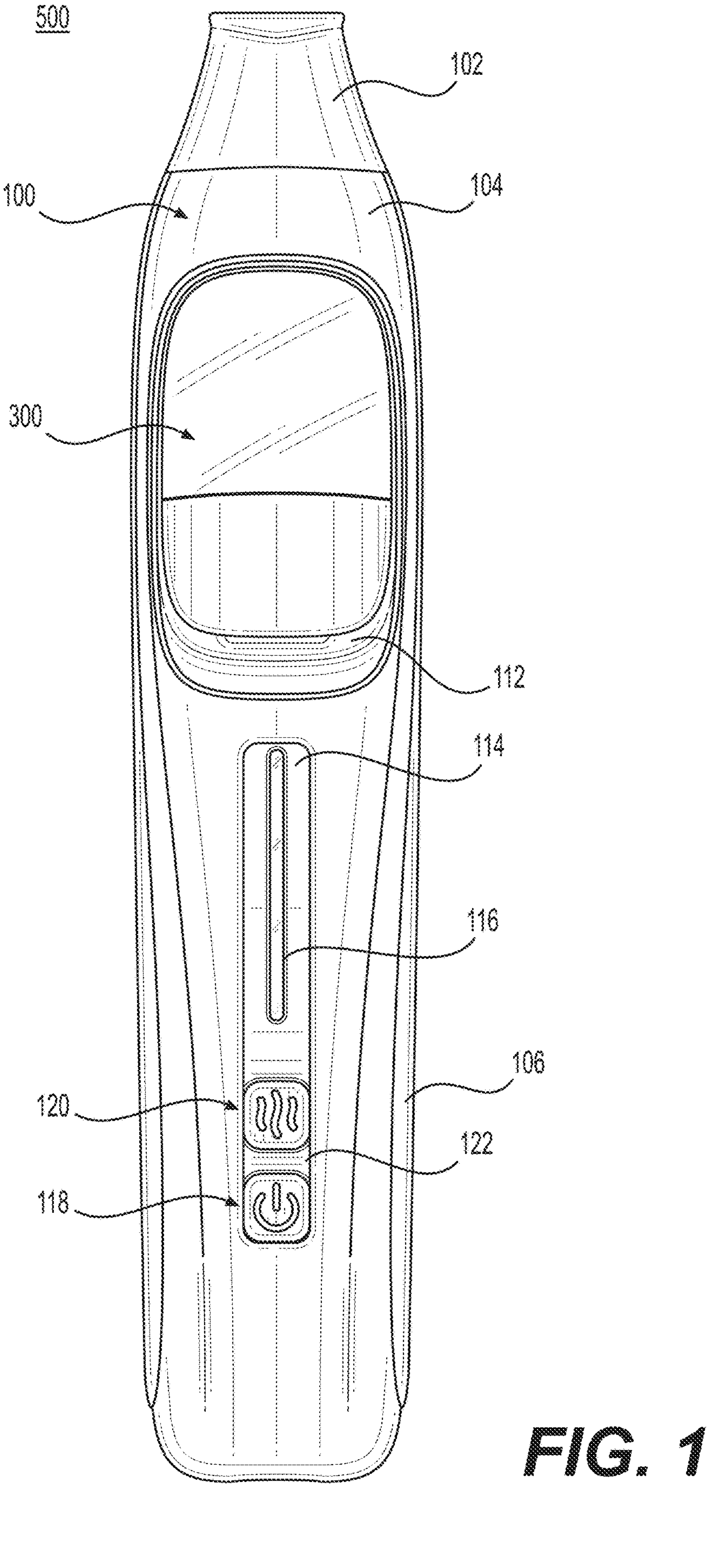
FIG. 1 is a front view of a non-nicotine e-vaping device according to an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the example embodiments set forth herein.

Accordingly, while example embodiments are capable of various modifications and alternative forms, example embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives thereof. Like numbers refer to like elements throughout the description of the figures.

It should be understood that when an element or layer is referred to as being "on," "connected to," "coupled to," "attached to," "adjacent to," or "covering" another element or layer, it may be directly on, connected to, coupled to, attached to, adjacent to or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations or sub-combinations of one or more of the associated listed items.

It should be understood that, although the terms first, second, third, etc. may be used herein to describe various elements, regions, layers and/or sections, these elements, regions, layers, and/or sections should not be limited by these terms. These terms are only used to distinguish one element, region, layer, or section from another region, layer, or section. Thus, a first element, region, layer, or section discussed below could be termed a second element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various example embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations and/or elements but do not preclude the presence or addition of one or more other features, integers, steps, operations, elements, and/or groups thereof.

When the words "about" and "substantially" are used in this specification in connection with a numerical value, it is intended that the associated numerical value include a tolerance of ±10% around the stated numerical value, unless otherwise explicitly defined.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

A "non-nicotine electronic vaping device" or "non-nicotine e-vaping device" as used herein may be referred to on occasion using, and considered synonymous with, non-nicotine e-vapor apparatus and/or non-nicotine e-vaping apparatus.

Figure 2:
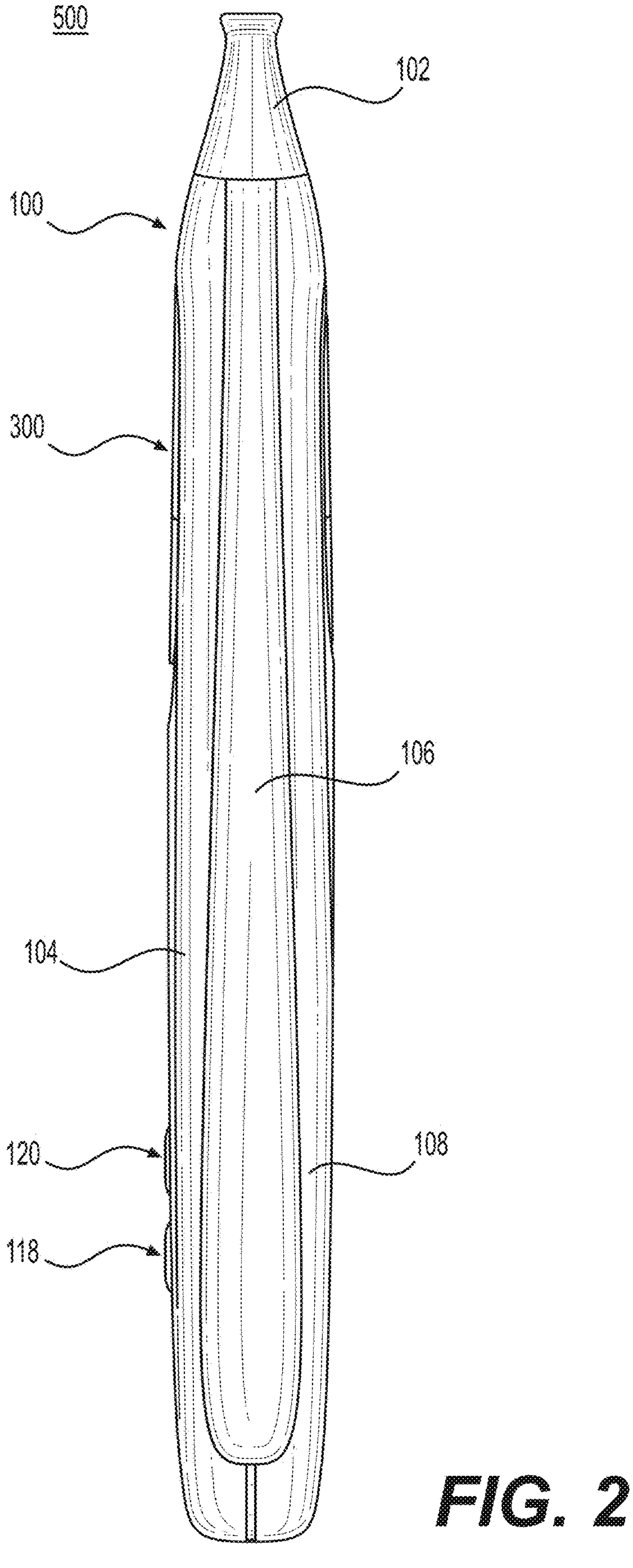
FIG. 2 is a side view of the non-nicotine e-vaping device of FIG. 1.
Figure 3:
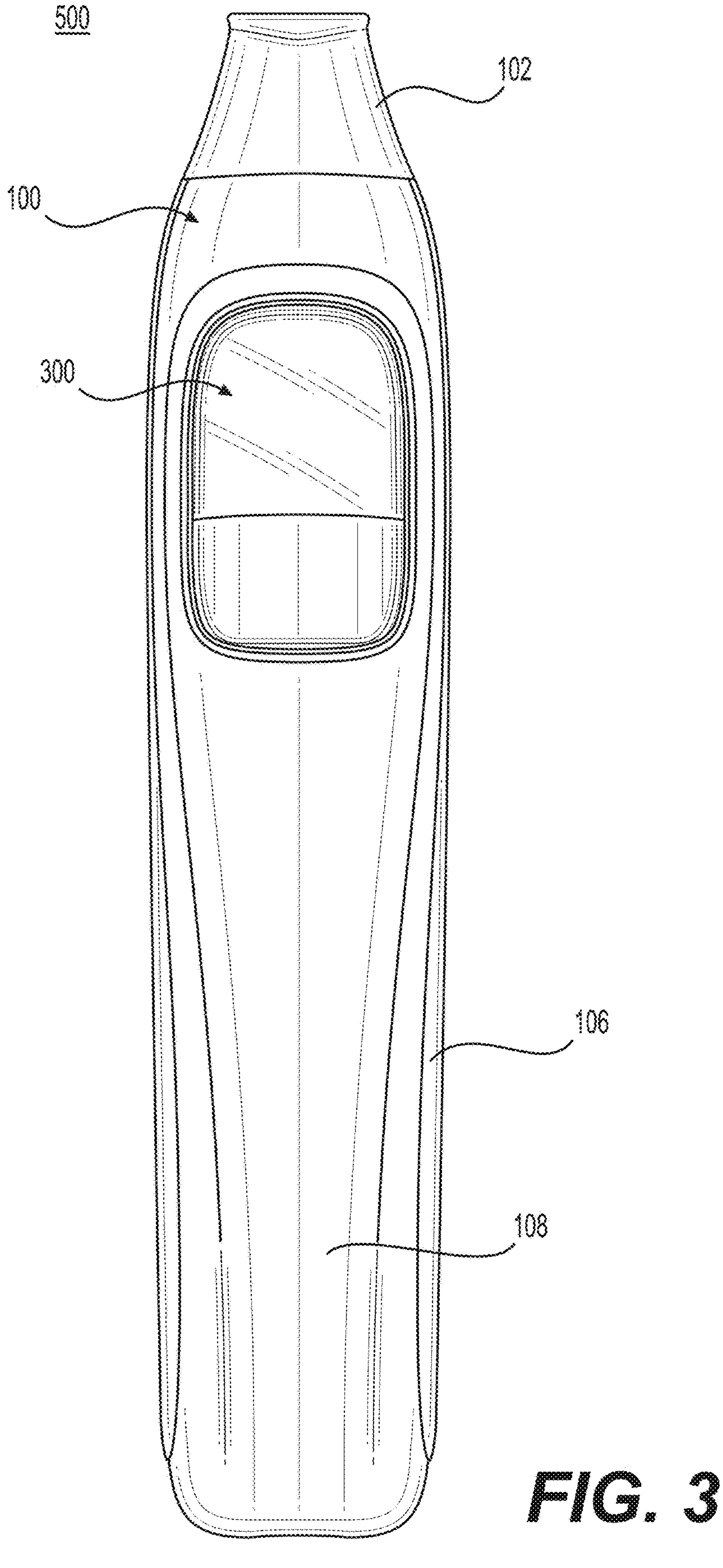
FIG. 3 is a rear view of the non-nicotine e-vaping device of FIG. 1.

FIG. 1 is a front view of a non-nicotine e-vaping device according to an example embodiment. FIG. 2 is a side view of the non-nicotine e-vaping device of FIG. 1. FIG. 3 is a rear view of the non-nicotine e-vaping device of FIG. 1. Referring to FIGS. 1-3, a non-nicotine e-vaping device 500 includes a device body 100 that is configured to receive a non-nicotine pod assembly 300. The non-nicotine pod assembly 300 is a modular article configured to hold a non-nicotine pre-vapor formulation. A "non-nicotine pre-vapor formulation" is a material or combination of materials that may be transformed into a vapor. For example, the non-nicotine pre-vapor formulation may be a liquid, solid, and/or gel formulation including, but not limited to, water, beads, solvents, active ingredients, ethanol, plant extracts, natural or artificial flavors, and/or vapor formers such as glycerin and propylene glycol.

In an example embodiment, the non-nicotine pre-vapor formulation neither includes tobacco nor is derived from tobacco. A non-nicotine compound of the non-nicotine pre-vapor formulation may be part of, or included in a liquid or a partial-liquid that includes an extract, an oil, an alcohol, a tincture, a suspension, a dispersion, a colloid, a general non-neutral (slightly acidic or slightly basic) solution, or combinations thereof. During the preparation of the non-nicotine pre-vapor formulation, the non-nicotine compound may be infused into, comingled, or otherwise combined with the other ingredients of the non-nicotine pre-vapor formulation.

In an example embodiment, the non-nicotine compound undergoes a slow, natural decarboxylation process over an extended duration of time at relatively low temperatures, including at or below room temperature (e.g., 72° F.). In addition, the non-nicotine compound may undergo a significantly elevated decarboxylation process (e.g., 50% decarboxylation or greater) if exposed to elevated temperatures, especially in the range of about 175° F. or greater over a period of time (minutes or hours) at a relatively low pressure such as 1 atmosphere. Higher temperatures of about 240° F. or greater can cause a rapid or instantaneous decarboxylation to occur at a relatively high decarboxylation rate, although further elevated temperatures can cause a degradation of some or all of the chemical properties of the non-nicotine compound(s).

In an example embodiment, the non-nicotine compound may be from a medicinal plant (e.g., a naturally-occurring constituent of a plant that provides a medically-accepted therapeutic effect). The medicinal plant may be a cannabis plant, and the constituent may be at least one cannabis-derived constituent. Cannabinoids (e.g., phytocannabinoids) and terpenes are examples of cannabis-derived constituents. Cannabinoids interact with receptors in the body to produce a wide range of effects. As a result, cannabinoids have been used for a variety of medicinal purposes. Cannabis-derived materials may include the leaf and/or flower material from one or more species of cannabis plants, or extracts from the one or more species of cannabis plants. For instance, the one or more species of cannabis plants may include *Cannabis sativa, Cannabis indica*, and *Cannabis ruderalis*. In some example embodiments, the non-nicotine pre-vapor formulation includes a mixture of cannabis and/or cannabis-derived constituents that are, or are derived from, 60-80% (e.g., 70%) *Cannabis sativa* and 20-40% (e.g., 30%) *Cannabis indica.*

Non-limiting examples of cannabis-derived cannabinoids include tetrahydrocannabinolic acid (THCA), tetrahydrocannabinol (THC), cannabidiolic acid (CBDA), cannabidiol (CBD), cannabinol (CBN), cannabicyclol (CBL), cannabichromene (CBC), and cannabigerol (CBG). Tetrahydrocannabinolic acid (THCA) is a precursor of tetrahydrocannabinol (THC), while cannabidiolic acid (CBDA) is precursor of cannabidiol (CBD). Tetrahydrocannabinolic acid (TI-ICA) and cannabidiolic acid (CBDA) may be converted to tetrahydrocannabinol (THC) and cannabidiol (CBD), respectively, via heating. In an example embodiment, heat from the heater may cause decarboxylation to convert tetrahydrocannabinolic acid (THCA) in the non-nicotine pre-vapor formulation to tetrahydrocannabinol (THC), and/or to convert cannabidiolic acid (CBDA) in the non-nicotine pre-vapor formulation to cannabidiol (CBD).

In instances where both tetrahydrocannabinolic acid (THCA) and tetrahydrocannabinol (THC) are present in the non-nicotine pre-vapor formulation, the decarboxylation and resulting conversion will cause a decrease in tetrahydrocannabinolic acid (THCA) and an increase in tetrahydrocannabinol (THC). At least 50% (e.g., at least 87%) of the tetrahydrocannabinolic acid (THCA) may be converted to tetrahydrocannabinol (THC), via the decarboxylation process, during the heating of the non-nicotine pre-vapor formulation for purposes of vaporization. Similarly, in instances where both cannabidiolic acid (CBDA) and cannabidiol (CBD) are present in the non-nicotine pre-vapor formulation, the decarboxylation and resulting conversion will cause a decrease in cannabidiolic acid (CBDA) and an increase in cannabidiol (CBD). At least 50% (e.g., at least 87%) of the cannabidiolic acid (CBDA) may be converted to cannabidiol (CBD), via the decarboxylation process, during the heating of the non-nicotine pre-vapor formulation for purposes of vaporization.

The non-nicotine pre-vapor formulation may contain the non-nicotine compound that provides the medically-accepted therapeutic effect (e.g., treatment of pain, nausea, epilepsy, psychiatric disorders). Details on methods of treatment may be found in U.S. application Ser. No. 15/845,501, filed Dec. 18, 2017, titled "VAPORIZING DEVICES AND METHODS FOR DELIVERING A COMPOUND USING THE SAME," the disclosure of which is incorporated herein in its entirety by reference.

In an example embodiment, at least one flavorant is present in an amount ranging from about 0.2% to about 15% by weight (e.g., about 1% to 12%, about 2% to 10%, or about 5% to 8%) based on a total weight of the non-nicotine pre-vapor formulation. The at least one flavorant may be at least one of a natural flavorant, an artificial flavorant, or a combination of a natural flavorant and an artificial flavorant. The at least one flavorant may include volatile cannabis flavor compounds (flavonoids) or other flavor compounds instead of, or in addition to, the cannabis flavor compounds. For instance, the at least one flavorant may include menthol, wintergreen, peppermint, cinnamon, clove, combinations thereof, and/or extracts thereof. In addition, flavorants may be included to provide other herb flavors, fruit flavors, nut flavors, liquor flavors, roasted flavors, minty flavors, savory flavors, combinations thereof, and any other desired flavors.

During vaping, the non-nicotine e-vaping device 500 is configured to heat the non-nicotine pre-vapor formulation to generate a vapor. As referred to herein, a “non-nicotine vapor” is any matter generated or outputted from any non-nicotine e-vaping device according to any of the example embodiments disclosed herein.

As shown in FIGS. 1 and 3, the non-nicotine e-vaping device 500 extends in a longitudinal direction and has a length that is greater than its width. In addition, as shown in FIG. 2, the length of the non-nicotine e-vaping device 500 is also greater than its thickness. Furthermore, the width of the non-nicotine e-vaping device 500 may be greater than its thickness. Assuming an x-y-z Cartesian coordinate system, the length of the non-nicotine e-vaping device 500 may be measured in the y-direction, the width may be measured in the x-direction, and the thickness may be measured in the z-direction. The non-nicotine e-vaping device 500 may have a substantially linear form with tapered ends based on its front, side, and rear views, although example embodiments are not limited thereto.

The device body 100 includes a front cover 104, a frame 106, and a rear cover 108. The front cover 104, the frame 106, and the rear cover 108 form a device housing that encloses mechanical elements, electronic elements, and/or circuitry associated with the operation of the non-nicotine e-vaping device 500. For instance, the device housing of the device body 100 may enclose a power source configured to power the non-nicotine e-vaping device 500, which may include supplying an electric current to the non-nicotine pod assembly 300. The device housing of the device body 100 may also include one or more electrical systems to control the non-nicotine e-vaping device 500. Electrical systems according to example embodiments will be discussed in more detail later. In addition, when assembled, the front cover 104, the frame 106, and the rear cover 108 may constitute a majority of the visible portion of the device body 100.

The front cover 104 (e.g., first cover) defines a primary opening configured to accommodate a bezel structure 112. The primary opening may have a rounded rectangular shape, although other shapes are possible depending on the shape of the bezel structure 112. The bezel structure 112 defines a through hole 150 configured to receive the non-nicotine pod assembly 300. The through hole 150 is discussed herein in more detail in connection with, for instance, FIG. 9.

The front cover 104 also defines a secondary opening configured to accommodate a light guide arrangement. The secondary opening may resemble a slot (e.g., elongated rectangle with rounded edges), although other shapes are possible depending on the shape of the light guide arrangement. In an example embodiment, the light guide arrangement includes a light guide housing 114 and a button housing 122. The light guide housing 114 is configured to expose a light guide lens 116, while the button housing 122 is configured to expose a first button lens 124 and a second button lens 126 (e.g., FIG. 16). The first button lens 124 and an upstream portion of the button housing 122 may form a first button 118. Similarly, the second button lens 126 and a downstream portion of the button housing 122 may form a second button 120. The button housing 122 may be in a form of a single structure or two separate structures. With the latter form, the first button 118 and the second button 120 can move with a more independent feel when pressed.

The operation of the non-nicotine e-vaping device 500 may be controlled by the first button 118 and the second button 120. For instance, the first button 118 may be a power button, and the second button 120 may be an intensity button. Although two buttons are shown in the drawings in connection with the light guide arrangement, it should be understood that more (or less) buttons may be provided depending on the available features and desired user interface.

The frame 106 (e.g., base frame) is the central support structure for the device body 100 (and the non-nicotine e-vaping device 500 as a whole). The frame 106 may be referred to as a chassis. The frame 106 includes a proximal end, a distal end, and a pair of side sections between the proximal end and the distal end. The proximal end and the distal end may also be referred to as the downstream end and the upstream end, respectively. As used herein, “proximal” (and, conversely, “distal”) is in relation to an adult vaper during vaping, and “downstream” (and, conversely, “upstream”) is in relation to a flow of the non-nicotine vapor. A bridging section may be provided between the opposing inner surfaces of the side sections (e.g., about midway along the length of the frame 106) for additional strength and stability. The frame 106 may be integrally formed so as to be a monolithic structure.

With regard to material of construction, the frame 106 may be formed of an alloy or a plastic. The alloy (e.g., die cast grade, machinable grade) may be an aluminum (Al) alloy or a zinc (Zn) alloy. The plastic may be a polycarbonate (PC), an acrylonitrile butadiene styrene (ABS), or a combination thereof (PC/ABS). For instance, the polycarbonate may be LUPOY SC1004A. Furthermore, the frame 106 may be provided with a surface finish for functional and/or aesthetic reasons (e.g., to provide a premium appearance). In an example embodiment, the frame 106 (e.g., when formed of an aluminum alloy) may be anodized. In another embodiment, the frame 106 (e.g., when formed of a zinc alloy) may be coated with a hard enamel or painted. In another embodiment, the frame 106 (e.g., when formed of a polycarbonate) may be metallized. In yet another embodiment, the frame 106 (e.g., when formed of an acrylonitrile butadiene styrene) may be electroplated. It should be understood that the materials of construction with regard to the frame 106 may also be applicable to the front cover 104, the rear cover 108, and/or other appropriate parts of the non-nicotine e-vaping device 500.

The rear cover 108 (e.g., second cover) also defines an opening configured to accommodate the bezel structure 112. The opening may have a rounded rectangular shape, although other shapes are possible depending on the shape of the bezel structure 112. In an example embodiment, the opening in the rear cover 108 is smaller than the primary opening in the front cover 104. In addition, although not shown, it should be understood that a light guide arrangement (e.g., including buttons) may be provided on the rear of the non-nicotine e-vaping device 500 in addition to (or in lieu of) the light guide arrangement on the front of the non-nicotine e-vaping device 500.

The front cover 104 and the rear cover 108 may be configured to engage with the frame 106 via a snap-fit arrangement. For instance, the front cover 104 and/or the rear cover 108 may include clips configured to interlock with corresponding mating members of the frame 106. In a non-limiting embodiment, the clips may be in a form of tabs with orifices configured to receive the corresponding mating members (e.g., protrusions with beveled edges) of the frame 106. Alternatively, the front cover 104 and/or the rear cover 108 may be configured to engage with the frame 106 via an interference fit (which may also be referred to as a press fit or friction fit). However, it should be understood that the front cover 104, the frame 106, and the rear cover 108 may be coupled via other suitable arrangements and techniques.

The device body 100 also includes a mouthpiece 102. The mouthpiece 102 may be secured to the proximal end of the frame 106. Additionally, as shown in FIG. 2, in an example embodiment where the frame 106 is sandwiched between the front cover 104 and the rear cover 108, the mouthpiece 102 may abut the front cover 104, the frame 106, and the rear cover 108. Furthermore, in a non-limiting embodiment, the mouthpiece 102 may be joined with the device housing via a bayonet connection.

Figure 4:
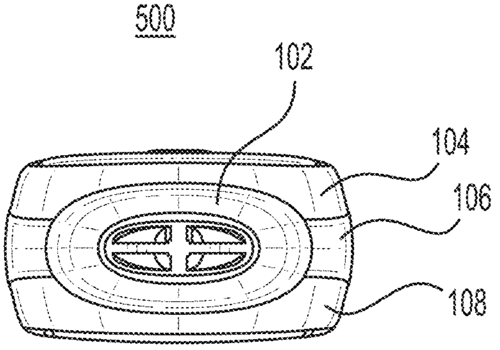
FIG. 4 is a proximal end view of the non-nicotine e-vaping device of FIG. 1.

FIG. 4 is a proximal end view of the non-nicotine e-vaping device of FIG. 1. Referring to FIG. 4, the outlet face of the mouthpiece 102 defines a plurality of vapor outlets. In a non-limiting embodiment, the outlet face of the mouthpiece 102 may be elliptically-shaped. In addition, the outlet face of the mouthpiece 102 may include a first crossbar corresponding to a major axis of the elliptically-shaped outlet face and a second crossbar corresponding to a minor axis of the elliptically-shaped outlet face. Furthermore, the first crossbar and the second crossbar may intersect perpendicularly and be integrally formed parts of the mouthpiece 102. Although the outlet face is shown as defining four vapor outlets, it should be understood that example embodiments are not limited thereto. For instance, the outlet face may define less than four (e.g., one, two) vapor outlets or more than four (e.g., six, eight) vapor outlets.

Figure 5:
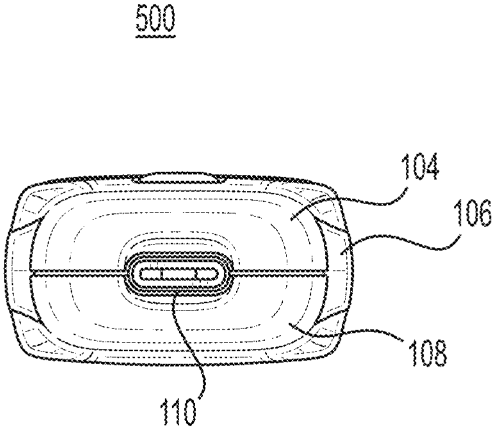
FIG. 5 is a distal end view of the non-nicotine e-vaping device of FIG. 1.

FIG. 5 is a distal end view of the non-nicotine e-vaping device of FIG. 1. Referring to FIG. 5, the distal end of the non-nicotine e-vaping device 500 includes a port 110. The port 110 is configured to receive an electric current (e.g., via a USB cable) from an external power source so as to charge an internal power source within the non-nicotine e-vaping device 500. In addition, the port 110 may also be configured to send data to and/or receive data (e.g., via a USB cable) from another non-nicotine e-vaping device or other electronic device (e.g., phone, tablet, computer). Furthermore, the non-nicotine e-vaping device 500 may be configured for wireless communication with another electronic device, such as a phone, via an application software (app) installed on that electronic device. In such an instance, an adult vaper may control or otherwise interface with the non-nicotine e-vaping device 500 (e.g., locate the non-nicotine e-vaping device, check usage information, change operating parameters) through the app.

Figure 6:
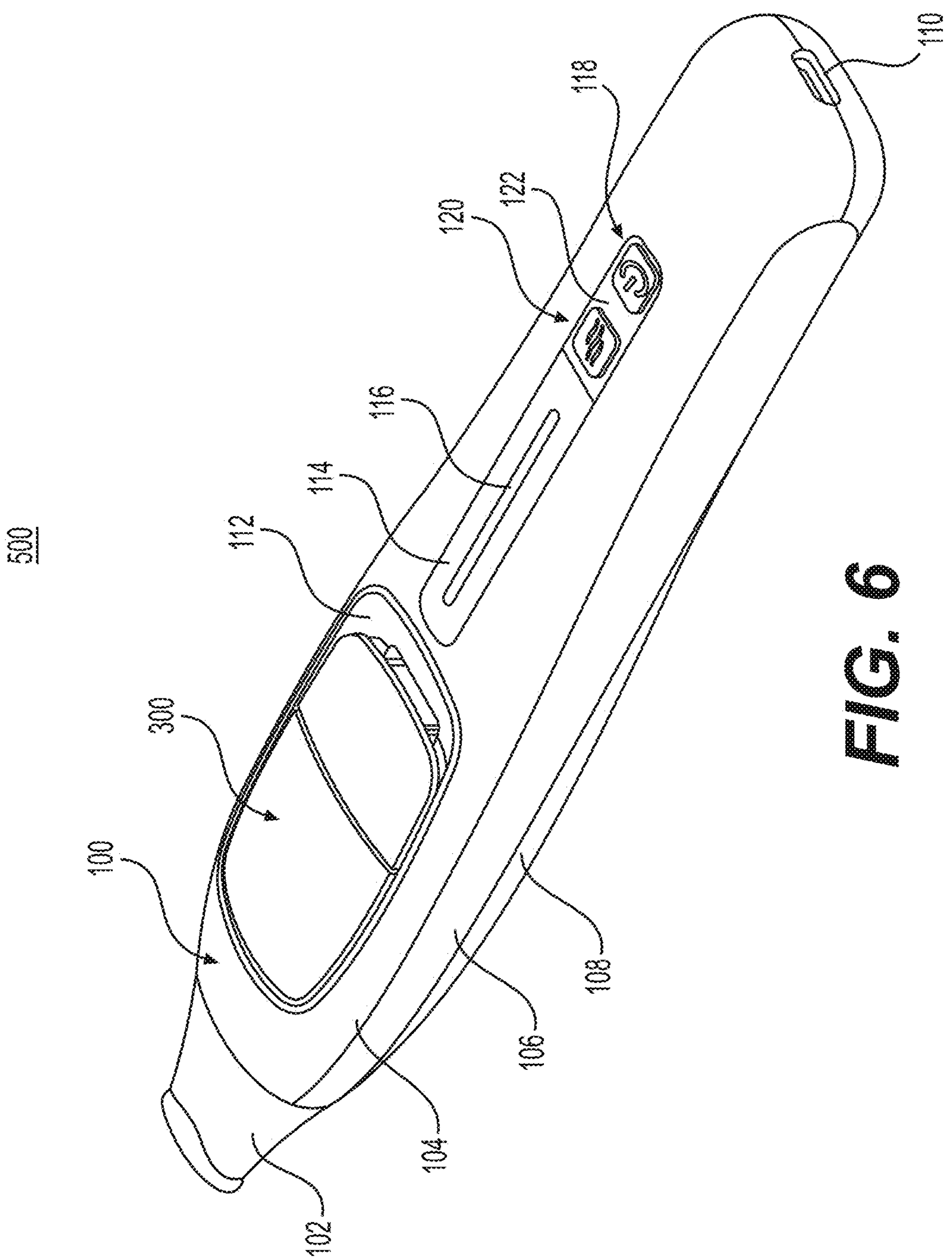
FIG. 6 is a perspective view of the non-nicotine e-vaping device of FIG. 1.
Figure 7:
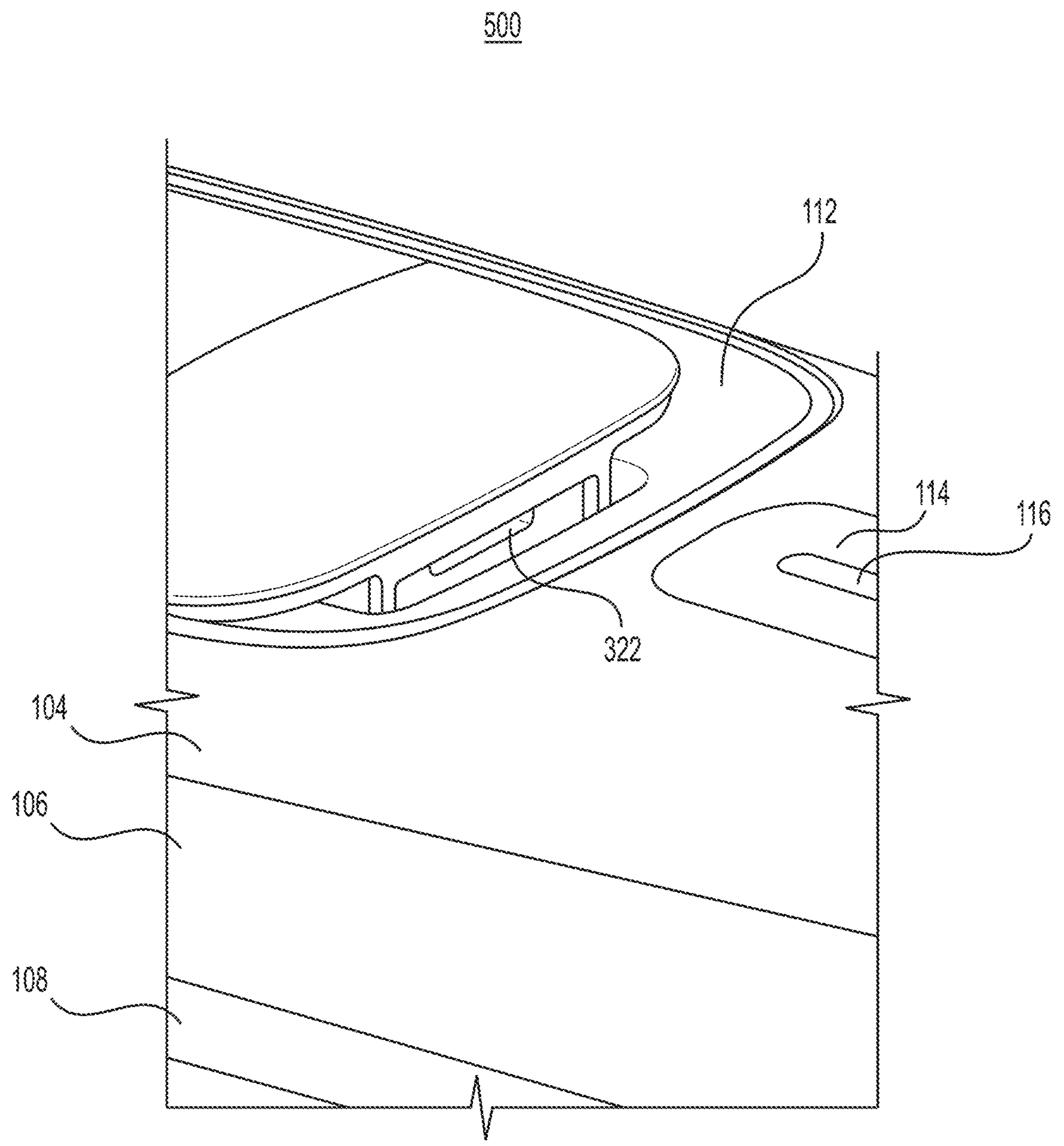
FIG. 7 is an enlarged view of the pod inlet in FIG. 6.

FIG. 6 is a perspective view of the non-nicotine e-vaping device of FIG. 1. FIG. 7 is an enlarged view of the pod inlet in FIG. 6. Referring to FIGS. 6-7, and as briefly noted above, the non-nicotine e-vaping device 500 includes a non-nicotine pod assembly 300 configured to hold a non-nicotine pre-vapor formulation. The non-nicotine pod assembly 300 has an upstream end (which faces the light guide arrangement) and a downstream end (which faces the mouthpiece 102). In a non-limiting embodiment, the upstream end is an opposing surface of the non-nicotine pod assembly 300 from the downstream end. The upstream end of the non-nicotine pod assembly 300 defines a pod inlet 322. The device body 100 defines a through hole (e.g., through hole 150 in FIG. 9) configured to receive the non-nicotine pod assembly 300. In an example embodiment, the bezel structure 112 of the device body 100 defines the through hole and includes an upstream rim. As shown, particularly in FIG. 7, the upstream rim of the bezel structure 112 is angled (e.g., dips inward) so as to expose the pod inlet 322 when the non-nicotine pod assembly 300 is seated within the through hole of the device body 100.

For instance, rather than following the contour of the front cover 104 (so as to be relatively flush with the front face of the non-nicotine pod assembly 300 and, thus, obscure the pod inlet 322), the upstream rim of the bezel structure 112 is in a form of a scoop configured to direct ambient air into the pod inlet 322. This angled/scoop configuration may help reduce or prevent the blockage of the air inlet (e.g., pod inlet 322) of the non-nicotine e-vaping device 500. The depth of the scoop may be such that less than half (e.g., less than a quarter) of the upstream end face of the non-nicotine pod assembly 300 is exposed. Additionally, in a non-limiting embodiment, the pod inlet 322 is in a form of a slot. Furthermore, if the device body 100 is regarded as extending in a first direction, then the slot may be regarded as extending in a second direction, wherein the second direction is transverse to the first direction.

Figure 8:
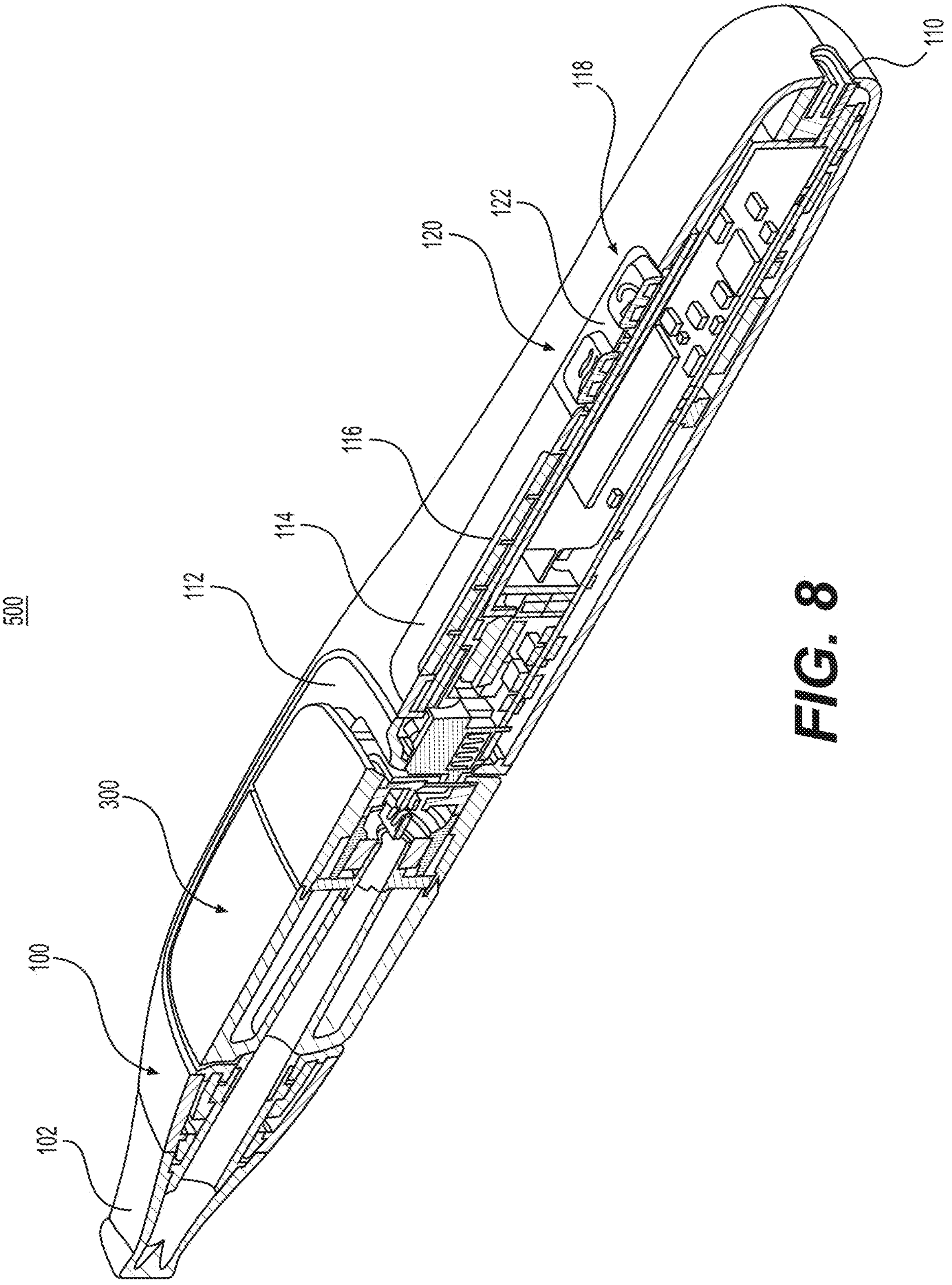
FIG. 8 is a cross-sectional view of the non-nicotine e-vaping device of FIG. 6.

FIG. 8 is a cross-sectional view of the non-nicotine e-vaping device of FIG. 6. In FIG. 8, the cross-section is taken along the longitudinal axis of the non-nicotine e-vaping device 500. As shown, the device body 100 and the non-nicotine pod assembly 300 include mechanical elements, electronic elements, and/or circuitry associated with the operation of the non-nicotine e-vaping device 500, which are discussed in more detail herein and/or are incorporated by reference herein. For instance, the non-nicotine pod assembly 300 may include mechanical elements configured to actuate to release the non-nicotine pre-vapor formulation from a sealed non-nicotine reservoir within. The non-nicotine pod assembly 300 may also have mechanical aspects configured to engage with the device body 100 to facilitate the insertion and seating of the non-nicotine pod assembly 300.

Additionally, the non-nicotine pod assembly 300 may be a "smart pod" that includes electronic elements and/or circuitry configured to store, receive, and/or transmit information to/from the device body 100. Such information may be used to authenticate the non-nicotine pod assembly 300 for use with the device body 100 (e.g., to prevent usage of an unapproved/counterfeit non-nicotine pod assembly). Furthermore, the information may be used to identify a type of the non-nicotine pod assembly 300 which is then correlated with a vaping profile based on the identified type. The vaping profile may be designed to set forth the general parameters for the heating of the non-nicotine pre-vapor formulation and may be subject to tuning, refining, or other adjustment by an adult vaper before and/or during vaping.

The non-nicotine pod assembly 300 may also communicate with the device body 100 other information that may be relevant to the operation of the non-nicotine e-vaping device 500. Examples of relevant information may include a level of the non-nicotine pre-vapor formulation within the non-nicotine pod assembly 300 and/or a length of time that has passed since the non-nicotine pod assembly 300 was inserted into the device body 100 and activated. For instance, if the non-nicotine pod assembly 300 was inserted into the device body 100 and activated more than a certain period of time prior (e.g., more than 6 months ago), the non-nicotine e-vaping device 500 may not permit vaping, and the adult vaper may be prompted to change to a new non-nicotine pod assembly even though the non-nicotine pod assembly 300 still contains adequate levels of non-nicotine pre-vapor formulation.

The device body 100 may include mechanical elements (e.g. complementary structures) configured to engage, hold, and/or activate the non-nicotine pod assembly 300. In addition, the device body 100 may include electronic elements and/or circuitry configured to receive an electric current to charge an internal power source (e.g., battery) which, in turn, is configured to supply power to the non-nicotine pod assembly 300 during vaping. Furthermore, the device body 100 may include electronic elements and/or circuitry configured to communicate with the non-nicotine pod assembly 300, a different non-nicotine e-vaping device, other electronic devices (e.g., phone, tablet, computer), and/or the adult vaper. The information being communicated may include pod-specific data, current vaping details, and/or past vaping patterns/history. The adult vaper may be notified of such communications with feedback that is haptic (e.g., vibrations), auditory (e.g., beeps), and/or visual (e.g., colored/blinking lights). The charging and/or communication of information may be performed with the port 110 (e.g., via a USB cable).

Figure 9:
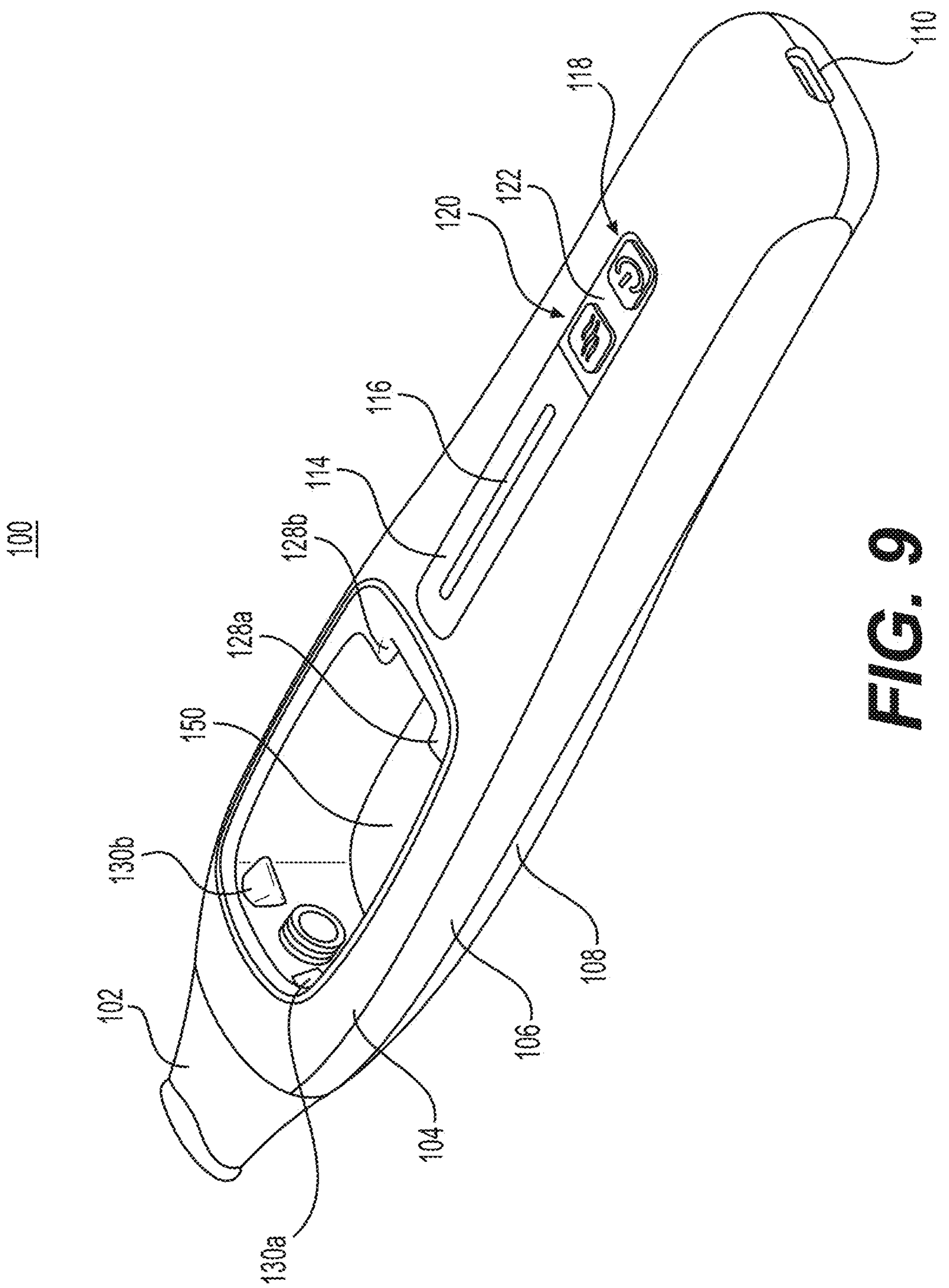
FIG. 9 is a perspective view of the device body of the non-nicotine e-vaping device of FIG. 6.

FIG. 9 is a perspective view of the device body of the non-nicotine e-vaping device of FIG. 6. Referring to FIG. 9, the bezel structure 112 of the device body 100 defines a through hole 150. The through hole 150 is configured to receive a non-nicotine pod assembly 300. To facilitate the insertion and seating of the non-nicotine pod assembly 300 within the through hole 150, the upstream rim of the bezel structure 112 includes a first upstream protrusion 128*a* and a second upstream protrusion 128*b*. The through hole 150 may have a rectangular shape with rounded corners. In an example embodiment, the first upstream protrusion 128*a* and the second upstream protrusion 128*b* are integrally formed with the bezel structure 112 and located at the two rounded corners of the upstream rim.

The downstream sidewall of the bezel structure 112 may define a first downstream opening, a second downstream opening, and a third downstream opening. A retention structure including a first downstream protrusion 130*a* and a second downstream protrusion 130*b* is engaged with the bezel structure 112 such that the first downstream protrusion 130*a* and the second downstream protrusion 130*b* protrude through the first downstream opening and the second downstream opening, respectively, of the bezel structure 112 and into the through hole 150. In addition, a distal end of the mouthpiece 102 extends through the third downstream opening of the bezel structure 112 and into the through hole 150 so as to be between the first downstream protrusion 130*a* and the second downstream protrusion 130*b*.

Figure 10:
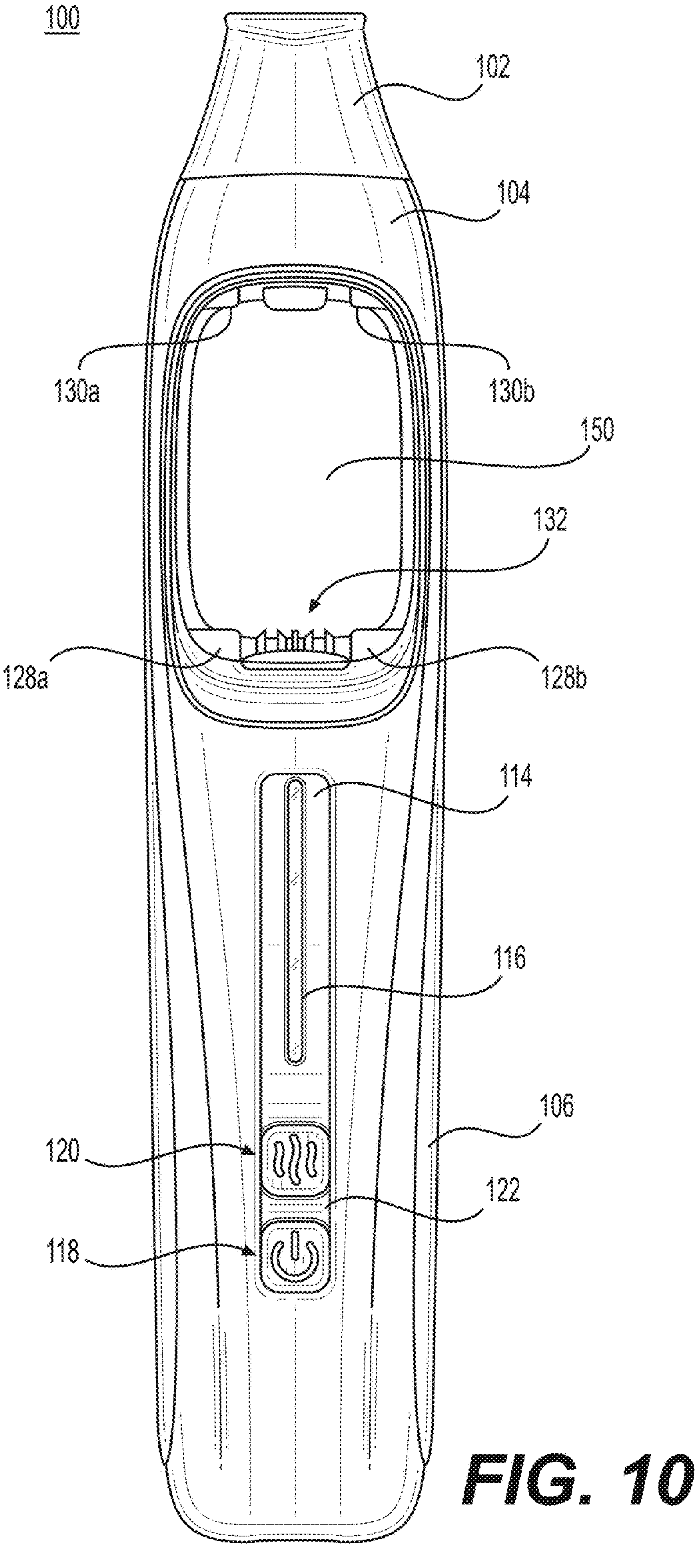
FIG. 10 is a front view of the device body of FIG. 9.

FIG. 10 is a front view of the device body of FIG. 9. Referring to FIG. 10, the device body 100 includes a device electrical connector 132 disposed at an upstream side of the through hole 150. The device electrical connector 132 of the device body 100 is configured to electrically engage with a non-nicotine pod assembly 300 that is seated within the through hole 150. As a result, power can be supplied from the device body 100 to the non-nicotine pod assembly 300 via the device electrical connector 132 during vaping. In addition, data can be sent to and/or received from the device body 100 and the non-nicotine pod assembly 300 via the device electrical connector 132.

Figure 11:
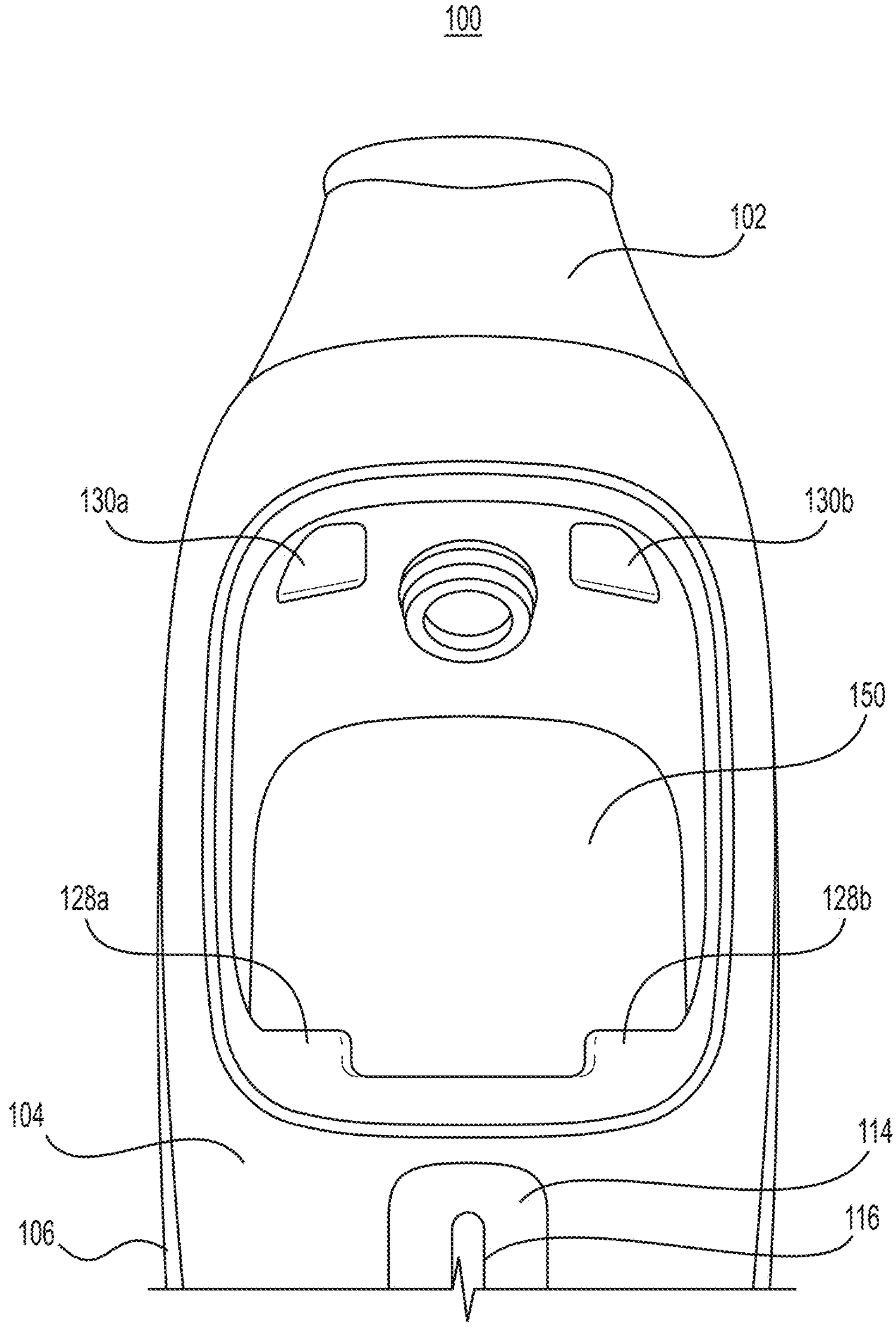
FIG. 11 is an enlarged perspective view of the through hole in FIG. 10.

FIG. 11 is an enlarged perspective view of the through hole in FIG. 10. Referring to FIG. 11, the first upstream protrusion 128*a*, the second upstream protrusion 128*b*, the first downstream protrusion 130*a*, the second downstream protrusion 130*b*, and the distal end of the mouthpiece 102 protrude into the through hole 150. In an example embodiment, the first upstream protrusion 128*a* and the second upstream protrusion 128*b* are stationary structures (e.g., stationary pivots), while the first downstream protrusion 130*a* and the second downstream protrusion 130*b* are tractable structures (e.g., retractable members). For instance, the first downstream protrusion 130*a* and the second downstream protrusion 130*b* may be configured (e.g., spring-loaded) to default to a protracted state while also configured to transition temporarily to a retracted state (and reversibly back to the protracted state) to facilitate an insertion of a non-nicotine pod assembly 300.

In particular, when inserting a non-nicotine pod assembly 300 into the through hole 150 of the device body 100, recesses at the upstream end face of the non-nicotine pod assembly 300 may be initially engaged with the first upstream protrusion 128*a* and the second upstream protrusion 128*b* followed by a pivoting of the non-nicotine pod assembly 300 (about the first upstream protrusion 128*a* and the second upstream protrusion 128*b*) until recesses at the downstream end face of the non-nicotine pod assembly 300 are engaged with the first downstream protrusion 130*a* and the second downstream protrusion 130*b*. In such an instance, the axis of rotation (during pivoting) of the non-nicotine pod assembly 300 may be orthogonal to the longitudinal axis of the device body 100. In addition, the first downstream protrusion 130*a* and the second downstream protrusion 130*b*, which may be biased so as to be tractable, may retract when the non-nicotine pod assembly 300 is being pivoted into the through hole 150 and resiliently protract to engage recesses at the downstream end face of the non-nicotine pod assembly 300. Furthermore, the engagement of the first downstream protrusion 130*a* and the second downstream protrusion 130*b* with recesses at the downstream end face of the non-nicotine pod assembly 300 may produce a haptic and/or auditory feedback (e.g., audible click) to notify an adult vaper that the non-nicotine pod assembly 300 is properly seated in the through hole 150 of the device body 100.

Figure 12:
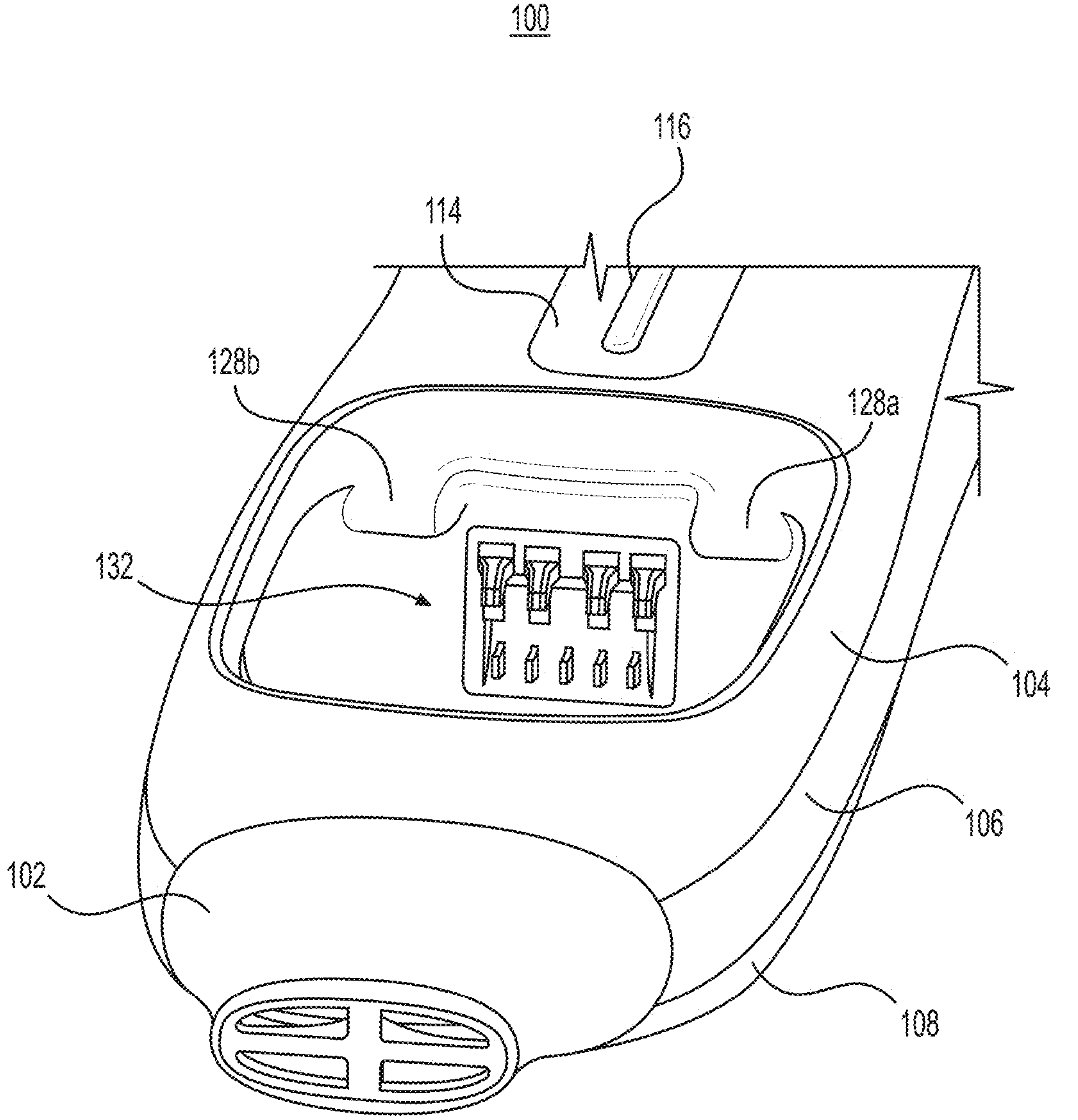
FIG. 12 is an enlarged perspective view of the device electrical contacts in FIG. 10.

FIG. 12 is an enlarged perspective view of the device electrical contacts in FIG. 10. The device electrical contacts of the device body 100 are configured to engage with the pod electrical contacts of the non-nicotine pod assembly 300 when the non-nicotine pod assembly 300 is seated within the through hole 150 of the device body 100. Referring to FIG. 12, the device electrical contacts of the device body 100 include the device electrical connector 132. The device electrical connector 132 includes power contacts and data contacts. The power contacts of the device electrical connector 132 are configured to supply power from the device body 100 to the non-nicotine pod assembly 300. As illustrated, the power contacts of the device electrical connector 132 include a first pair of power contacts and a second pair of power contacts (which are positioned so as to be closer to the front cover 104 than the rear cover 108). The first pair of power contacts (e.g., the pair adjacent to the first upstream protrusion 128*a*) may be a single integral structure that is distinct from the second pair of power contacts and that, when assembled, includes two projections that extend into the through hole 150. Similarly, the second pair of power contacts (e.g., the pair adjacent to the second upstream protrusion **128*b*) may be a single integral structure that is distinct from the first pair of power contacts and that, when assembled, includes two projections that extend into the through hole 150. The first pair of power contacts and the second pair of power contacts of the device electrical connector 132 may be tractably-mounted and biased so as to protract into the through hole 150 as a default and to retract (e.g., independently) from the through hole 150** when subjected to a force that overcomes the bias.

The data contacts of the device electrical connector 132 are configured to transmit data between a non-nicotine pod assembly 300 and the device body 100. As illustrated, the data contacts of the device electrical connector 132 include a row of five projections (which are positioned so as to be closer to the rear cover 108 than the front cover 104). The data contacts of the device electrical connector 132 may be distinct structures that, when assembled, extend into the through hole 150. The data contacts of the device electrical connector 132 may also be tractably-mounted and biased (e.g., with springs) so as to protract into the through hole 150 as a default and to retract (e.g., independently) from the through hole 150 when subjected to a force that overcomes the bias. For instance, when a non-nicotine pod assembly 300 is inserted into the through hole 150 of the device body 100, the pod electrical contacts of the non-nicotine pod assembly 300 will press against the corresponding device electrical contacts of the device body 100. As a result, the power contacts and the data contacts of the device electrical connector 132 will be retracted (e.g., at least partially retracted) into the device body 100 but will continue to push against the corresponding pod electrical contacts due to their resilient arrangement, thereby helping to ensure a proper electrical connection between the device body 100 and the non-nicotine pod assembly 300. Furthermore, such a connection may also be mechanically secure and have minimal contact resistance so as to allow power and/or signals between the device body 100 and the non-nicotine pod assembly 300 to be transferred and/or communicated reliably and accurately. While various aspects have been discussed in connection with the device electrical contacts of the device body 100, it should be understood that example embodiments are not limited thereto and that other configurations may be utilized.

Figure 13:
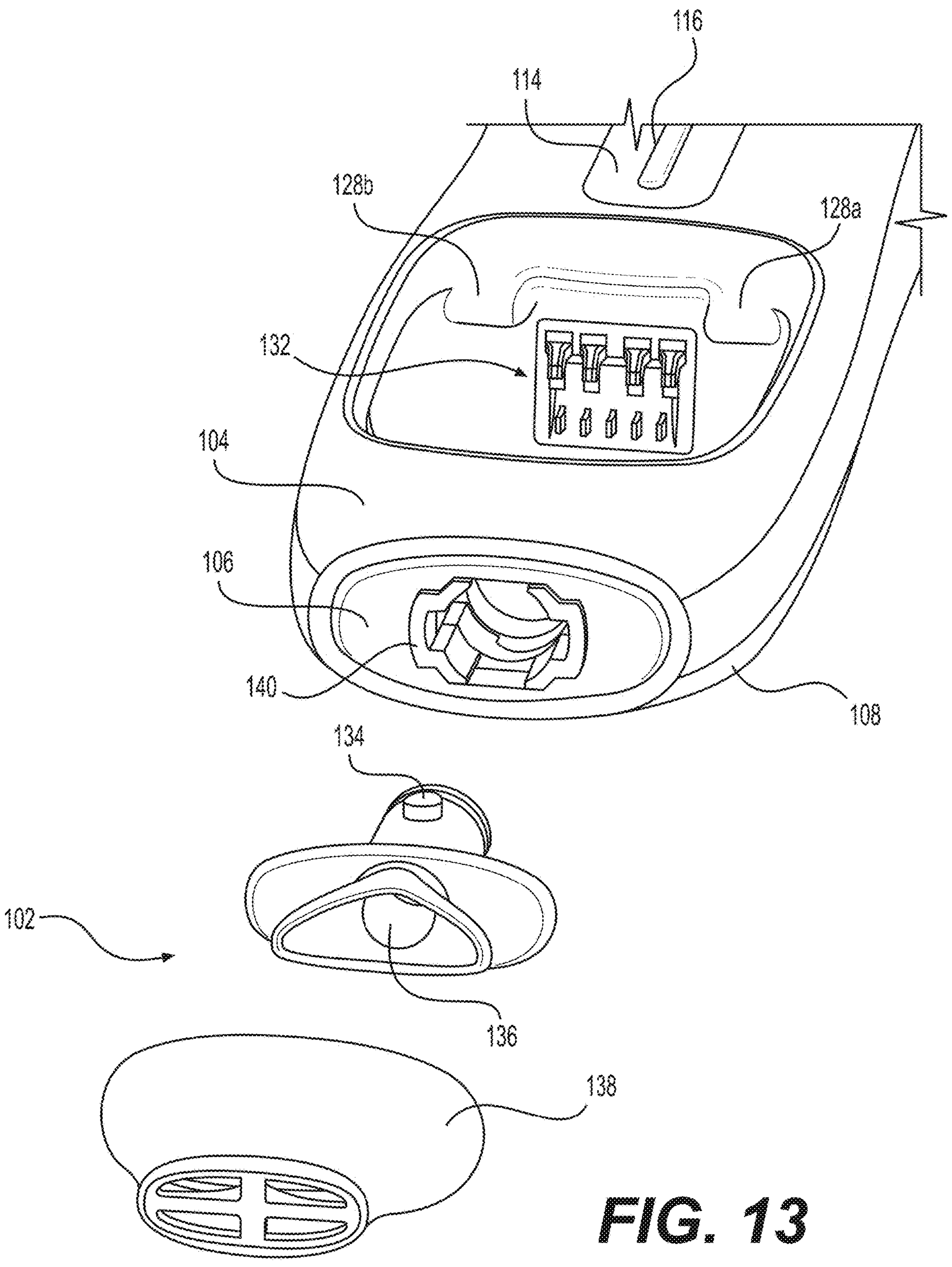
FIG. 13 is a partially exploded view involving the mouthpiece in FIG. 12.

FIG. 13 is a partially exploded view involving the mouthpiece in FIG. 12. Referring to FIG. 13, the mouthpiece 102 is configured to engage with the device housing via a retention structure 140. In an example embodiment, the retention structure 140 is situated so as to be primarily between the frame 106 and the bezel structure 112. As shown, the retention structure 140 is disposed within the device housing such that the proximal end of the retention structure 140 extends through the proximal end of the frame 106. The retention structure 140 may extend slightly beyond the proximal end of the frame 106 or be substantially even therewith. The proximal end of the retention structure 140 is configured to receive a distal end of the mouthpiece 102. The proximal end of the retention structure 140 may be a female end, while the distal end of the mouthpiece may be a male end.

For instance, the mouthpiece 102 may be coupled (e.g., reversibly coupled) to the retention structure 140 with a bayonet connection. In such an instance, the female end of the retention structure 140 may define a pair of opposing L-shaped slots, while the male end of the mouthpiece 102 may have opposing radial members 134 (e.g., radial pins) configured to engage with the L-shaped slots of the retention structure 140. Each of the L-shaped slots of the retention structure 140 have a longitudinal portion and a circumferential portion. Optionally, the terminus of the circumferential portion may have a serif portion to help reduce or prevent the likelihood that that a radial member 134 of the mouthpiece 102 will inadvertently become disengaged. In a non-limiting embodiment, the longitudinal portions of the L-shaped slots extend in parallel and along a longitudinal axis of the device body 100, while the circumferential portions of the L-shaped slots extend around the longitudinal axis (e.g., central axis) of the device body 100. As a result, to couple the mouthpiece 102 to the device housing, the mouthpiece 102 shown in FIG. 13 is initially rotated 90 degrees to align the radial members 134 with the entrances to the longitudinal portions of the L-shaped slots of the retention structure 140. The mouthpiece 102 is then pushed into the retention structure 140 such that the radial members 134 slide along the longitudinal portions of the L-shaped slots until the junction with each of the circumferential portions is reached. At this point, the mouthpiece 102 is then rotated such that the radial members 134 travel across the circumferential portions until the terminus of each is reached. Where a serif portion is present at each terminus, a haptic and/or auditory feedback (e.g., audible click) may be produced to notify an adult vaper that the mouthpiece 102 has been properly coupled to the device housing.

The mouthpiece 102 defines a vapor passage 136 through which non-nicotine vapor flows during vaping. The vapor passage 136 is in fluidic communication with the through hole 150 (which is where the non-nicotine pod assembly 300 is seated within the device body 100). The proximal end of the vapor passage 136 may include a flared portion. In addition, the mouthpiece 102 may include an end cover 138. The end cover 138 may taper from its distal end to its proximal end. The outlet face of the end cover 138 defines a plurality of vapor outlets. Although four vapor outlets are shown in the end cover 138, it should be understood that example embodiments are not limited thereto.

Figure 14:
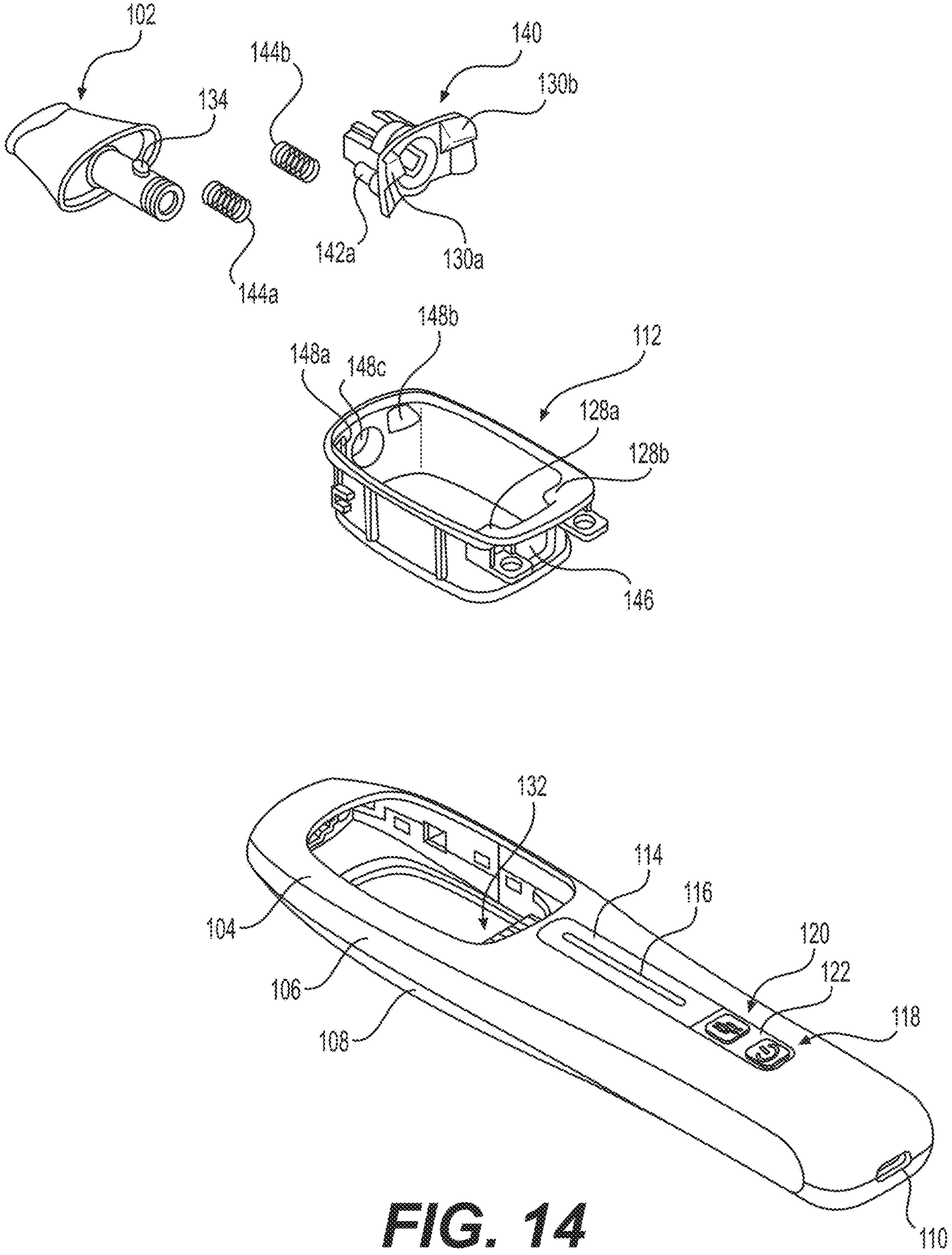
FIG. 14 is a partially exploded view involving the bezel structure in FIG. 9.
Figure 15:
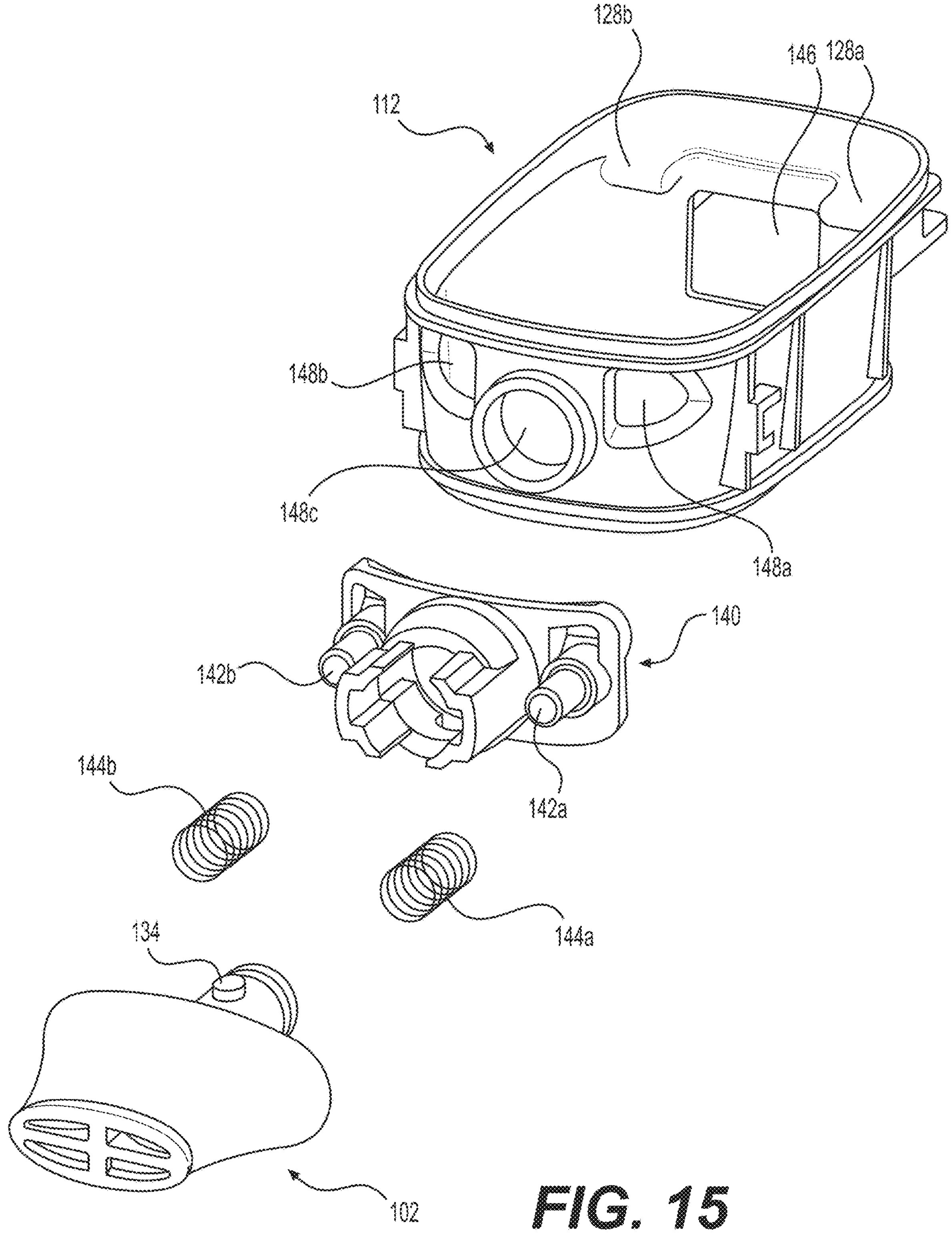
FIG. 15 is an enlarged perspective view of the mouthpiece, springs, retention structure, and bezel structure in FIG. 14.

FIG. 14 is a partially exploded view involving the bezel structure in FIG. 9. FIG. 15 is an enlarged perspective view of the mouthpiece, springs, retention structure, and bezel structure in FIG. 14. Referring to FIGS. 14-15, the bezel structure 112 includes an upstream sidewall and a downstream sidewall. The upstream sidewall of the bezel structure 112 defines a connector opening 146. The connector opening 146 is configured to expose or receive the device electrical connector 132 of the device body 100. The downstream sidewall of the bezel structure 112 defines a first downstream opening **148*a*, a second downstream opening 148*b*, and a third downstream opening 148*c*. The first downstream opening 148*a* and the second downstream opening 148*b* of the bezel structure 112 are configured to receive the first downstream protrusion 130*a* and the second downstream protrusion 130*b*, respectively, of the retention structure 140. The third downstream opening 148*c* of the bezel structure 112 is configured to receive the distal end of the mouthpiece 102**.

As shown in FIG. 14, the first downstream protrusion **130*a* and the second downstream protrusion 130*b* are on the concave side of the retention structure 140. As shown in FIG. 15, a first post 142*a* and a second post 142*b* are on the opposing convex side of the retention structure 140. A first spring 144*a* and a second spring 144*b* are disposed on the first post 142*a* and the second post 142*b*, respectively. The first spring 144*a* and the second spring 144*b* are configured to bias the retention structure 140 against the bezel structure 112**.

When assembled, the bezel structure 112 may be secured to the frame 106 via a pair of tabs adjacent to the connector opening 146. In addition, the retention structure 140 will abut the bezel structure 112 such that the first downstream protrusion 130*a* and the second downstream protrusion 130*b* extend through the first downstream opening 148*a* and the second downstream opening 148*b*, respectively. The mouthpiece 102 will be coupled to the retention structure 140 such that the distal end of the mouthpiece 102 extends through the retention structure 140 as well as the third downstream opening 148*c* of the bezel structure 112. The first spring 144*a* and the second spring 144*b* will be between the frame 106 and the retention structure 140.

When a non-nicotine pod assembly 300 is being inserted into the through hole 150 of the device body 100, the downstream end of the non-nicotine pod assembly 300 will push against the first downstream protrusion 130*a* and the second downstream protrusion 130*b* of the retention structure 140. As a result, the first downstream protrusion 130*a* and the second downstream protrusion 130*b* of the retention structure 140 will resiliently yield and retract from the through hole 150 of the device body 100 (by virtue of compression of the first spring 144*a* and the second spring 144*b*), thereby allowing the insertion of the non-nicotine pod assembly 300 to proceed. In an example embodiment, when the first downstream protrusion 130*a* and the second downstream protrusion 130*b* are fully retracted from the through hole 150 of the device body 100, the displacement of the retention structure 140 may cause the ends of the first post 142*a* and the second post 142*b* to contact the inner end surface of the frame 106. Furthermore, because the mouthpiece 102 is coupled to the retention structure 140, the distal end of the mouthpiece 102 will retract from the through hole 150, thus causing the proximal end of the mouthpiece 102 (e.g., visible portion including the end cover 138) to also shift by a corresponding distance away from the device housing.

Once the non-nicotine pod assembly 300 is adequately inserted such that the first downstream recess and the second downstream recess of the non-nicotine pod assembly 300 reach a position that allows an engagement with the first downstream protrusion 130*a* and the second downstream protrusion 130*b*, respectively, the stored energy from the compression of the first spring 144*a* and the second spring 144*b* will cause the first downstream protrusion 130*a* and the second downstream protrusion 130*b* to resiliently protract and engage with the first downstream recess and the second downstream recess, respectively, of the non-nicotine pod assembly 300. Furthermore, the engagement may produce a haptic and/or auditory feedback (e.g., audible click) to notify an adult vaper that the non-nicotine pod assembly 300 is properly seated within the through hole 150 of the device body 100.

Figure 16:
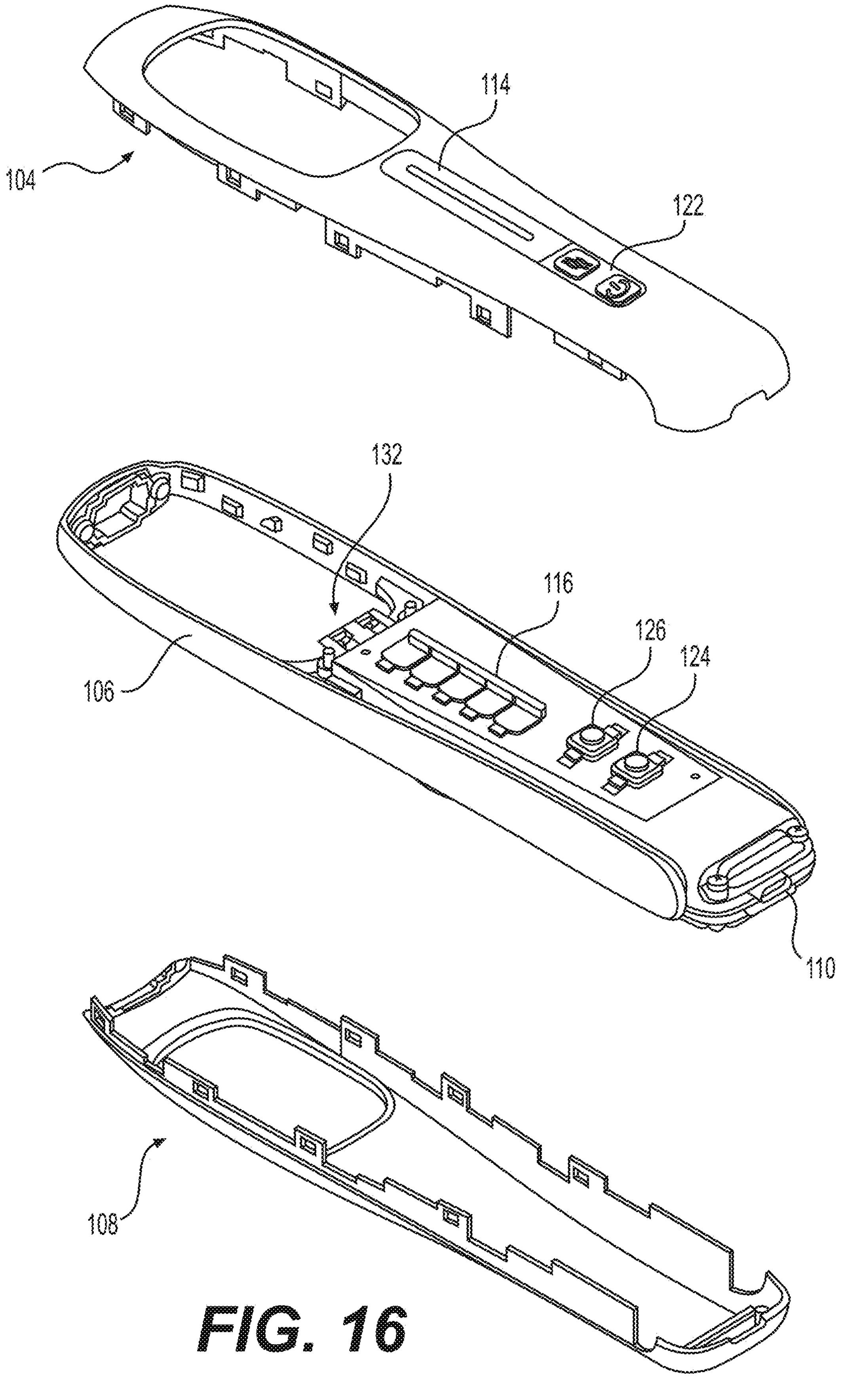
FIG. 16 is a partially exploded view involving the front cover, the frame, and the rear cover in FIG. 14.

FIG. 16 is a partially exploded view involving the front cover, the frame, and the rear cover in FIG. 14. Referring to FIG. 16, various mechanical elements, electronic elements, and/or circuitry associated with the operation of the non-nicotine e-vaping device 500 may be secured to the frame 106. The front cover 104 and the rear cover 108 may be configured to engage with the frame 106 via a snap-fit arrangement. In an example embodiment, the front cover 104 and the rear cover 108 include clips configured to interlock with corresponding mating members of the frame 106. The clips may be in a form of tabs with orifices configured to receive the corresponding mating members (e.g., protrusions with beveled edges) of the frame 106. In FIG. 16, the front cover 104 has two rows with four clips each (for a total of eight clips for the front cover 104). Similarly, the rear cover 108 has two rows with four clips each (for a total of eight clips for the rear cover 108). The corresponding mating members of the frame 106 may on the inner sidewalls of the frame 106. As a result, the engaged clips and mating members may be hidden from view when the front cover 104 and the rear cover 108 are snapped together. Alternatively, the front cover 104 and/or the rear cover 108 may be configured to engage with the frame 106 via an interference fit. However, it should be understood that the front cover 104, the frame 106, and the rear cover 108 may be coupled via other suitable arrangements and techniques.

Figure 17:
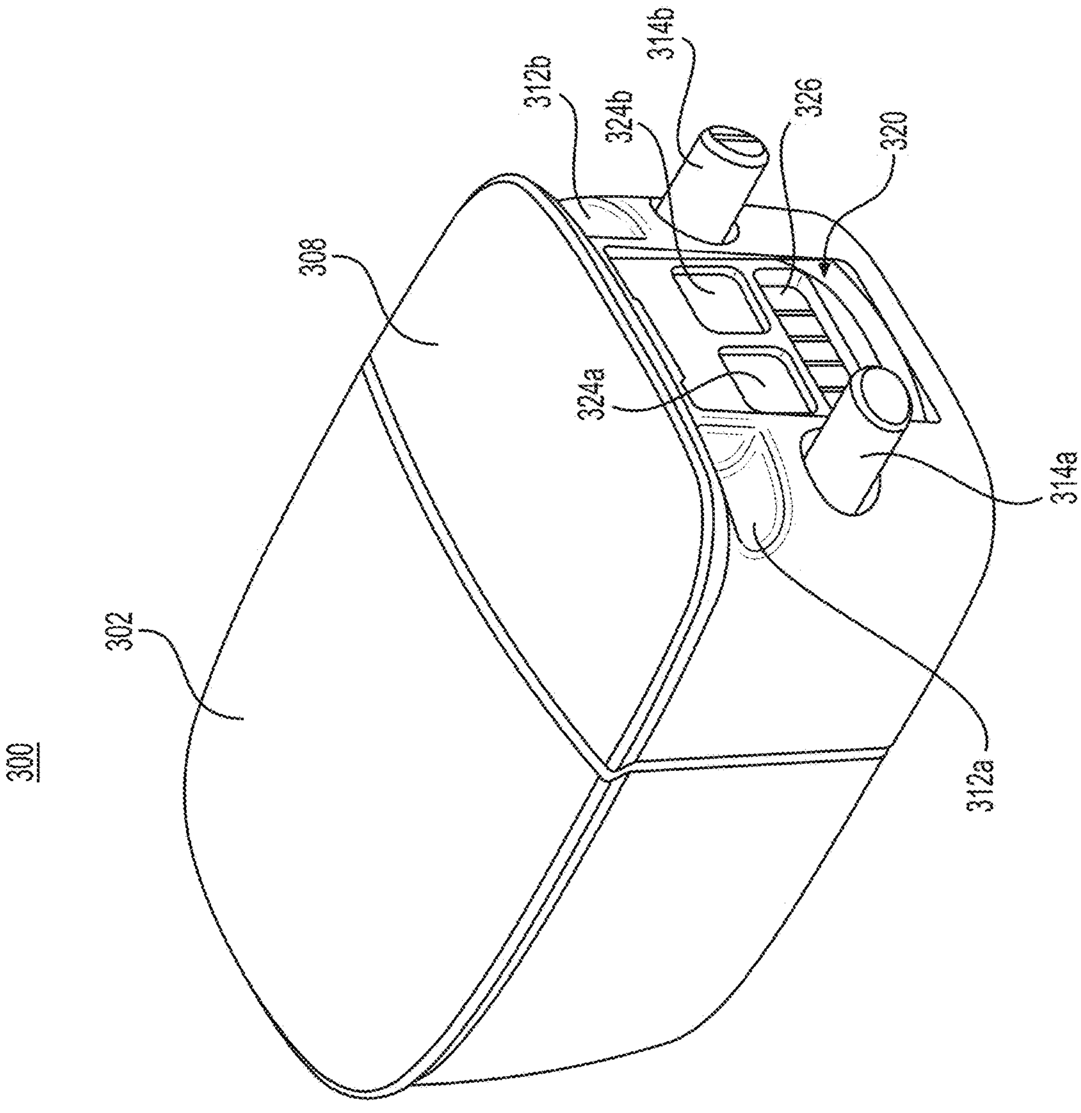
FIG. 17 is a perspective view of the non-nicotine pod assembly of the non-nicotine e-vaping device in FIG. 6.
Figure 18:
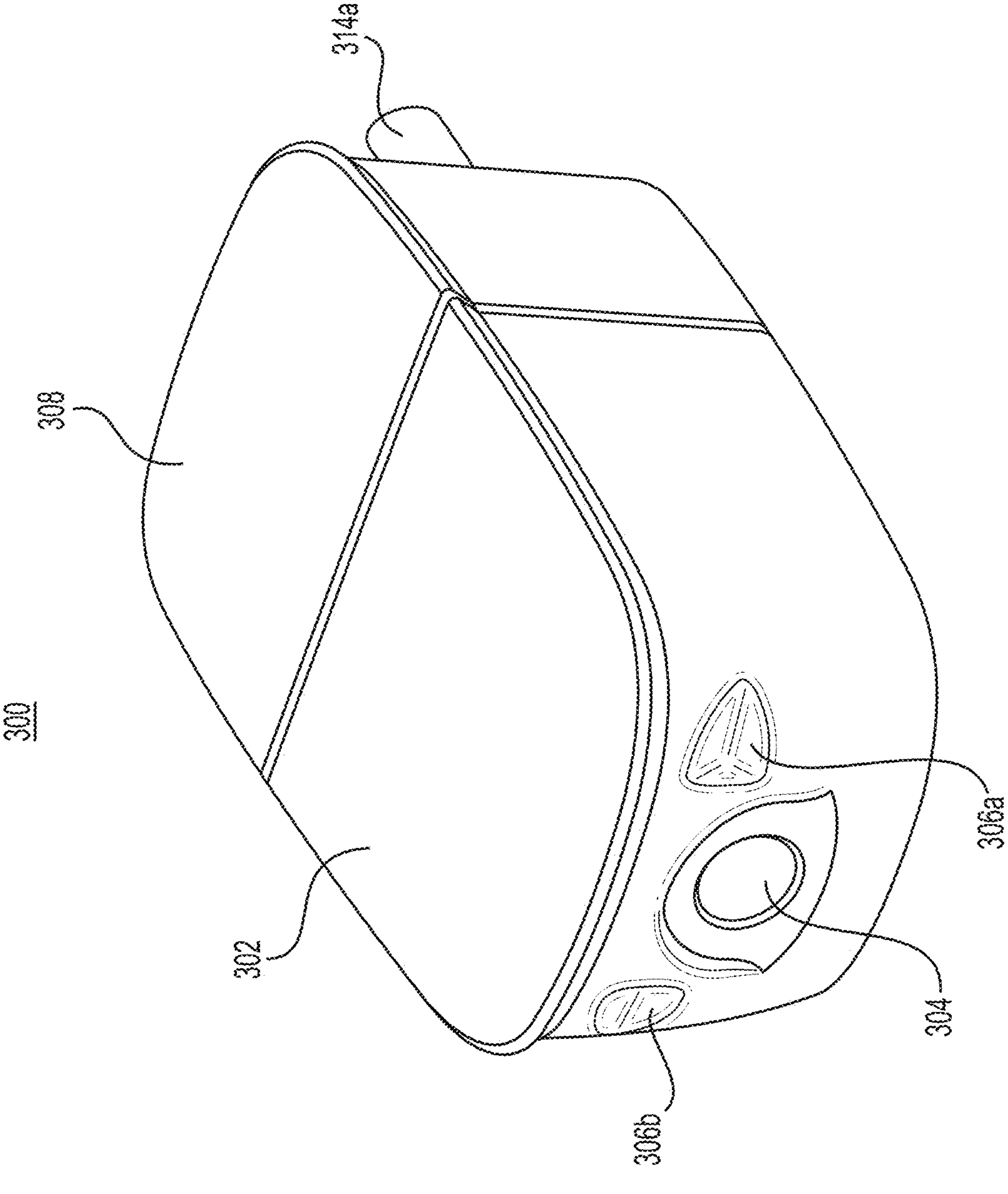
FIG. 18 is another perspective view of the non-nicotine pod assembly of FIG. 17.
Figure 19:
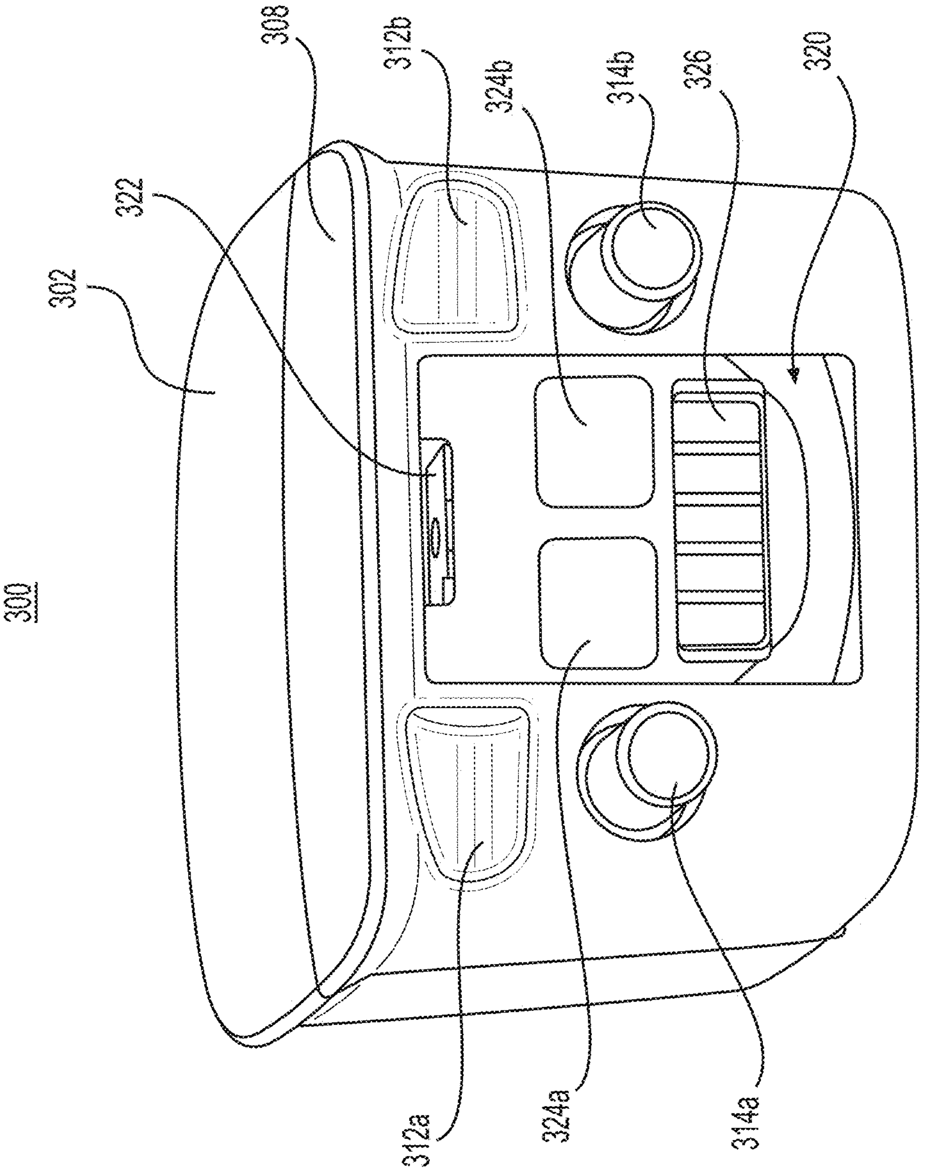
FIG. 19 is another perspective view of the non-nicotine pod assembly of FIG. 18.
Figure 20:
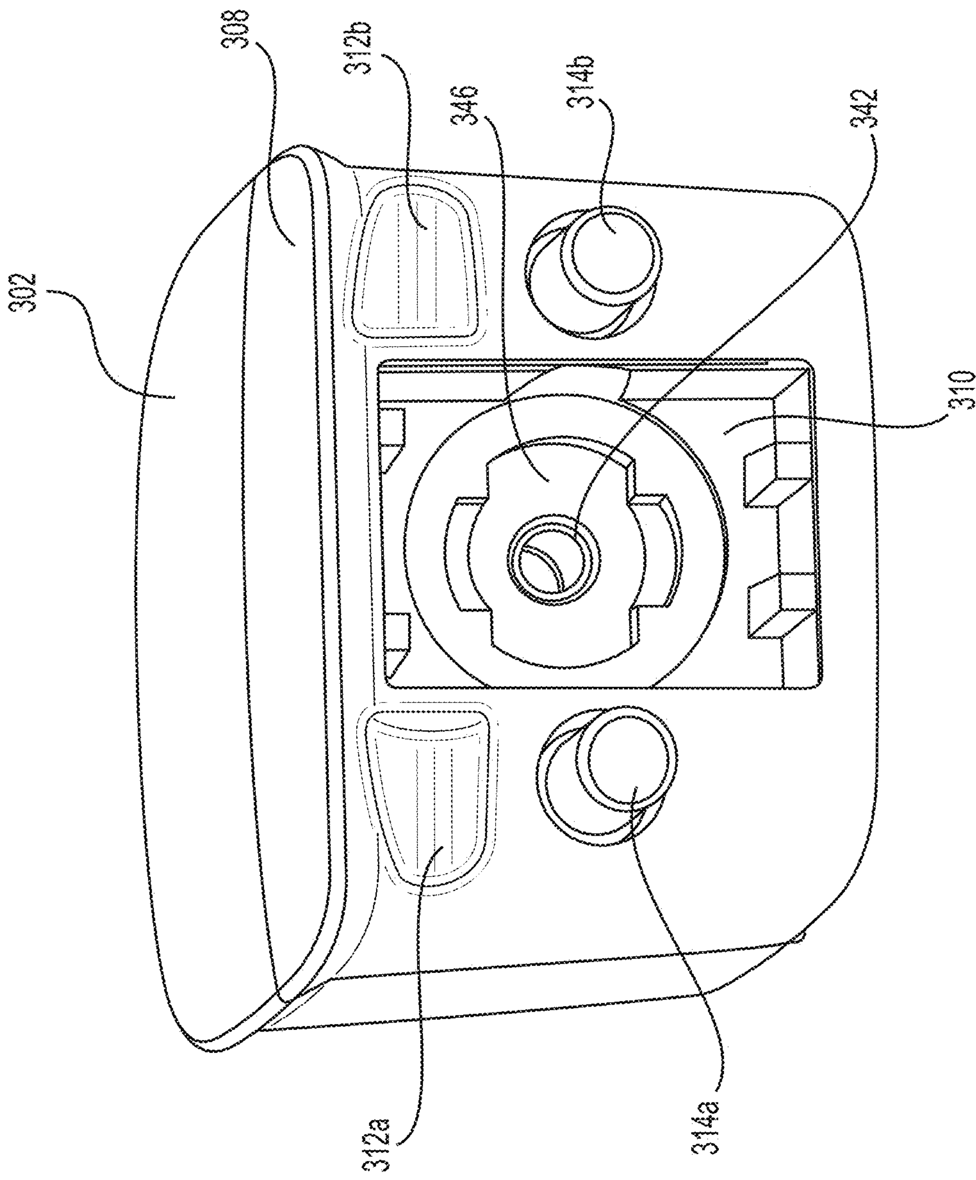
FIG. 20 is a perspective view of the non-nicotine pod assembly of FIG. 19 without the connector module.

FIG. 17 is a perspective view of the non-nicotine pod assembly of the non-nicotine e-vaping device in FIG. 6. FIG. 18 is another perspective view of the non-nicotine pod assembly of FIG. 17. FIG. 19 is another perspective view of the non-nicotine pod assembly of FIG. 18. Referring to FIGS. 17-19, the non-nicotine pod assembly 300 for the non-nicotine e-vaping device 500 includes a pod body configured to hold a non-nicotine pre-vapor formulation. The pod body has an upstream end and a downstream end. The upstream end of the pod body defines a cavity 310 (FIG. 20). The downstream end of the pod body defines a pod outlet 304 that is in fluidic communication with the cavity 310 at the upstream end. A connector module 320 is configured to be seated within the cavity 310 of the pod body. The connector module 320 includes an external face and a side face. The external face of the connector module 320 forms an exterior of the pod body.

The external face of the connector module 320 defines a pod inlet 322. The pod inlet 322 (through which air enters during vaping) is in fluidic communication with the pod outlet 304 (through which non-nicotine vapor exits during vaping). The pod inlet 322 is shown in FIG. 19 as being in a form of a slot. However, it should be understood that example embodiments are not limited thereto and that other forms are possible. When the connector module 320 is seated within the cavity 310 of the pod body, the external face of the connector module 320 remains visible, while the side face of the connector module 320 becomes mostly obscured so as to be only partially viewable through the pod inlet 322 based on a given angle.

The external face of the connector module 320 includes at least one electrical contact. The at least one electrical contact may include a plurality of power contacts. For instance, the plurality of power contacts may include a first power contact 324*a* and a second power contact 324*b*. The first power contact 324*a* of the non-nicotine pod assembly 300 is configured to electrically connect with the first pair of power contacts (e.g., the pair adjacent to the first upstream protrusion 128*a* in FIG. 12) of the device electrical connector 132 of the device body 100. Similarly, the second power contact 324*b* of the non-nicotine pod assembly 300 is configured to electrically connect with the second pair of power contacts (e.g., the pair adjacent to the second upstream protrusion 128*b* in FIG. 12) of the device electrical connector 132 of the device body 100. In addition, the at least one electrical contact of the non-nicotine pod assembly 300 includes a plurality of data contacts 326. The plurality of data contacts 326 of the non-nicotine pod assembly 300 are configured to electrically connect with the data contacts of the device electrical connector 132 (e.g., row of five projections in FIG. 12). While two power contacts and five data contacts are shown in connection with the non-nicotine pod assembly 300, it should be understood that other variations are possible depending on the design of the device body 100.

In an example embodiment, the non-nicotine pod assembly 300 includes a front face, a rear face opposite the front face, a first side face between the front face and the rear face, a second side face opposite the first side face, an upstream end face, and a downstream end face opposite the upstream end face. The corners of the side and end faces (e.g., corner of the first side face and the upstream end face, corner of upstream end face and the second side face, corner of the second side face and the downstream end face, corner of the downstream end face and the first side face) may be rounded. However, in some instances, the corners may be angular. In addition, the peripheral edge of the front face may be in a form of a ledge. The external face of the connector module 320 may be regarded as being part of the upstream end face of the non-nicotine pod assembly 300. The front face of the non-nicotine pod assembly 300 may be wider and longer than the rear face. In such an instance, the first side face and the second side face may be angled inwards towards each other. The upstream end face and the downstream end face may also be angled inwards towards each other. Because of the angled faces, the insertion of the non-nicotine pod assembly 300 will be unidirectional (e.g., from the front side (side associated with the front cover 104) of the device body 100). As a result, the possibility that the non-nicotine pod assembly 300 will be improperly inserted into the device body 100 can be reduced or prevented.

As illustrated, the pod body of the non-nicotine pod assembly 300 includes a first housing section 302 and a second housing section 308. The first housing section 302 has a downstream end defining the pod outlet 304. The rim of the pod outlet 304 may optionally be a sunken or indented region. In such an instance, this region may resemble a cove, wherein the side of the rim adjacent to the rear face of the non-nicotine pod assembly 300 may be open, while the side of the rim adjacent to the front face may be surrounded by a raised portion of the downstream end of the first housing section 302. The raised portion may function as a stopper for the distal end of the mouthpiece 102. As a result, this configuration for the pod outlet 304 may facilitate the receiving and aligning of the distal end of the mouthpiece 102 (e.g., FIG. 11) via the open side of the rim and its subsequent seating against the raised portion of the downstream end of the first housing section 302. In a non-limiting embodiment, the distal end of the mouthpiece 102 may also include (or be formed of) a resilient material to help create a seal around the pod outlet 304 when the non-nicotine pod assembly 300 is properly inserted within the through hole 150 of the device body 100.

The downstream end of the first housing section 302 additionally defines at least one downstream recess. In an example embodiment, the at least one downstream recess is in a form of a first downstream recess 306*a* and a second downstream recess 306*b*. The pod outlet 304 may be between the first downstream recess 306*a* and the second downstream recess 306*b*. The first downstream recess 306*a* and the second downstream recess 306*b* are configured to engage with the first downstream protrusion 130*a* and the second downstream protrusion 130*b*, respectively, of the device body 100. As shown in FIG. 11, the first downstream protrusion 130*a* and the second downstream protrusion 130*b* of the device body 100 may be disposed on adjacent corners of the downstream sidewall of the through hole 150. The first downstream recess 306*a* and the second downstream recess 306*b* may each be in a form of a V-shaped notch. In such an instance, each of the first downstream protrusion 130*a* and the second downstream protrusion 130*b* of the device body 100 may be in a form of a wedge-shaped structure configured to engage with a corresponding V-shaped notch of the first downstream recess 306*a* and the second downstream recess 306*b*. The first downstream recess 306*a* may abut the corner of the downstream end face and the first side face, while the second downstream recess 306*b* may abut the corner of the downstream end face and the second side face. As a result, the edges of the first downstream recess 306*a* and the second downstream recess 306*b* adjacent to the first side face and the second side face, respectively, may be open. In such an instance, as shown in FIG. 18, each of the first downstream recess 306*a* and the second downstream recess 306*b* may be a 3-sided recess.

Figure 21:
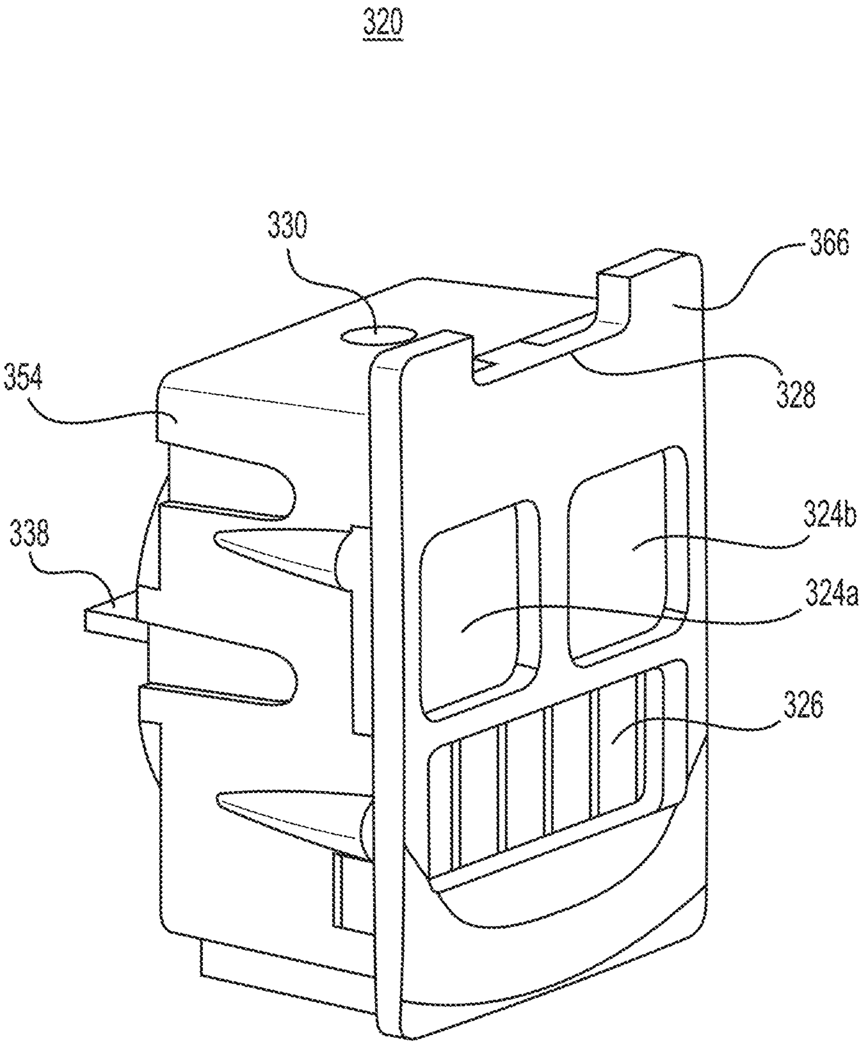
FIG. 21 is a perspective view of the connector module in FIG. 19.

The second housing section 308 has an upstream end defining the cavity 310 (FIG. 20). The cavity 310 is configured to receive the connector module 320 (FIG. 21). In addition, the upstream end of the second housing section 308 defines at least one upstream recess. In an example embodiment, the at least one upstream recess is in a form of a first upstream recess 312*a* and a second upstream recess 312*b*. The pod inlet 322 may be between the first upstream recess 312*a* and the second upstream recess 312*b*. The first upstream recess 312*a* and the second upstream recess 312*b* are configured to engage with the first upstream protrusion 128*a* and the second upstream protrusion 128*b*, respectively, of the device body 100. As shown in FIG. 12, the first upstream protrusion 128*a* and the second upstream protrusion 128*b* of the device body 100 may be disposed on adjacent corners of the upstream sidewall of the through hole 150. A depth of each of the first upstream recess 312*a* and the second upstream recess 312*b* may be greater than a depth of each of the first downstream recess 306*a* and the second downstream recess 306*b*. A terminus of each of the first upstream recess 312*a* and the second upstream recess 312*b* may also be more rounded than a terminus of each of the first downstream recess 306*a* and the second downstream recess 306*b*. For instance, the first upstream recess 312*a* and the second upstream recess 312*b* may each be in a form of a U-shaped indentation. In such an instance, each of the first upstream protrusion 128*a* and the second upstream protrusion 128*b* of the device body 100 may be in a form of a rounded knob configured to engage with a corresponding U-shaped indentation of the first upstream recess 312*a* and the second upstream recess 312*b*. The first upstream recess 312*a* may abut the corner of the upstream end face and the first side face, while the second upstream recess 312*b* may abut the corner of the upstream end face and the second side face. As a result, the edges of the first upstream recess 312*a* and the second upstream recess 312*b* adjacent to the first side face and the second side face, respectively, may be open.

The first housing section 302 may define a non-nicotine reservoir within configured to hold the non-nicotine pre-vapor formulation. The non-nicotine reservoir may be configured to hermetically seal the non-nicotine pre-vapor formulation until an activation of the non-nicotine pod assembly 300 to release the non-nicotine pre-vapor formulation from the non-nicotine reservoir. As a result of the hermetic seal, the non-nicotine pre-vapor formulation may be isolated from the environment as well as the internal elements of the non-nicotine pod assembly 300 that may potentially react with the non-nicotine pre-vapor formulation, thereby reducing or preventing the possibility of adverse effects to the shelf-life and/or sensorial characteristics (e.g., flavor) of the non-nicotine pre-vapor formulation. The second housing section 308 may contain structures configured to activate the non-nicotine pod assembly 300 and to receive and heat the non-nicotine pre-vapor formulation released from the non-nicotine reservoir after the activation.

The non-nicotine pod assembly 300 may be activated manually by an adult vaper prior to the insertion of the non-nicotine pod assembly 300 into the device body 100. Alternatively, the non-nicotine pod assembly 300 may be activated as part of the insertion of the non-nicotine pod assembly 300 into the device body 100. In an example embodiment, the second housing section 308 of the pod body includes a perforator configured to release the non-nicotine pre-vapor formulation from the non-nicotine reservoir during the activation of the non-nicotine pod assembly 300. The perforator may be in a form of a first activation pin 314*a* and a second activation pin 314*b*, which will be discussed in more detail herein.

To activate the non-nicotine pod assembly 300 manually, an adult vaper may press the first activation pin 314*a* and the second activation pin 314*b* inward (e.g., simultaneously or sequentially) prior to inserting the non-nicotine pod assembly 300 into the through hole 150 of the device body 100. For instance, the first activation pin 314*a* and the second activation pin 314*b* may be manually pressed until the ends thereof are substantially even with the upstream end face of the non-nicotine pod assembly 300. In an example embodiment, the inward movement of the first activation pin 314*a* and the second activation pin 314*b* causes a seal of the non-nicotine reservoir to be punctured or otherwise compromised so as to release the non-nicotine pre-vapor formulation therefrom.

Alternatively, to activate the non-nicotine pod assembly 300 as part of the insertion of the non-nicotine pod assembly 300 into the device body 100, the non-nicotine pod assembly 300 is initially positioned such that the first upstream recess 312*a* and the second upstream recess 312*b* are engaged with the first upstream protrusion 128*a* and the second upstream protrusion 128*b*, respectively (e.g., upstream engagement). Because each of the first upstream protrusion 128*a* and the second upstream protrusion 128*b* of the device body 100 may be in a form of a rounded knob configured to engage with a corresponding U-shaped indentation of the first upstream recess 312*a* and the second upstream recess 312*b*, the non-nicotine pod assembly 300 may be subsequently pivoted with relative ease about the first upstream protrusion 128*a* and the second upstream protrusion 128*b* and into the through hole 150 of the device body 100.

With regard to the pivoting of the non-nicotine pod assembly 300, the axis of rotation may be regarded as extending through the first upstream protrusion 128*a* and the second upstream protrusion 128*b* and oriented orthogonally to a longitudinal axis of the device body 100. During the initial positioning and subsequent pivoting of the non-nicotine pod assembly 300, the first activation pin 314*a* and the second activation pin 314*b* will come into contact with the upstream sidewall of the through hole 150 and transition from a protracted state to a retracted state as the first activation pin 314*a* and the second activation pin 314*b* are pushed (e.g., simultaneously) into the second housing section 308 as the non-nicotine pod assembly 300 progresses into the through hole 150. When the downstream end of the non-nicotine pod assembly 300 reaches the vicinity of the downstream sidewall of the through hole 150 and comes into contact with the first downstream protrusion 130*a* and the second downstream protrusion 130*b*, the first downstream protrusion 130*a* and the second downstream protrusion 130*b* will retract and then resiliently protract (e.g., spring back) when the positioning of the non-nicotine pod assembly 300 allows the first downstream protrusion 130*a* and the second downstream protrusion 130*b* of the device body 100 to engage with the first downstream recess 306*a* and the second downstream recess 306*b*, respectively, of the non-nicotine pod assembly 300 (e.g., downstream engagement).

As noted supra, according to an example embodiment, the mouthpiece 102 is secured to the retention structure 140 (of which the first downstream protrusion 130*a* and the second downstream protrusion 130*b* are a part). In such an instance, the retraction of the first downstream protrusion 130*a* and the second downstream protrusion 130*b* from the through hole 150 will cause a simultaneous shift of the mouthpiece 102 by a corresponding distance in the same direction (e.g., downstream direction). Conversely, the mouthpiece 102 will spring back simultaneously with the first downstream protrusion 130*a* and the second downstream protrusion 130*b* when the non-nicotine pod assembly 300 has been sufficiently inserted to facilitate downstream engagement. In addition to the resilient engagement by the first downstream protrusion 130*a* and the second downstream protrusion 130*b*, the distal end of the mouthpiece 102 is configured to also be biased against the non-nicotine pod assembly 300 (and aligned with the pod outlet 304 so as to form a relatively non-nicotine vapor-tight seal) when the non-nicotine pod assembly 300 is properly seated within the through hole 150 of the device body 100.

Furthermore, the downstream engagement may produce an audible click and/or a haptic feedback to indicate that the non-nicotine pod assembly 300 is properly seated within the through hole 150 of the device body 100. When properly seated, the non-nicotine pod assembly 300 will be connected to the device body 100 mechanically, electrically, and fluidically. Although the non-limiting embodiments herein describe the upstream engagement of the non-nicotine pod assembly 300 as occurring before the downstream engagement, it should be understood that the pertinent mating, activation, and/or electrical arrangements may be reversed such that the downstream engagement occurs before the upstream engagement.

FIG. 20 is a perspective view of the non-nicotine pod assembly of FIG. 19 without the connector module. Referring to FIG. 20, the upstream end of the second housing section 308 defines a cavity 310. As noted supra, the cavity 310 is configured to receive the connector module 320 (e.g., via interference fit). In an example embodiment, the cavity 310 is situated between the first upstream recess 312*a* and the second upstream recess 312*b* and also situated between the first activation pin 314*a* and the second activation pin 314*b*. In the absence of the connector module 320, an insert 342 (FIG. 24) and an absorbent material 346 (FIG. 25) are visible through a recessed opening in the cavity 310. The insert 342 is configured to retain the absorbent material 346. The absorbent material 346 is configured to absorb and hold a quantity of the non-nicotine pre-vapor formulation released from the non-nicotine reservoir when the non-nicotine pod assembly 300 is activated. The insert 342 and the absorbent material 346 will be discussed in more detail herein.

Figure 22:
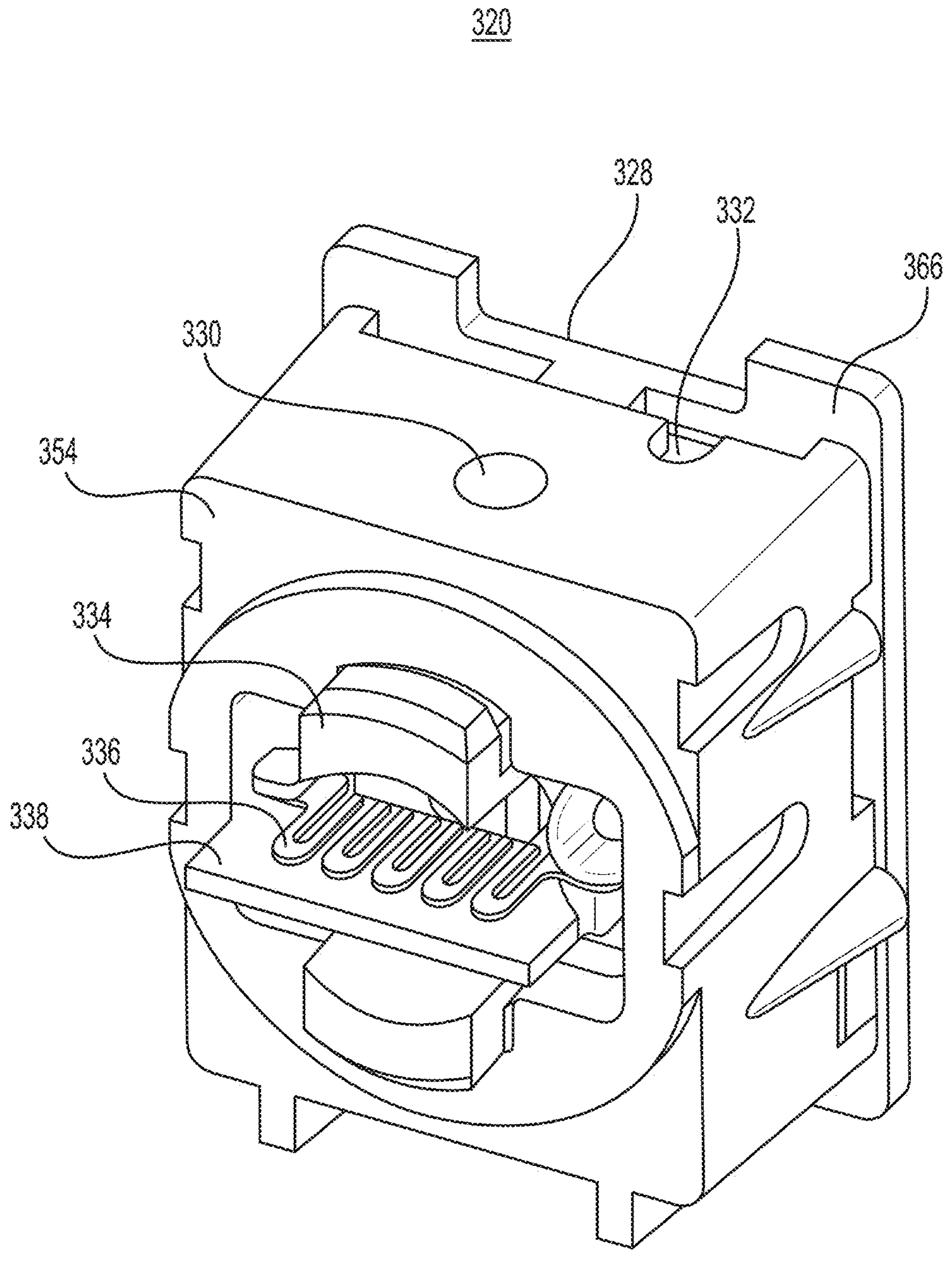
FIG. 22 is another perspective view of the connector module of FIG. 21.

FIG. 21 is a perspective view of the connector module in FIG. 19. FIG. 22 is another perspective view of the connector module of FIG. 21. Referring to FIGS. 21-22, the general framework of the connector module 320 includes a module housing 354 and a face plate 366. In addition, the connector module 320 has a plurality of faces, including an external face and a side face, wherein the external face is adjacent to the side face. In an example embodiment, the external face of the connector module 320 is composed of upstream surfaces of the face plate 366, the first power contact 324*a*, the second power contact 324*b*, and the data contacts 326. The side face of the connector module 320 is part of the module housing 354. The side face of the connector module 320 defines a first module inlet 330 and a second module inlet 332. Furthermore, the two lateral faces adjacent to the side face (which are also part of the module housing 354) may include rib structures (e.g., crush ribs) configured to facilitate an interference fit when the connector module 320 is seated within the cavity 310 of the pod body. For instance, each of the two lateral faces may include a pair of rib structures that taper away from the face plate 366. As a result, the module housing 354 will encounter increasing resistance via the friction of the rib structures against the lateral walls of the cavity 310 as the connector module 320 is pressed into the cavity 310 of the pod body. When the connector module 320 is seated within the cavity 310, the face plate 366 may be substantially flush with the upstream end of the second housing section 308. Also, the side face (which defines the first module inlet 330 and the second module inlet 332) of the connector module 320 will be facing a sidewall of the cavity 310.

The face plate 366 of the connector module 320 may have a grooved edge 328 that, in combination with a corresponding side surface of the cavity 310, defines the pod inlet 322. However, it should be understood that example embodiments are not limited thereto. For instance, the face plate 366 of the connector module 320 may be alternatively configured so as to entirely define the pod inlet 322. The side face (which defines the first module inlet 330 and the second module inlet 332) of the connector module 320 and the sidewall of the cavity 310 (which faces the side face) define an intermediate space in between. The intermediate space is downstream from the pod inlet 322 and upstream from the first module inlet 330 and the second module inlet 332. Thus, in an example embodiment, the pod inlet 322 is in fluidic communication with both the first module inlet 330 and the second module inlet 332 via the intermediate space. The first module inlet 330 may be larger than the second module inlet 332. In such an instance, when incoming air is received by the pod inlet 322 during vaping, the first module inlet 330 may receive a primary flow (e.g., larger flow) of the incoming air, while the second module inlet 332 may receive a secondary flow (e.g., smaller flow) of the incoming air.

As shown in FIG. 22, the connector module 320 includes a wick 338 that is configured to transfer a non-nicotine pre-vapor formulation to a heater 336. The heater 336 is configured to heat the non-nicotine pre-vapor formulation during vaping to generate a non-nicotine vapor. The heater 336 may be mounted in the connector module 320 via a contact core 334. The heater 336 is electrically connected to at least one electrical contact of the connector module 320. For instance, one end (e.g., first end) of the heater 336 may be connected to the first power contact 324*a*, while the other end (e.g., second end) of the heater 336 may be connected to the second power contact 324*b*. In an example embodiment, the heater 336 includes a folded heating element. In such an instance, the wick 338 may have a planar form configured to be held by the folded heating element. When the connector module 320 is seated within the cavity 310 of the pod body, the wick 338 is configured to be in fluidic communication with the absorbent material 346 such that the non-nicotine pre-vapor formulation that will be in the absorbent material 346 (when the non-nicotine pod assembly 300 is activated) will be transferred to the wick 338 via capillary action.

Figure 23:
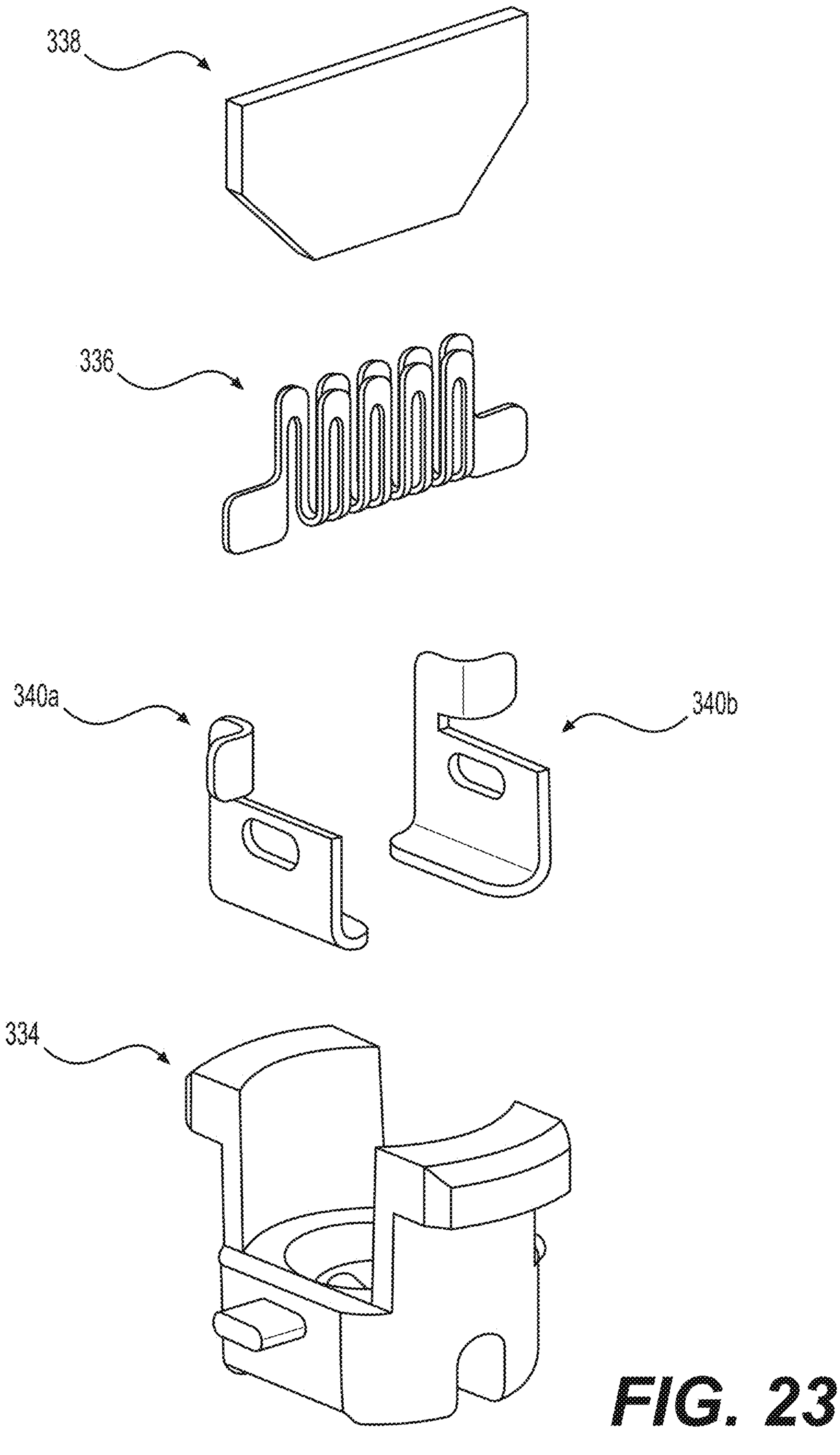
FIG. 23 is an exploded view involving the wick, heater, electrical leads, and contact core in FIG. 22.

FIG. 23 is an exploded view involving the wick, heater, electrical leads, and contact core in FIG. 22. Referring to FIG. 23, the wick 338 may be a fibrous pad or other structure with pores/interstices designed for capillary action. In addition, the wick 338 may have a shape of an irregular hexagon, although example embodiments are not limited thereto. The wick 338 may be fabricated into the hexagonal shape or cut from a larger sheet of material into this shape. Because the lower section of the wick 338 is tapered towards the winding section of the heater 336, the likelihood of the non-nicotine pre-vapor formulation being in a part of the wick 338 that continuously evades vaporization (due to its distance from the heater 336) can be reduced or avoided.

In an example embodiment, the heater 336 is configured to undergo Joule heating (which is also known as ohmic/resistive heating) upon the application of an electric current thereto. Stated in more detail, the heater 336 may be formed of one or more conductors and configured to produce heat when an electric current passes therethrough. The electric current may be supplied from a power source (e.g., battery) within the device body 100 and conveyed to the heater 336 via the first power contact 324*a* and the first electrical lead 340*a* (or via the second power contact 324*b* and the second electrical lead 340*b*).

Suitable conductors for the heater 336 include an iron-based alloy (e.g., stainless steel) and/or a nickel-based alloy (e.g., nichrome). The heater 336 may be fabricated from a conductive sheet (e.g., metal, alloy) that is stamped to cut a winding pattern therefrom. The winding pattern may have curved segments alternately arranged with horizontal segments so as to allow the horizontal segments to zigzag back and forth while extending in parallel. In addition, a width of each of the horizontal segments of the winding pattern may be substantially equal to a spacing between adjacent horizontal segments of the winding pattern, although example embodiments are not limited thereto. To obtain the form of the heater 336 shown in the drawings, the winding pattern may be folded so as to grip the wick 338.

The heater 336 may be secured to the contact core 334 with a first electrical lead 340*a* and a second electrical lead 340*b*. The contact core 334 is formed of an insulating material and configured to electrically isolate the first electrical lead 340*a* from the second electrical lead 340*b*. In an example embodiment, the first electrical lead 340*a* and the second electrical lead 340*b* each define a female aperture that is configured to engage with corresponding male members of the contact core 334. Once engaged, the first end and the second end of the heater 336 may be secured (e.g., welded, soldered, brazed) to the first electrical lead 340*a* and the second electrical lead 340*b*, respectively. The contact core 334 may then be seated within a corresponding socket in the module housing 354 (e.g., via interference fit). Upon completion of the assembly of the connector module 320, the first electrical lead 340*a* will electrically connect a first end of the heater 336 with the first power contact 324*a*, while the second electrical lead 340*b* will electrically connect a second end of the heater 336 with the second power contact 324*b*. The heater and associated structures are discussed in more detail in U.S. application Ser. No. 15/729,909, titled "Folded Heater For Electronic Vaping Device", filed Oct. 11, 2017, the entire contents of which is incorporated herein by reference.

Figure 24:
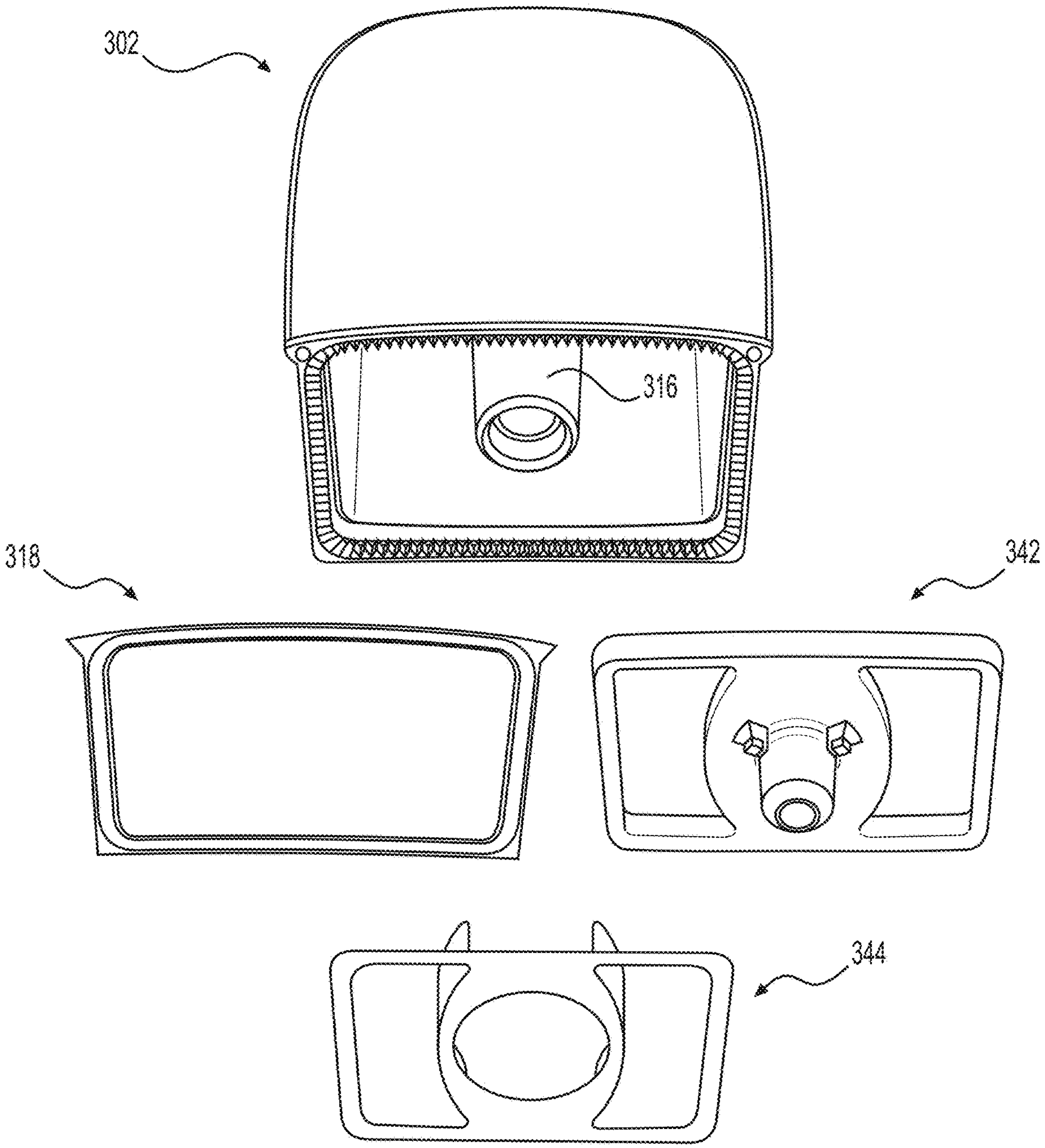
FIG. 24 is an exploded view involving the first housing section of the non-nicotine pod assembly of FIG. 17.

FIG. 24 is an exploded view involving the first housing section of the non-nicotine pod assembly of FIG. 17. Referring to FIG. 24, the first housing section 302 includes a vapor channel 316. The vapor channel 316 is configured to receive vapor generated by the heater 336 and is in fluidic communication with the pod outlet 304. In an example embodiment, the vapor channel 316 may gradually increase in size (e.g., diameter) as it extends towards the pod outlet 304. In addition, the vapor channel 316 may be integrally formed with the first housing section 302. A wrap 318, an insert 342, and a seal 344 are disposed at an upstream end of the first housing section 302 to define the non-nicotine reservoir of the non-nicotine pod assembly 300. For instance, the wrap 318 may be disposed on the rim of the first housing section 302. The insert 342 may be seated within the first housing section 302 such that the peripheral surface of the insert 342 engages with the inner surface of the first housing section 302 along the rim (e.g., via interference fit) such that the interface of the peripheral surface of the insert 342 and the inner surface of the first housing section 302 is fluid-tight (e.g., liquid-tight and/or air-tight). Furthermore, the seal 344 is attached to the upstream side of the insert 342 to close off the reservoir outlets in the insert 342 so as to provide a fluid-tight (e.g., liquid-tight and/or air-tight) containment of the non-nicotine pre-vapor formulation in the non-nicotine reservoir.

In an example embodiment, the insert 342 includes a holder portion that projects from the upstream side (as shown in FIG. 24) and a connector portion that projects from the downstream side (hidden from view in FIG. 24). The holder portion of the insert 342 is configured to hold the absorbent material 346, while the connector portion of the insert 342 is configured to engage with the vapor channel 316 of the first housing section 302. The connector portion of the insert 342 may be configured to be seated within the vapor channel 316 and, thus, engage the interior of the vapor channel 316. Alternatively, the connector portion of the insert 342 may be configured to receive the vapor channel 316 and, thus, engage with the exterior of the vapor channel 316. The insert 342 also defines reservoir outlets through which the non-nicotine pre-vapor formulation flows when the seal 344 is punctured (as shown in FIG. 24) during the activation of the non-nicotine pod assembly 300. The holder portion and the connector portion of the insert 342 may be between the reservoir outlets (e.g., first and second reservoir outlets), although example embodiments are not limited thereto. Furthermore, the insert 342 defines a vapor conduit extending through the holder portion and the connector portion. As a result, when the insert 342 is seated within the first housing section 302, the vapor conduit of the insert 342 will be aligned with and in fluidic communication with the vapor channel 316 so as to form a continuous path through the non-nicotine reservoir to the pod outlet 304 for the non-nicotine vapor generated by the heater 336 during vaping.

The seal 344 is attached to the upstream side of the insert 342 so as to cover the reservoir outlets in the insert 342. In an example embodiment, the seal 344 defines an opening (e.g., central opening) configured to provide the pertinent clearance to accommodate the holder portion (that projects from the upstream side of the insert 342) when the seal 344 is attached to the insert 342. In FIG. 24, it should be understood that the seal 344 is shown in a punctured state. In particular, when punctured by the first activation pin 314*a* and the second activation pin 314*b* of the non-nicotine pod assembly 300, the two punctured sections of the seal 344 will be pushed into the non-nicotine reservoir as flaps (as shown in FIG. 24), thus creating two punctured openings (e.g., one on each side of the central opening) in the seal 344. The size and shape of the punctured openings in the seal 344 may correspond to the size and shape of the reservoir outlets in the insert 342. In contrast, when in an unpunctured state, the seal 344 will have a planar form and only one opening (e.g., central opening). The seal 344 is designed to be strong enough to remain intact during the normal movement and/or handling of the non-nicotine pod assembly 300 so as to avoid being prematurely/inadvertently breached. For instance, the seal 344 may be a coated foil (e.g., aluminum-backed Tritan).

Figure 25:
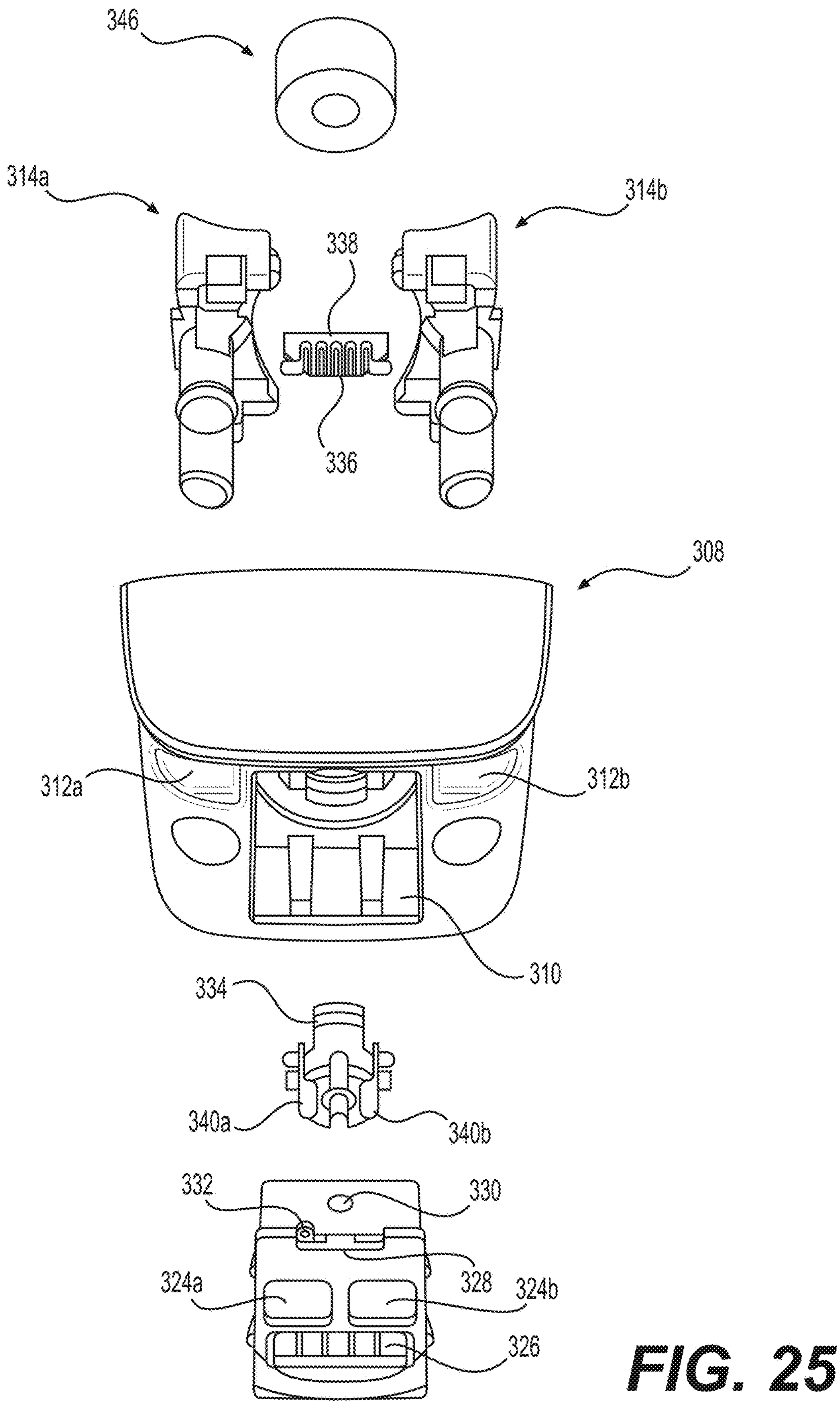
FIG. 25 is a partially exploded view involving the second housing section of the non-nicotine pod assembly of FIG. 17.

FIG. 25 is a partially exploded view involving the second housing section of the non-nicotine pod assembly of FIG. 17. Referring to FIG. 25, the second housing section 308 is structured to contain various elements configured to release, receive, and heat the non-nicotine pre-vapor formulation. For instance, the first activation pin 314*a* and the second activation pin 314*b* are configured to puncture the non-nicotine reservoir in the first housing section 302 to release the non-nicotine pre-vapor formulation. Each of the first activation pin 314*a* and the second activation pin 314*b* has a distal end that extends through corresponding openings in the second housing section 308. In an example embodiment, the distal ends of the first activation pin 314*a* and the second activation pin 314*b* are visible after assembly (e.g., FIG. 17), while the remainder of the first activation pin 314*a* and the second activation pin 314*b* are hidden from view within the non-nicotine pod assembly 300. In addition, each of the first activation pin 314*a* and the second activation pin 314*b* has a proximal end that is positioned so as to be adjacent to and upstream from the seal 344 prior to activation of the non-nicotine pod assembly 300. When the first activation pin 314*a* and the second activation pin 314*b* are pushed into the second housing section 308 to activate the non-nicotine pod assembly 300, the proximal end of each of the first activation pin 314*a* and the second activation pin 314*b* will advance through the insert 342 and, as a result, puncture the seal 344, which will release the non-nicotine pre-vapor formulation from the non-nicotine reservoir. The movement of the first activation pin 314*a* may be independent of the movement of the second activation pin 314*b* (and vice versa). The first activation pin 314*a* and the second activation pin 314*b* will be discussed in more detail herein.

The absorbent material 346 is configured to engage with the holder portion of the insert 342 (which, as shown in FIG. 24, projects from the upstream side of the insert 342). The absorbent material 346 may have an annular form, although example embodiments are not limited thereto. As depicted in FIG. 25, the absorbent material 346 may resemble a hollow cylinder. In such an instance, the outer diameter of the absorbent material 346 may be substantially equal to (or slightly larger than) the length of the wick 338. The inner diameter of the absorbent material 346 may be smaller than the average outer diameter of the holder portion of the insert 342 so as to result in an interference fit. To facilitate the engagement with the absorbent material 346, the tip of the holder portion of the insert 342 may be tapered. In addition, although hidden from view in FIG. 25, the downstream side of the second housing section 308 may define a concavity configured receive and support the absorbent material 346. An example of such a concavity may be a circular chamber that is in fluidic communication with and downstream from the cavity 310. The absorbent material 346 is configured to receive and hold a quantity of the non-nicotine pre-vapor formulation released from the non-nicotine reservoir when the non-nicotine pod assembly 300 is activated.

The wick 338 is positioned within the non-nicotine pod assembly 300 so as to be in fluidic communication with the absorbent material 346 such that the non-nicotine pre-vapor formulation can be drawn from the absorbent material 346 to the heater 336 via capillary action. The wick 338 may physically contact an upstream side of the absorbent material 346 (e.g., bottom of the absorbent material 346 based on the view shown in FIG. 25). In addition, the wick 338 may be aligned with a diameter of the absorbent material 346, although example embodiments are not limited thereto.

As illustrated in FIG. 25 (as well as previous FIG. 23), the heater 336 may have a folded configuration so as to grip and establish thermal contact with the opposing surfaces of the wick 338. The heater 336 is configured to heat the wick 338 during vaping to generate a non-nicotine. To facilitate such heating, the first end of the heater 336 may be electrically connected to the first power contact 324*a* via the first electrical lead 340*a*, while the second end of the heater 336 may be electrically connected to the second power contact 324*b* via the second electrical lead 340*b*. As a result, an electric current may be supplied from a power source (e.g., battery) within the device body 100 and conveyed to the heater 336 via the first power contact 324*a* and the first electrical lead 340*a* (or via the second power contact 324*b* and the second electrical lead 340*b*). The first electrical lead 340*a* and the second electrical lead 340*b* (which are shown separately in FIG. 23) may be engaged with the contact core 334 (as shown in FIG. 25). The relevant details of other aspects of the connector module 320, which is configured to be seated within the cavity 310 of the second housing section 308, that have been discussed supra (e.g., in connection with FIGS. 21-22) and will not be repeated in this section in the interest of brevity. During vaping, the non-nicotine generated by the heater 336 is drawn through the vapor conduit of the insert 342, through the vapor channel 316 of the first housing section 302, out the pod outlet 304 of the non-nicotine pod assembly 300, and through the vapor passage 136 of the mouthpiece 102 to the vapor outlet(s).

Figure 26:
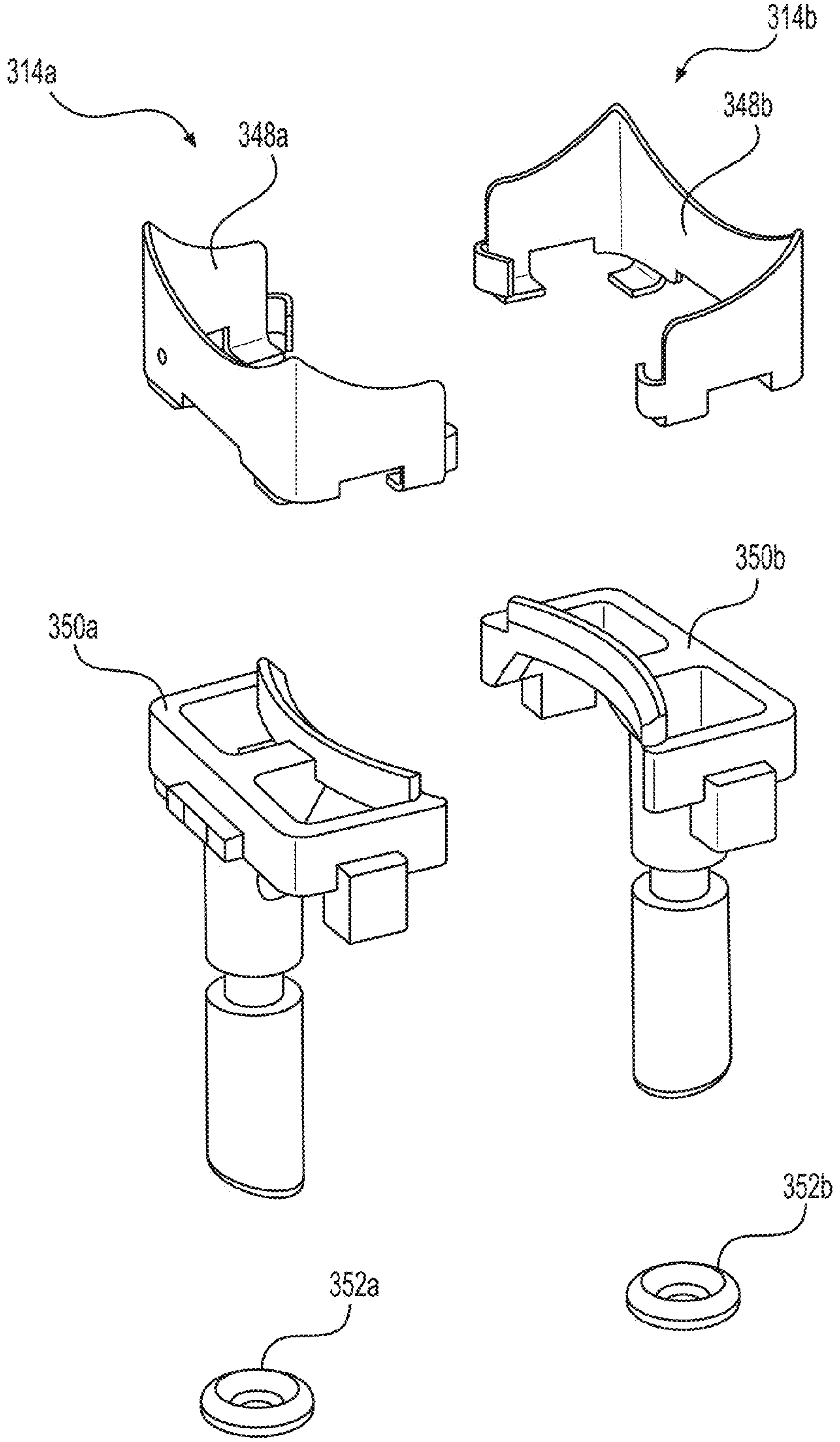
FIG. 26 is an exploded view of the activation pin in FIG. 25.

FIG. 26 is an exploded view of the activation pin in FIG. 25. Referring to FIG. 26, the activation pin may be in the form of a first activation pin 314*a* and a second activation pin 314*b*. While two activation pins are shown and discussed in connection with the non-limiting embodiments herein, it should be understood that, alternatively, the non-nicotine pod assembly 300 may include only one activation pin. In FIG. 26, the first activation pin 314*a* may include a first blade 348*a*, a first actuator 350*a*, and a first O-ring 352*a*. Similarly, the second activation pin 314*b* may include a second blade 348*b*, a second actuator 350*b*, and a second O-ring 352*b*.

In an example embodiment, the first blade 348*a* and the second blade 348*b* are configured to be mounted or attached to upper portions (e.g., proximal portions) of the first actuator 350*a* and the second actuator 350*b*, respectively. The mounting or attachment may be achieved via a snap-fit connection, an interference fit (e.g., friction fit) connection, an adhesive, or other suitable coupling technique. The top of each of the first blade 348*a* and the second blade 348*b* may have one or more curved or concave edges that taper upward to a pointed tip. For instance, each of the first blade 348*a* and the second blade 348*b* may have two pointed tips with a concave edge therebetween and a curved edge adjacent to each pointed tip. The radii of curvature of the concave edge and the curved edges may be the same, while their arc lengths may differ. The first blade 348*a* and the second blade 348*b* may be formed of a sheet metal (e.g., stainless steel) that is cut or otherwise shaped to have the desired profile and bent to its final form. In another instance, the first blade 348*a* and the second blade 348*b* may be formed of plastic.

Based on a plan view, the size and shape of the first blade 348*a*, the second blade 348*b*, and portions of the first actuator 350*a* and the second actuator 350*b* on which they are mounted may correspond to the size and shape of the reservoir outlets in the insert 342. Additionally, as shown in FIG. 26, the first actuator 350*a* and the second actuator 350*b* may include projecting edges (e.g., curved inner lips which face each other) configured to push the two punctured sections of the seal 344 into the non-nicotine reservoir as the first blade 348*a* and the second blade 348*b* advance into the non-nicotine reservoir. In a non-limiting embodiment, when the first activation pin 314*a* and the second activation pin 314*b* are fully inserted into the non-nicotine pod assembly 300, the two flaps (from the two punctured sections of the seal 344, as shown in FIG. 24) may be between the curved sidewalls of the reservoir outlets of the insert 342 and the corresponding curvatures of the projecting edges of the first actuator 350*a* and the second actuator 350*b*. As a result, the likelihood of the two punctured openings in the seal 344 becoming obstructed (by the two flaps from the two punctured sections) may be reduced or prevented. Furthermore, the first actuator 350*a* and the second actuator 350*b* may be configured to guide the non-nicotine pre-vapor formulation from the non-nicotine reservoir toward the absorbent material 346.

The lower portion (e.g., distal portion) of each of the first actuator 350*a* and the second actuator 350*b* is configured to extend through a bottom section (e.g., upstream end) of the second housing section 308. This rod-like portion of each of the first actuator 350*a* and the second actuator 350*b* may also be referred to as the shaft. The first O-ring 352*a* and the second O-ring 352*b* may be seated in annular grooves in the respective shafts of the first actuator 350*a* and the second actuator 350*b*. The first O-ring 352*a* and the second O-ring 352*b* are configured to engage with the shafts of the first actuator 350*a* and the second actuator 350*b* as well as the inner surfaces of the corresponding openings in the second housing section 308 in order to provide a fluid-tight seal. As a result, when the first activation pin 314*a* and the second activation pin 314*b* are pushed inward to activate the non-nicotine pod assembly 300, the first O-ring 352*a* and the second O-ring 352*b* may move together with the respective shafts of the first actuator 350*a* and the second actuator 350*b* within the corresponding openings in the second housing section 308 while maintaining their respective seals, thereby helping to reduce or prevent leakage of the non-nicotine pre-vapor formulation through the openings in the second housing section 308 for the first activation pin 314*a* and the second activation pin 314*b*. The first O-ring 352*a* and the second O-ring 352*b* may be formed of silicone.

Figure 27:
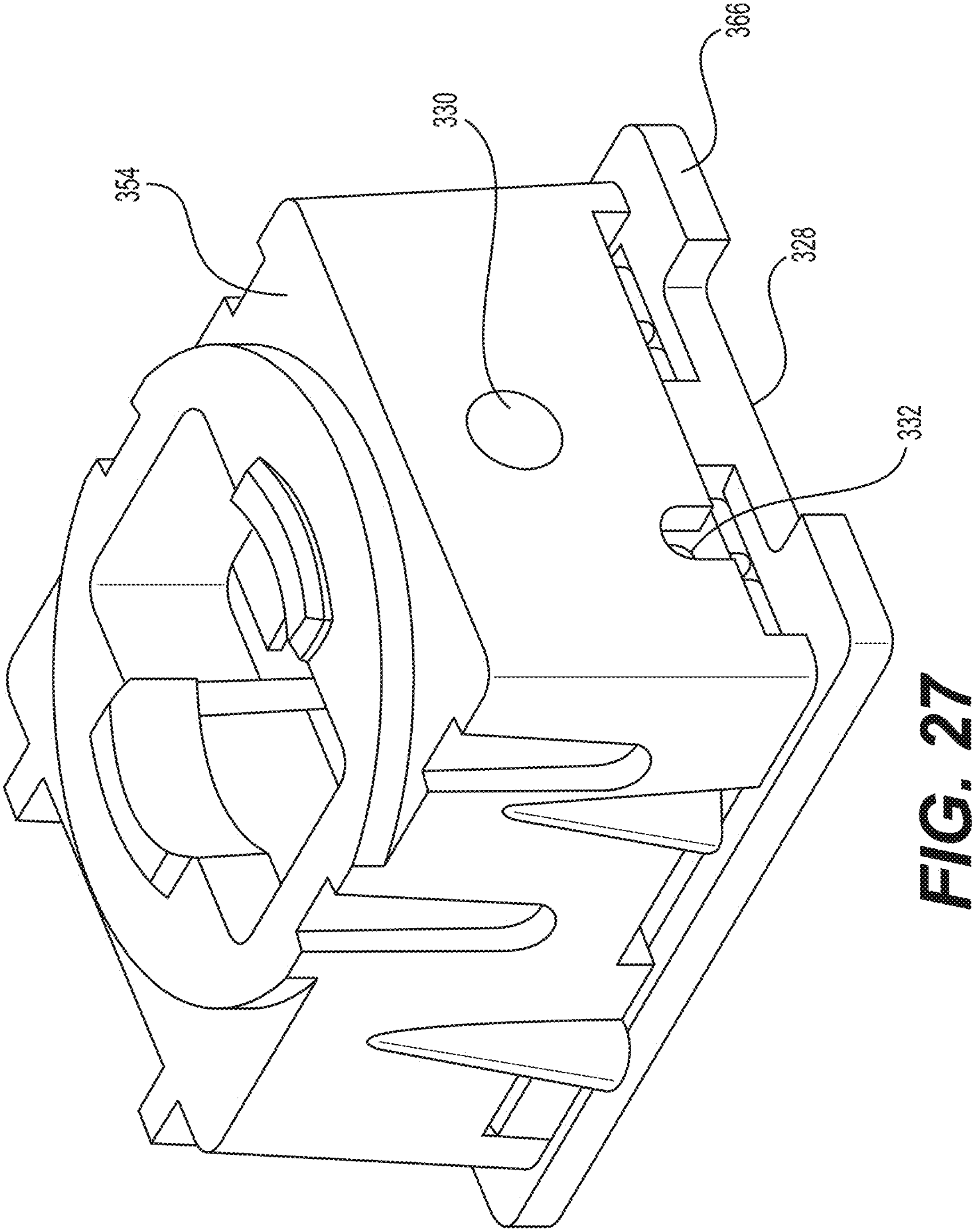
FIG. 27 is a perspective view of the connector module of FIG. 22 without the wick, heater, electrical leads, and contact core.
Figure 28:
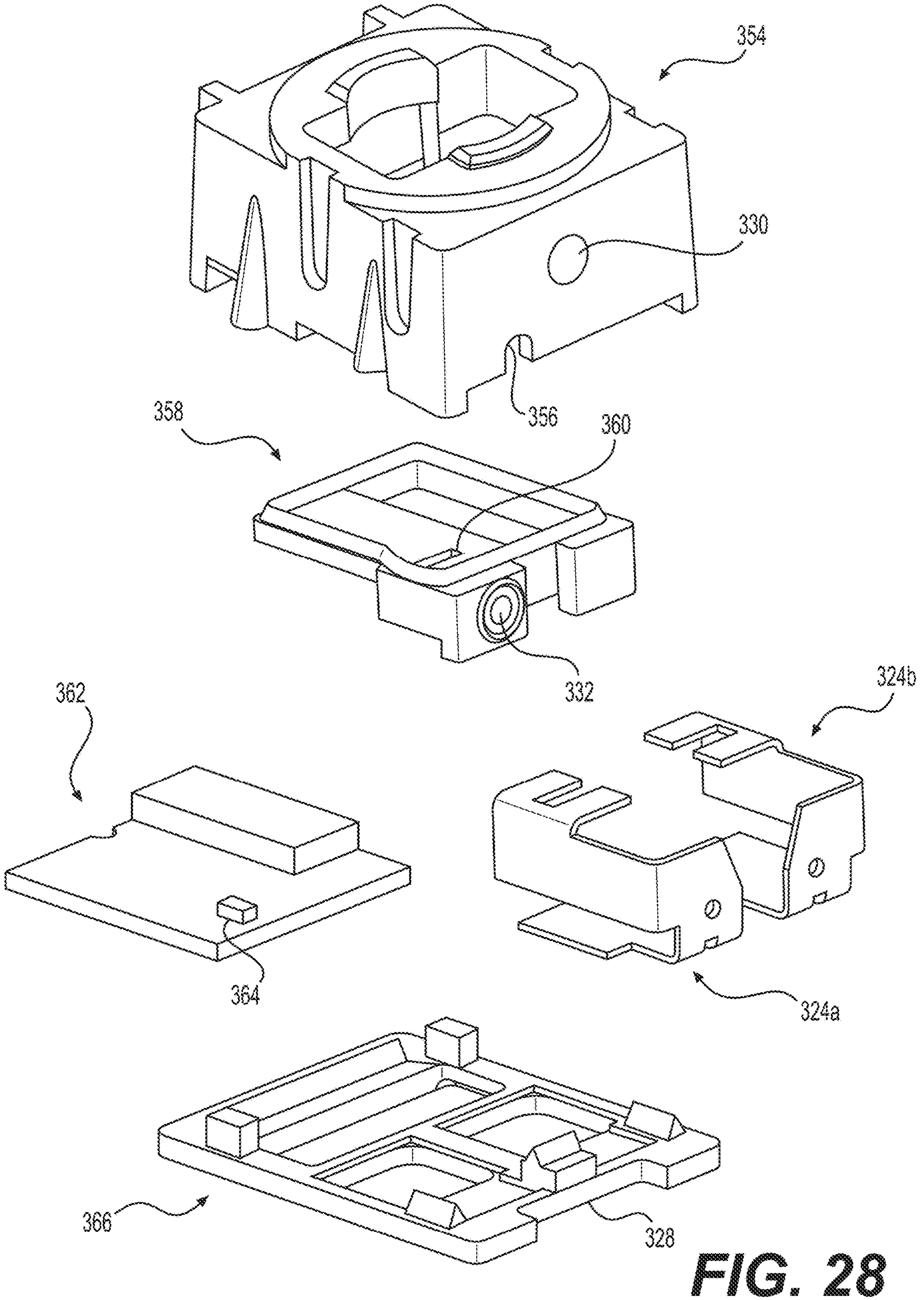
FIG. 28 is an exploded view of the connector module of FIG. 27.

FIG. 27 is a perspective view of the connector module of FIG. 22 without the wick, heater, electrical leads, and contact core. FIG. 28 is an exploded view of the connector module of FIG. 27. Referring to FIGS. 27-28, the module housing 354 and the face plate 366 generally form the exterior framework of the connector module 320. The module housing 354 defines the first module inlet 330 and a grooved edge 356. The grooved edge 356 of the module housing 354 exposes the second module inlet 332 (which is defined by the bypass structure 358). However, it should be understood that the grooved edge 356 may also be regarded as defining a module inlet (e.g., in combination with the face plate 366). The face plate 366 has a grooved edge 328 which, together with the corresponding side surface of the cavity 310 of the second housing section 308, defines the pod inlet 322. In addition, the face plate 366 defines a first contact opening, a second contact opening, and a third contact opening. The first contact opening and the second contact opening may be square-shaped and configured to expose the first power contact 324*a* and the second power contact 324*b*, respectively, while the third contact opening may be rectangular-shaped and configured to expose the plurality of data contacts 326, although example embodiments are not limited thereto.

The first power contact 324*a*, the second power contact 324*b*, a printed circuit board (PCB) 362, and the bypass structure 358 are disposed within the exterior framework formed by the module housing 354 and the face plate 366. The printed circuit board (PCB) 362 includes the plurality of data contacts 326 on its upstream side (which is hidden from view in FIG. 28) and a sensor 364 on its downstream side. The bypass structure 358 defines the second module inlet 332 and a bypass outlet 360.

During assembly, the first power contact 324*a* and the second power contact 324*b* are positioned so as to be visible through the first contact opening and the second contact opening, respectively, of the face plate 366. Additionally, the printed circuit board (PCB) 362 is positioned such that the plurality of data contacts 326 on its upstream side are visible through the third contact opening of the face plate 366. The printed circuit board (PCB) 362 may also overlap the rear surfaces of the first power contact 324*a* and the second power contact 324*b*. The bypass structure 358 is positioned on the printed circuit board (PCB) 362 such that the sensor 364 is within an air flow path defined by the second module inlet 332 and the bypass outlet 360. When assembled, the bypass structure 358 and the printed circuit board (PCB) 362 may be regarded as being surrounded on at least four sides by the meandering structures of the first power contact 324*a* and the second power contact 324*b*. In an example embodiment, the bifurcated ends of the first power contact 324*a* and the second power contact 324*b* are configured to electrically connect to the first electrical lead 340*a* and the second electrical lead 340*b*.

When incoming air is received by the pod inlet 322 during vaping, the first module inlet 330 may receive a primary flow (e.g., larger flow) of the incoming air, while the second module inlet 332 may receive a secondary flow (e.g., smaller flow) of the incoming air. The secondary flow of the incoming air may improve the sensitivity of the sensor 364. After exiting the bypass structure 358 through the bypass outlet 360, the secondary flow rejoins with the primary flow to form a combined flow that is drawn into and through the contact core 334 so as to encounter the heater 336 and the wick 338. In a non-limiting embodiment, the primary flow may be 60-95% (e.g., 80-90%) of the incoming air, while the secondary flow may be 5-40% (e.g., 10-20%) of the incoming air.

The first module inlet 330 may be a resistance-to-draw (RTD) port, while the second module inlet 332 may be a bypass port. In such a configuration, the resistance-to-draw for the non-nicotine e-vaping device 500 may be adjusted by changing the size of the first module inlet 330 (rather than changing the size of the pod inlet 322). In an example embodiment, the size of the first module inlet 330 may be selected such that the resistance-to-draw is between 25-100 $mmH_2O$ (e.g., between 30-50 $mmH_2O$). For instance, a diameter of 1.0 mm for the first module inlet 330 may result in a resistance-to-draw of 88.3 $mmH_2O$. In another instance, a diameter of 1.1 mm for the first module inlet 330 may result in a resistance-to-draw of 73.6 $mmH_2O$. In another instance, a diameter of 1.2 mm for the first module inlet 330 may result in a resistance-to-draw of 58.7 $mmH_2O$. In yet another instance, a diameter of 1.3 mm for the first module inlet 330 may result in a resistance-to-draw of 43.8 $mmH_2O$. Notably, the size of the first module inlet 330, because of its internal arrangement, may be adjusted without affecting the external aesthetics of the non-nicotine pod assembly 300, thereby allowing for a more standardized product design for pod assemblies with various resistance-to-draw (RTD) while also reducing the likelihood of an inadvertent blockage of the incoming air.

Figure 29:
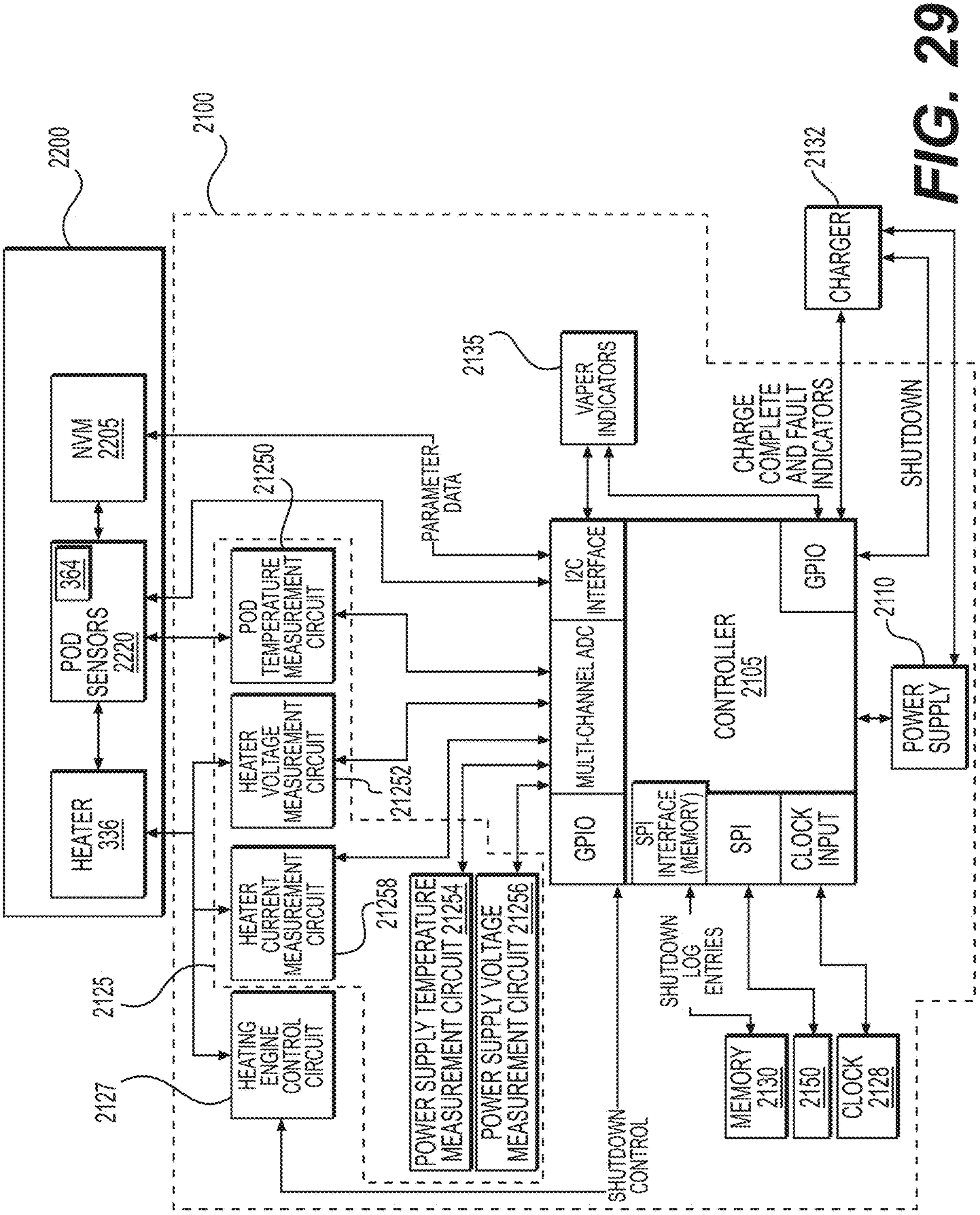
FIG. 29 illustrates electrical systems of a device body and a non-nicotine pod assembly of a non-nicotine e-vaping device according to an example embodiment.

FIG. 29 illustrates electrical systems of a device body and a non-nicotine pod assembly of a non-nicotine e-vaping device according to an example embodiment.

Referring to FIG. 29, the electrical systems include a device body electrical system 2100 and a non-nicotine pod assembly electrical system 2200. The device body electrical system 2100 may be included in the device body 100, and the non-nicotine pod assembly electrical system 2200 may be included in the non-nicotine pod assembly 300 of the non-nicotine e-vaping device 500 discussed above with regard to FIGS. 1-28.

In the example embodiment shown in FIG. 29, the non-nicotine pod assembly electrical system 2200 includes the heater 336, one or more pod sensors 2220 and a non-volatile memory (NVM) 2205. The NVM 2205 may be an electrically erasable programmable read-only memory (EEPROM) integrated circuit (IC).

The non-nicotine pod assembly electrical system 2200 may further include a body electrical/data interface (not shown) for transferring power and/or data between the device body 100 and the non-nicotine pod assembly 300. According to at least one example embodiment, the electrical contacts 324*a*, 324*b* and 326 shown in FIG. 17, for example, may serve as the body electrical/data interface.

The device body electrical system 2100 includes a controller 2105, a power supply 2110, device sensors or measurement circuits 2125 (referred to herein as device sensors 2125), a heating engine control circuit (also referred to as a heating engine shutdown circuit) 2127, vaper indicators 2135, on-product controls 2150 (e.g., buttons 118 and 120 shown in FIG. 1), a memory 2130, and a clock circuit 2128. The device body electrical system 2100 may further include a pod electrical/data interface (not shown) for transferring power and/or data between the device body 100 and the non-nicotine pod assembly 300. According to at least one example embodiment, the device electrical connector 132 shown in FIG. 12, for example, may serve as the pod electrical/data interface.

The power supply 2110 may be an internal power source to supply power to the device body 100 and the non-nicotine pod assembly 300 of the non-nicotine e-vaping device 500. The supply of power from the power supply 2110 may be controlled by the controller 2105 through power control circuitry (not shown). The power control circuitry may include one or more switches or transistors to regulate power output from the power supply 2110. The power supply 2110 may be a Lithium-ion battery or a variant thereof (e.g., a Lithium-ion polymer battery). The power supply 2110 may be connected to a charger 2132 (also referred to herein as a power supply charger or a battery charger) for charging. Example embodiments of the power supply charger 2132 will be discussed in more detail later with regard to FIGS. 44A and 44B.

The controller 2105 may be configured to control overall operation of the non-nicotine e-vaping device 500. According to at least some example embodiments, the controller 2105 may include processing circuitry such as hardware including logic circuits; a hardware/software combination such as a processor executing software; or a combination thereof. More specifically, for example, the processing circuitry may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), or the like.

In the example embodiment shown in FIG. 29, the controller 2105 is illustrated as a microcontroller including: input/output (I/O) interfaces, such as general purpose input/outputs (GPIOs), inter-integrated circuit ($I^2C$) interfaces, serial peripheral interface bus (SPI) interfaces, or the like; a multichannel analog-to-digital converter (ADC); and a clock input terminal. However, example embodiments should not be limited to this example. In at least one example implementation, the controller 2105 may be a microprocessor.

The controller 2105 is communicatively coupled to the device sensors 2125, the heating engine control circuit 2127, vaper indicators 2135, the memory 2130, the on-product controls 2150, the clock circuit 2128, and the power supply 2110. The controller 2105 may also be communicatively coupled to the charger 2132, (e.g., via a Universal Serial Bus (USB) connection) when charging the power supply 2110.

The heating engine control circuit 2127 is connected to the controller 2105 via a GPIO pin. The memory 2130 is connected to the controller 2105 via a SPI pin. The clock circuit 2128 is connected to a clock input pin of the controller 2105. The vaper indicators 2135 are connected to the controller 2105 via an $I^2C$ interface pin and a GPIO pin. The elements of the device sensors 2125 are connected to the controller 2105 through respective pins of the multi-channel ADC. When connected, the power supply charger 2132 may also be connected to the controller 2105 via a GPIO pin.

The clock circuit 2128 may be a timing mechanism, such as an oscillator circuit, to enable the controller 2105 to track idle time, a reset time via a reset timer, vaping length, a measurement interval, a combination thereof, or the like, of the non-nicotine e-vaping device 500. The clock circuit 2128 may also include a dedicated external clock crystal configured to generate the system clock for the non-nicotine e-vaping device 500.

The memory 2130 may be a non-volatile memory configured to store one or more shutdown (or fault event) logs. In one example, the memory 2130 may store the one or more shutdown logs in one or more tables. The memory 2130 and the one or more shutdown logs stored therein will be discussed in more detail later. In one example, the memory 2130 may be an electrically erasable programmable read-only memory (EEPROM), such as a flash memory or the like.

Still referring to FIG. 29, the device sensors 2125 may include a plurality of sensor or measurement circuits configured to provide measurements or signals indicative of sensor or measurement information to the controller 2105. In the example shown in FIG. 29, the device sensors 2125 include a heater current measurement circuit 21258, a heater voltage measurement circuit 21252, a pod temperature measurement circuit 21250, a power supply temperature measurement circuit 21254 and a power supply voltage measurement circuit 21256.

The heater current measurement circuit 21258 may be configured to output (e.g., voltage) signals indicative of the current through the heater 336. An example embodiment of the heater current measurement circuit 21258 will be discussed in more detail later with regard to FIG. 35.

The heater voltage measurement circuit 21252 may be configured to output (e.g., voltage) signals indicative of the voltage across the heater 336. An example embodiment of the heater voltage measurement circuit 21252 will be discussed in more detail later with regard to FIG. 34.

The pod temperature measurement circuit 21250 may be configured to output (e.g., voltage) signals indicative of the resistance and/or temperature of one or more elements of the non-nicotine pod assembly 300. Example embodiments of the pod temperature measurement circuit 21250 will be discussed in more detail later with regard to FIGS. 36 and 37.

The power supply temperature measurement circuit 21254 may be configured to measure the temperature of the power supply 2110 during operation and/or charging. Example embodiments of the power supply temperature measurement circuit 21254 will be discussed in more detail later with regard to FIGS. 42A and 42B.

The power supply voltage measurement circuit 21256 may be configured to output signals indicative of the voltage of the power supply 2110 during operation and/or charging. Example embodiments of the power supply voltage measurement circuit 21256 will be discussed in more detail later with regard to FIGS. 43A and 43B.

As discussed above, the pod temperature measurement circuit 21250, the heater current measurement circuit 21258, the heater voltage measurement circuit 21252, the power supply temperature measurement circuit 21254 and the power supply voltage measurement circuit 21256 are connected to the controller 2105 via pins of the multi-channel ADC. To measure characteristics and/or parameters of the non-nicotine e-vaping device 500 (e.g., voltage, current, resistance, temperature, or the like, of the heater 336), the multi-channel ADC at the controller 2105 may sample the output signals from the device sensors 2125 at a sampling rate appropriate for the given characteristic and/or parameter being measured by the respective device sensor.

As shown in FIG. 29, the pod sensors 2220 also include the sensor 364 shown in FIG. 28. In at least one example embodiment, the sensor 364 may be a microelectromechanical system (MEMS) flow or pressure sensor or another type of sensor configured to measure air flow such as a hot-wire anemometer.

The heating engine control circuit 2127 is connected to the controller 2105 via a GPIO pin. The heating engine control circuit 2127 is configured to control (enable and/or disable) the heating engine of the non-nicotine e-vaping device 500 by controlling power to the heater 336. As discussed in more detail later, the heating engine control circuit 2127 may disable the heating engine based on control signaling (sometimes referred to herein as device power state signals) from the controller 2105.

When the non-nicotine pod assembly 300 is inserted into the device body 100, the controller 2105 is also communicatively coupled to at least the NVM 2205 and the pod sensors 2220 via the $I^2C$ interface. In one example, the controller 2105 may obtain operating parameters for the non-nicotine pod assembly electrical system 2200 from the NVM 2205.

The controller 2105 may control the vaper indicators 2135 to indicate statuses, fault events and/or operations of the non-nicotine e-vaping device 500 to an adult vaper. The vaper indicators 2135 may be at least partially implemented via a light guide (e.g., the light guide arrangement shown in FIG. 1), and may include a power indicator (e.g., LED) that may be activated when the controller 2105 senses a button pressed by the adult vaper. The vaper indicators 2135 may also include a vibrator, speaker, display device (display unit or display), or other feedback mechanisms, and may indicate a current state of an adult vaper-controlled vaping parameter (e.g., non-nicotine vapor volume).

Still referring to FIG. 29, the controller 2105 may control power to the heater 336 to heat the non-nicotine pre-vapor formulation in accordance with a heating profile (e.g., heating based on volume, temperature, flavor, or the like). The heating profile may be determined based on empirical data and may be stored in the NVM 2205 of the non-nicotine pod assembly 300.

Figure 30:
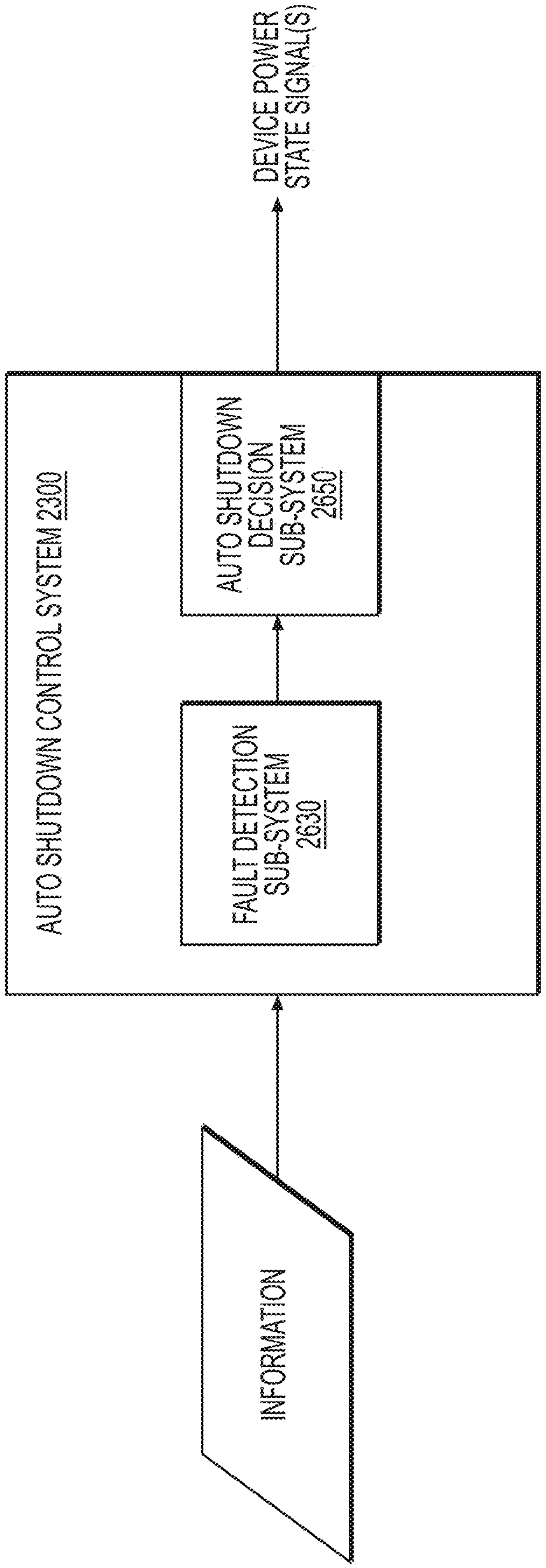
FIG. 30 is a simple block diagram illustrating an auto shutdown control system 2300 according to an example embodiment.

FIG. 30 is a simple block diagram illustrating an auto shutdown control system 2300 according to an example embodiment.

The auto shutdown control system 2300 shown in FIG. 30 may be implemented at the controller 2105. In one example, the auto shutdown control system 2300 may be implemented as part of a device manager Finite State Machine (FSM) software implementation at the controller 2105. In the example shown in FIG. 30, the auto shutdown control system 2300 includes a fault detection sub-system 2630 and an auto shutdown decision sub-system 2650. It should be understood, however, that the auto shutdown control system 2300 may include various other sub-systems.

Referring to FIG. 30, the auto shutdown control system 2300, and more generally the controller 2105, may detect fault events (or conditions) at the non-nicotine e-vaping device 500, and cause the controller 2105 to control one or more sub-systems of the non-nicotine e-vaping device 500 to perform one or more consequent actions in response to detecting the fault events. As discussed in more detail later, types of fault events may include normal (fault) events, soft fault pod events, hard fault pod events, soft fault device events, and hard fault device events.

Normal events may include, for example, a power supply (or battery) fully charged event (charging complete event), adult vaper input events (e.g., via on-product controls 2150), inserting of the non-nicotine pod assembly electrical system 2200, an idling event (or idling fault event), a combination thereof, or the like. More generally, for example, a normal event may be a normal condition at the non-nicotine e-vaping device 500 for which vaping or other function of the non-nicotine e-vaping device 500 may not be disabled.

Soft fault pod events may include, for example, a heater temperature fault event in which the temperature of the heater 336 exceeds a threshold maximum value. More generally, for example, a soft fault pod event may be an abnormal condition within the non-nicotine pod assembly 300 for which a consequent action (e.g., disabled vaping) occurs and that may not require adult vaper interaction with the non-nicotine electronic vaping device 500 to be remedied.

Hard fault pod events may include an open circuit failure in the heater 336, depletion of non-nicotine pre-vapor formulation in the non-nicotine pod assembly 300 (pod empty), a combination thereof, or the like. More generally, for example, a hard fault pod event may be an abnormal condition within the non-nicotine pod assembly 300 for which a consequent action (e.g., disabled vaping) occurs and that requires adult vaper interaction with the non-nicotine electronic vaping device 500 to be remedied.

Examples of soft fault device events may be a boot fault and a power supply low voltage fault event in which the voltage of the power supply 2110 falls below a threshold minimum (e.g., the power supply becomes depleted and requires recharging). The power supply low voltage fault event may also be referred to herein as a power supply (or battery) low voltage fault or battery low voltage fault event. More generally, for example, a soft fault device event may be an abnormal condition at the non-nicotine e-vaping device 500 for which vaping is disabled until corrective action is taken.

Examples of hard fault device events may be a power supply (or battery) charging failure at the charger 2132 and a power stage fault, which will be discussed in more detail later. More generally, for example, a hard fault device event may be an abnormal condition at the non-nicotine e-vaping device 500 for which at least vaping is disabled and that requires adult vaper intervention to be remedied.

The controller 2105 may control the one or more sub-systems by outputting one or more control signals (or asserting or de-asserting a respective signal) as will be discussed in more detail later. In some cases, the control signals output from the controller 2105 may be referred to as device power state signals, device power state instructions or device power control signals. According to one or more example embodiments, the controller 2105 may output one or more control signals to the heating engine control circuit 2127 to cut power to the heater 336 and/or shutdown vaping functions at the non-nicotine e-vaping device 500 and/or output one or more control signals to the charger 2132 to perform a charging stop operation, in response to detecting one or more fault events at the non-nicotine e-vaping device 500.

According to one or more example embodiments, the type of consequent actions at the non-nicotine e-vaping device 500 may depend on the identified fault event and/or the current operation of the non-nicotine e-vaping device. Multiple consequent actions may be performed serially in response to a fault event. In one example, consequent actions may include:

(i) an auto off operation in which the non-nicotine e-vaping device 500 switches to a low power state (e.g., equivalent to turning the non-nicotine e-vaping device off using the power button);

(ii) a heater off operation in which power to the heater 336 is cut off or disabled, ending the current puff, but otherwise remaining ready for vaping;

(iii) a vaping off operation in which the vaping sub-system is disabled (e.g., by disabling all power to the heater 336), thereby preventing vaping until a corrective action is taken (e.g., recharging the power supply, replacing the non-nicotine pod assembly, etc.);

(iv) a device soft reset in which the non-nicotine e-vaping device software is reset in order to clear the fault event and return the non-nicotine e-vaping device to a known normal operating state;

(v) a device hard reset in which the device software and hardware is reset in order to clear the fault event and return the non-nicotine e-vaping device to a known normal operating state; and (vi) a charger stop in which the power supply charging process is stopped and will not restart until a corrective action is taken.

Still referring to FIG. 30, in a more specific example, the fault detection sub-system 2630, and more generally the controller 2105, may detect an idling event at the non-nicotine e-vaping device 500, and output one or more control signals (or assert or de-assert a respective signal) to cause the non-nicotine e-vaping device 500 to perform one or more consequent actions in response to the idling event. The fault detection sub-system 2630 may determine whether an idling event has occurred based on: a determination that a shutdown timer has lapsed, whether any software timers are running in the device firmware, whether any software events are on software queues waiting to be processed (e.g., communication messages from external devices via wired or wireless communication), whether any hardware operations (e.g., Direct Memory Access (DMA) transactions) are ongoing, or a combination thereof. If these checks return false, then the fault detection sub-system 2630 may output an idling alert (or idling event alert) to the auto shutdown decision sub-system 2650 in response to which the auto shutdown decision sub-system 2650 may cause the non-nicotine e-vaping device 500 to enter into a low power state by disabling one or more subsystems of the non-nicotine e-vaping device 500. In one example, the auto shutdown decision sub-system 2650 (or, more generally, the controller 2105) may output a multitude or plurality of GPIO control lines (signals) to turn off all or substantially all peripherals of the non-nicotine e-vaping device 500 and cause the controller 2105 to enter a sleep state.

Functions and/or operations according to one or more example embodiments may be discussed herein with regard to being performed by the controller 2105, the fault detection sub-system 2630 and/or the auto shutdown decision sub-system 2650 in certain contexts. However, it should be understood, however, that functions and/or operations discussed with regard to the controller 2105 may be interchangeably discussed as being performed by the fault detection sub-system 2630 and/or the auto shutdown decision sub-system 2650. Similarly, it should be understood that functions and/or operations discussed with regard to the fault detection sub-system 2630 and/or the auto shutdown decision sub-system 2650 may be interchangeably discussed as being performed by the controller 2105.

Figure 31:
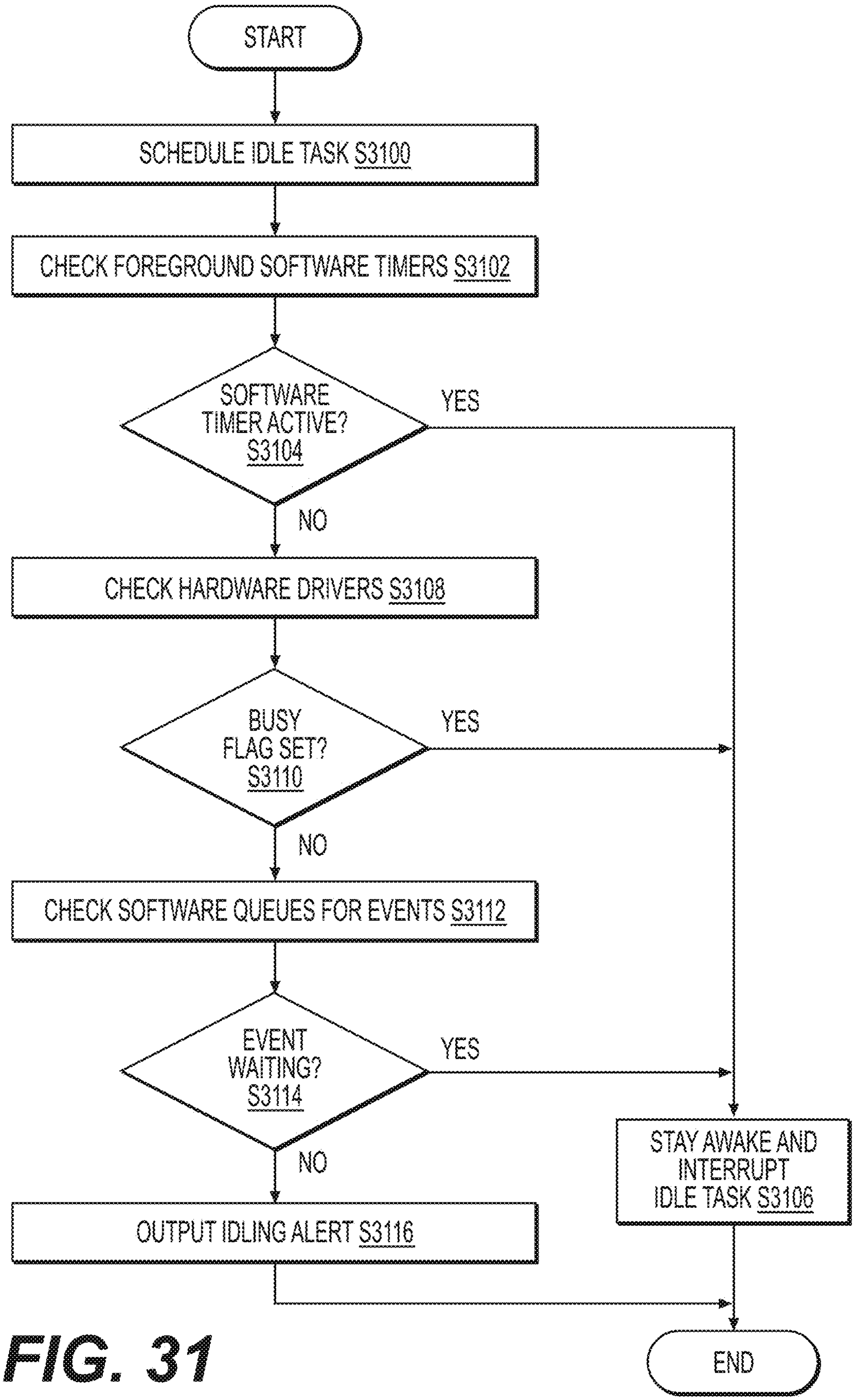
FIG. 31 is a flow chart illustrating a method for detecting an idling event according to an example embodiment.

FIG. 31 is a flow chart illustrating a method for detecting an idling event according to an example embodiment. The flow chart in FIG. 31 is a single iteration of a process for idling detection. The fault detection sub-system 2630 may continuously and/or periodically perform this process to determine whether to perform a consequent action, such as causing the non-nicotine e-vaping device 500 to enter a low power sleep state.

For example purposes, the flow chart shown in FIG. 31 will be discussed with regard to the electrical systems shown in FIG. 29. It should be understood, however, that example embodiments should not be limited to this example. Rather, example embodiments may be applicable to other non-nicotine e-vaping devices and electrical systems thereof. Moreover, the example embodiment shown in FIG. 31 will be described with regard to operations performed by the fault detection sub-system 2630. However, it should be understood that the example embodiment may be described similarly with regard to the auto shutdown control system 2300 and/or the controller 2105 performing one or more of the functions/operations shown in FIG. 31.

Referring to FIG. 31, at step S3100 the fault detection sub-system 2630 schedules an idle task to cause the non-nicotine e-vaping device 500 to output an idling alert to the auto shutdown decision sub-system 2650 pending check of software timers, hardware drivers and software queues at the non-nicotine e-vaping device 500.

At step S3102, the fault detection sub-system 2630 checks the foreground software timers at the controller 2105 to determine whether any foreground software timers are currently active. According to one or more example embodiments, a foreground software timer is initiated each time a software module at the non-nicotine e-vaping device 500 initiates an activity. The fault detection sub-system 2630 determines that a foreground software timer is active if the foreground software timer has not lapsed (counted down to zero) or been interrupted by its respective software module (the activity has completed).

An example of a special case foreground timer is a timer used to monitor adult vaper interaction with the non-nicotine e-vaping device 500. This may be referred to as a Device Off' software timer, and may be used to determine the length of time since the adult vaper last interacted with the non-nicotine e-vaping device 500. This timer may correspond to a time period (e.g., number of seconds or minutes) after which the non-nicotine e-vaping device 500 will automatically enter a low power state or shut down. The timer may be set to a value specified by an adult vaper (e.g., via the on-product controls 2150, a connected application or "App," a combination thereof, or the like). The timer may count down in 1 millisecond increments, and may restart each time the adult vaper interacts with the non-nicotine e-vaping device 500. In at least one example embodiment, interactions by the adult vaper that may restart this foreground timer and maintain the device in an awake state (e.g., prevent the device from entering the low power state) include pressing a button on the non-nicotine e-vaping device 500, vaping, inserting the non-nicotine pod assembly 300, disconnecting the non-nicotine e-vaping device 500 from a USB cable, a combination thereof, or the like.

If one or more foreground software timers are active (step S3104), then the fault detection sub-system 2630 interrupts the scheduled idle task and does not output an idling alert to the auto shutdown decision sub-system 2650. In this case, the non-nicotine e-vaping device 500 remains in an awake state ready for vaping.

Returning to step S3104, if no foreground software timers are active (e.g., all foreground software timers have lapsed or been interrupted), then at step S3108 the fault detection sub-system 2630 checks the hardware drivers at the controller 2105 to determine whether any hardware operations (e.g., DMA transactions, or the like) are underway at the non-nicotine e-vaping device 500.

Each time a hardware operation starts, the driver software for that operation registers itself as 'busy' by setting a busy flag. The driver software then sets itself to 'idle' (resetting the busy flag) when the hardware operation has completed (e.g., an interrupt is received, or a data transaction is finished). Accordingly, the fault detection sub-system 2630 may determine whether any hardware operations are currently on-going by checking whether the busy flag for a hardware operation is set.

If the fault detection sub-system 2630 determines that one or more hardware operations are underway (e.g., a busy flag is set for at least one hardware driver) at step S3110, then the process proceeds to step S3106 and continues as discussed above.

Returning to step S3110, if the fault detection sub-system 2630 determines that no hardware operations are currently underway (e.g., no busy flags are set), then at step S3112 the fault detection sub-system 2630 checks software queues for events awaiting processing at the controller 2105. According to one or more example embodiments, the controller 2105 may schedule events for execution in a software queue in response to, for example, communication messages from external devices via wired (e.g., Universal Serial Bus (USB)) and/or wireless (e.g., short-range wireless, such as Bluetooth) communication.

According to at least one example embodiment, a software queue check such as that performed at step S3112 may be performed as a task in a Real Time Operating System (RTOS) executed at the controller 2105.

If the fault detection sub-system 2630 determines that there are events in the software queues awaiting processing at step S3114, then the process proceeds to step S3106 and continues as discussed above.

Returning to step S3114, if the fault detection sub-system 2630 determines that there are no software events awaiting processing, then the fault detection sub-system 2630 outputs an idling alert to the auto shutdown decision sub-system 2650 to indicate that an idling event has occurred. In response to the idling alert, the auto shutdown decision sub-system 2650 may determine one or more consequent actions to be taken, and may output one or more device power state signals to control the non-nicotine e-vaping device 500 to perform the one or more consequent actions. Example operation of the auto shutdown decision sub-system 2650 in response to fault alerts, such as the idling alert discussed above, will be discussed in more detail below with regard to FIGS. 33A and 33B.

Returning again to FIG. 30, in another example, the fault detection sub-system 2630 may detect and/or determine when the temperature of the heater 336 reaches or exceeds (is greater than or equal to) a threshold maximum temperature value (Heater_Max_Temperature threshold parameter) (a heater temperature fault event), and output a temperature alert to the auto shutdown decision sub-system 2650 in response thereto.

The fault detection sub-system 2630 may determine whether to output the temperature alert based on a temperature of the heater 336 and a confidence interval (CI). The threshold maximum temperature value and the CI may be determined based on empirical data, and may be stored and obtained from the NVM 2205 in the non-nicotine pod assembly electrical system 2200. The temperature of the heater 336 (or signals indicative of the temperature of the heater 336) may be provided by, for example, a temperature sensing transducer component of the pod sensors 2220.

In an alternative example, the controller 2105 may determine the temperature of the heater 336 based on voltage measurements from the heater voltage measurement circuit 21252 and/or current measurements by the heater current measurement circuit 21258.

The CI is a level of engineering margin for the temperature of the heater 336. For a resistance-based measurement of the heater 336, the temperature estimate may be relatively inaccurate due to component tolerances, rounding errors, variable contact resistance, etc. Accordingly, a theoretical worst case error may be applied as the CI. In at least one example embodiment, the worst case error may be approximately 15° C.

For a pod sensor-based measurement, the CI for estimating a temperature of the heater 336 may be greater (e.g., on the order of about 50° C.-100° C.) because the pod sensor may not be in close proximity to the heater 336, and thus, the temperature of the heater 336 may be inferred rather than estimated. According to at least one example embodiment, pod sensor-based measurements may be used as (e.g., only as) a measure of the temperature of the enclosure, rather than the heater itself, and the shutoff point from this reading was therefore dedicated to prevent the temperature of the body of the pod from increasing above a maximum threshold.

Figure 32A:
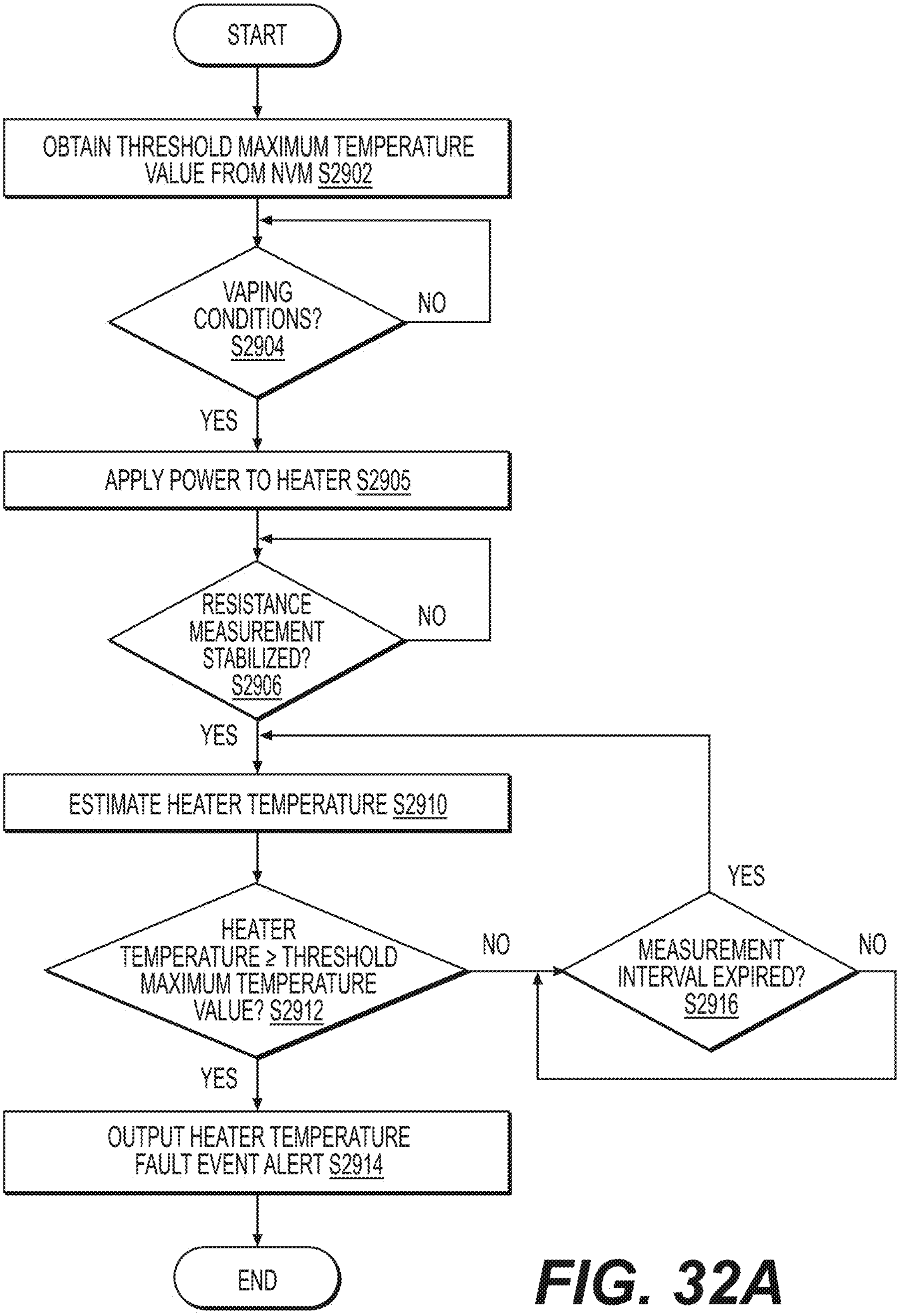
FIG. 32A is a flow chart illustrating method for detecting a heater temperature fault event according to an example embodiment.

FIG. 32A is a flow chart illustrating a method for detecting a heater temperature fault event according to an example embodiment.

For example purposes, the flow chart shown in FIG. 32A will be discussed with regard to the electrical systems shown in FIG. 29. It should be understood, however, that example embodiments should not be limited to this example. Rather, example embodiments may be applicable to other non-nicotine e-vaping devices and electrical systems thereof. Moreover, the example embodiment shown in FIG. 32A will be described mostly with regard to operations performed by the fault detection sub-system 2630. However, it should be understood that the example embodiment may be described similarly with regard to the auto shutdown control system 2300 and/or the controller 2105 performing one or more of the functions/operations shown in FIG. 32A.

Referring to FIG. 32A, when the non-nicotine pod assembly 300 is inserted into the device body 100, at step S2902 the fault detection sub-system 2630 obtains the threshold maximum temperature value from the NVM 2205 in the non-nicotine pod assembly electrical system 2200. In one example, the threshold maximum temperature value may be stored within a single byte at a resolution of about 2° C., and may be in the range of between about 0° C. and about 510° C.

According to at least one example embodiment, the temperature was stored at a resolution of about 2° C. to fit a useful range in a single byte. Since the requisite range, according to at least one example embodiment, covers at least about 0-300° C., a temperature stored at a resolution of about 1° C. would not fit in a single byte (e.g., that would only have provided a range of 0–255° C.).

At step S2904, the fault detection sub-system 2630 determines whether vaping conditions exist at the non-nicotine e-vaping device 500. According to at least one example embodiment, the fault detection sub-system 2630 may determine whether vaping conditions exist at the non-nicotine e-vaping device 500 based on output from the sensor 364. In one example, if the output from the sensor 364 indicates application of negative pressure above a threshold at the mouthpiece 102 of the non-nicotine e-vaping device 500, then the fault detection sub-system 2630 may determine that vaping conditions exist at the non-nicotine e-vaping device 500.

If the fault detection sub-system 2630 determines that vaping conditions are present at the non-nicotine e-vaping device 500, then at step S2905 the controller 2105 controls the heating engine control circuit 2127 to apply power to the heater 336 for vaping. Example control of the heating engine control circuit 2127 to apply power to the heater 336 will be discussed in more detail later with regard to FIGS. 38 and 39.

At step S2906, the fault detection sub-system 2630 determines whether the resistance of the heater 336 has stabilized. The fault detection sub-system 2630 may determine that the resistance of the heater 336 has stabilized once the current through the heater 336 reaches a 'wetting' current threshold (e.g., about 100 milliamps (mA)). The fault detection sub-system 2630 may determine that the current through the heater 336 has reached the 'wetting' current threshold based on output signals from the heater current measurement circuit 21258.

If the fault detection sub-system 2630 determines that the resistance of the heater 336 has stabilized, then at step S2910 the fault detection sub-system 2630 estimates the temperature of the heater 336 based on the measured resistance of the heater 336. The fault detection sub-system 2630 may estimate the temperature of the heater 336 in any known manner (e.g., based on the relatively linear relationship between resistance and temperature of the heater 336). In one example, as will be discussed in more detail later, the fault detection sub-system 2630 may determine the temperature measurement based on output from a temperature sensing transducer component of the pod sensors 2220.

Still referring to FIG. 32A, at step S2912 the fault detection sub-system 2630 determines whether the estimated temperature of the heater 336 is greater than or equal to (has reached or exceeded) the threshold maximum temperature by comparing the estimated temperature with the threshold maximum temperature value obtained from the NVM 2205.

If the fault detection sub-system 2630 determines that the estimated temperature of the heater 336 is less than the threshold maximum temperature, then at step S2916 the fault detection sub-system 2630 determines whether a measurement interval has expired. The measurement interval may be determined based on empirical data. In one example, the measurement interval may be about 10 milliseconds.

According to at least one example embodiment, a 10 millisecond measurement interval may be used for measurements taken from the I2C pod sensor (since this may be the maximum sample rate). In at least one other example embodiment, however, for a resistance-based heater measurement a 1 millisecond measurement interval (the tick rate of the system) may be used.

If the measurement interval has expired, then the process returns to step S2910 and continues as discussed herein.

Returning to step S2916, if the measurement interval has not yet expired, then the fault detection sub-system 2630 waits for the measurement interval to expire before returning to step S2910 and continuing as discussed herein.

Returning to step S2912, if the fault detection sub-system 2630 determines that the estimated temperature of the heater 336 has reached or exceeded the threshold maximum temperature value, then at step S2914 the fault detection sub-system 2630 outputs a heater temperature fault event alert to the auto shutdown decision sub-system 2650.

Returning to step S2906, if the fault detection sub-system 2630 determines that the resistance of the heater 336 has not yet stabilized, then the fault detection sub-system 2630 continues to monitor (or waits for) the resistance of the heater 336. Once the resistance of the heater 336 has stabilized, the process proceeds to step S2910 and continues as discussed above.

Returning to step S2904, if the fault detection sub-system 2630 determines that vaping conditions are not present at the non-nicotine e-vaping device 500, then the fault detection sub-system 2630 continues to monitor output of the sensor 364 for the presence of non-nicotine e-vaping conditions. Once non-nicotine e-vaping conditions are detected, the process continues as discussed above.

Figure 32B:
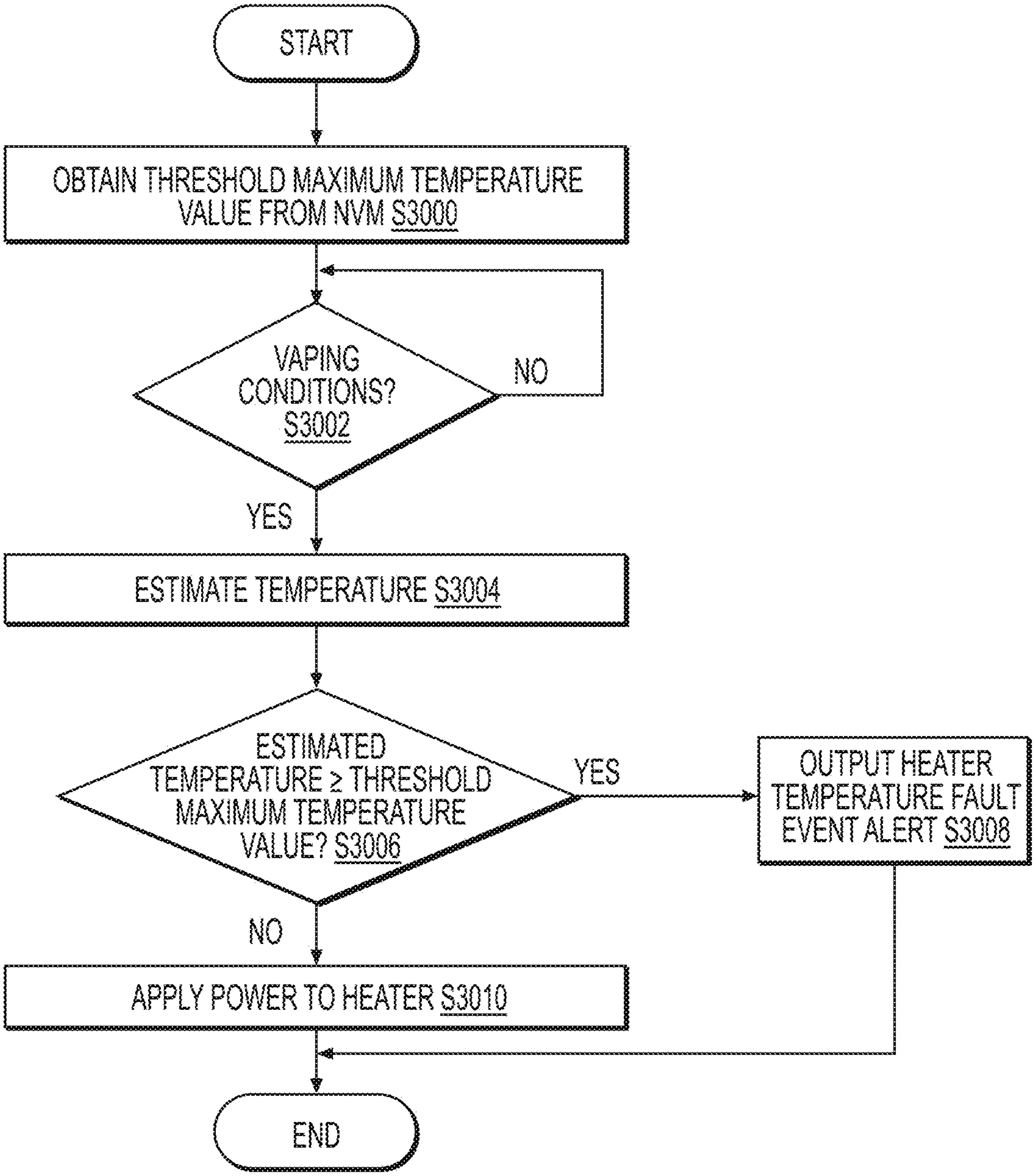
FIG. 32B is a flow chart illustrating a method for detecting a heater temperature fault event according to another example embodiment.

FIG. 32B is a flow chart illustrating a method for detecting a heater temperature fault event according to another example embodiment. The method shown in FIG. 32B may enable the non-nicotine e-vaping device 500 to determine whether to apply power to the heater 336 at the start of a puff event (e.g., upon initial application of negative pressure to the mouthpiece 102).

As with the example embodiment shown in FIG. 32A, for example purposes, the flow chart shown in FIG. 32B will be discussed with regard to the electrical systems shown in FIG. 29. It should be understood, however, that example embodiments should not be limited to this example. Rather, example embodiments may be applicable to other non-nicotine e-vaping devices and electrical systems thereof. Moreover, the example embodiment shown in FIG. 32B will be described mostly with regard to operations performed by the fault detection sub-system 2630. However, it should be understood that the example embodiment may be described similarly with regard to the auto shutdown control system 2300 and/or the controller 2105 performing one or more of the functions/operations shown in FIG. 32B.

Referring to FIG. 32B, when the non-nicotine pod assembly 300 is inserted into the device body 100, at step S3000 the fault detection sub-system 2630 obtains the threshold maximum temperature value from the NVM 2205 in the non-nicotine pod assembly electrical system 2200. The threshold maximum temperature value may be the same or substantially the same as that discussed above with regard to step S2902 in FIG. 32A.

At step S3002, the fault detection sub-system 2630 determines whether vaping conditions exist at the non-nicotine e-vaping device 500. The fault detection sub-system 2630 may determine whether vaping conditions exist at the non-nicotine e-vaping device 500 in the same or substantially the same manner as discussed above with regard to step S2904 in FIG. 32A.

If the fault detection sub-system 2630 detects the presence of vaping conditions at step S3002, then at step S3004 the fault detection sub-system 2630 estimates the temperature of the heater 336 based on information from the temperature sensing transducer component of the pod sensors 2220. The fault detection sub-system 2630 may estimate the temperature of the heater 336 in the same or substantially the same manner as discussed above with regard to step S2910 in FIG. 32A.

At step S3006, the fault detection sub-system 2630 determines whether the estimated temperature is, for example, greater than or equal to the threshold maximum temperature value by comparing the estimated temperature with the threshold maximum temperature value obtained from the NVM 2205. The threshold maximum temperature value obtained from the NVM 2205 may be the same or substantially the same as that discussed above with regard to FIG. 32A.

If the fault detection sub-system 2630 determines that the estimated temperature exceeds the threshold maximum temperature value, then at step S3008 the fault detection sub-system 2630 outputs a heater temperature fault event alert to the auto shutdown decision sub-system 2650, and the process terminates.

Returning to step S3006, if the fault detection sub-system 2630 determines that the estimated temperature does not exceed the threshold maximum temperature value, then the fault detection sub-system 2630 need not output the heater temperature fault event alert to the fault detection sub-system 2630, and the controller 2105 may apply power to the heater 336 at step S3010.

Figure 33A:
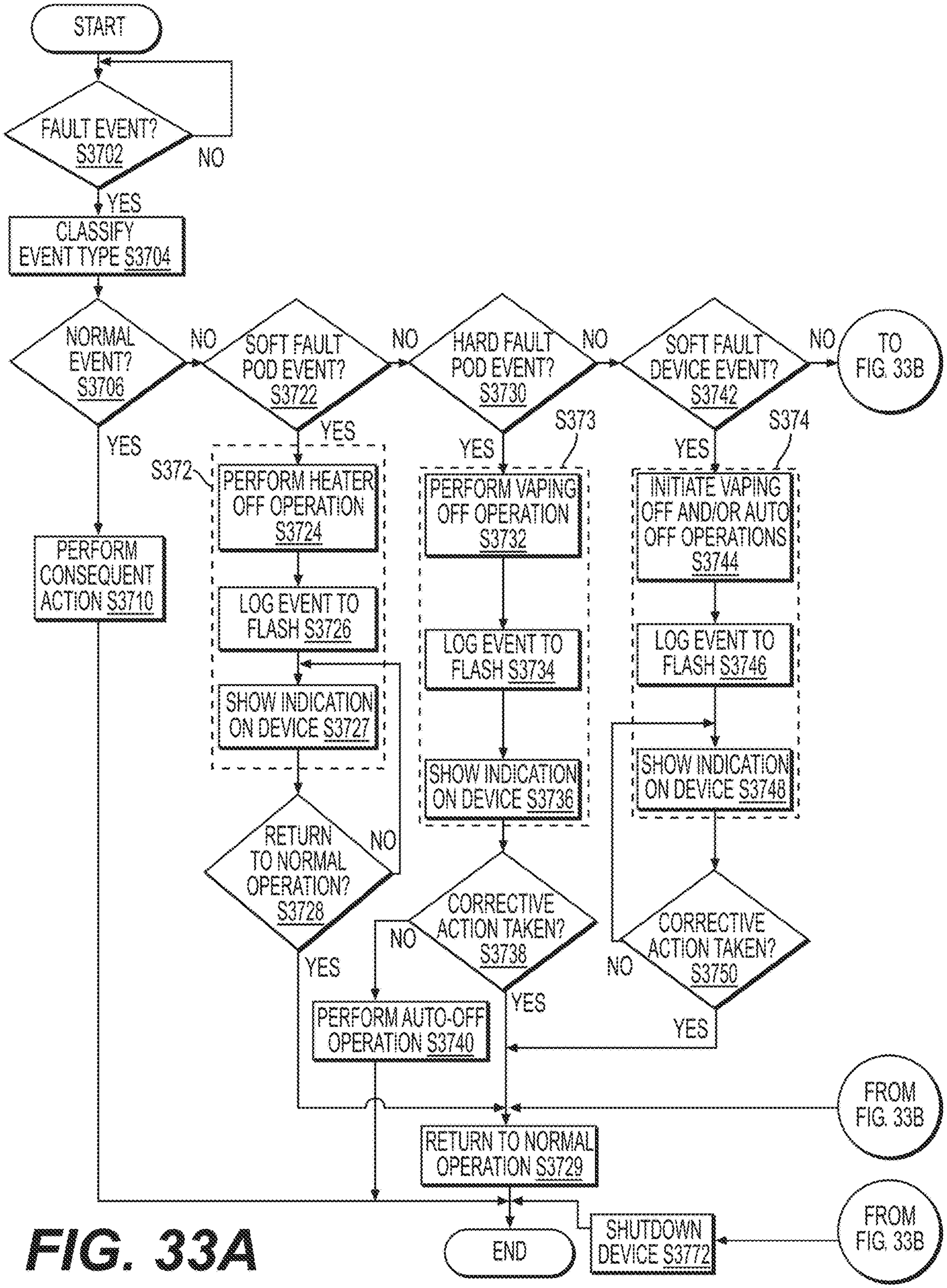
FIG. 33A and FIG. 33B illustrate an auto shutdown control method according to one or more example embodiments.
Figure 33B:
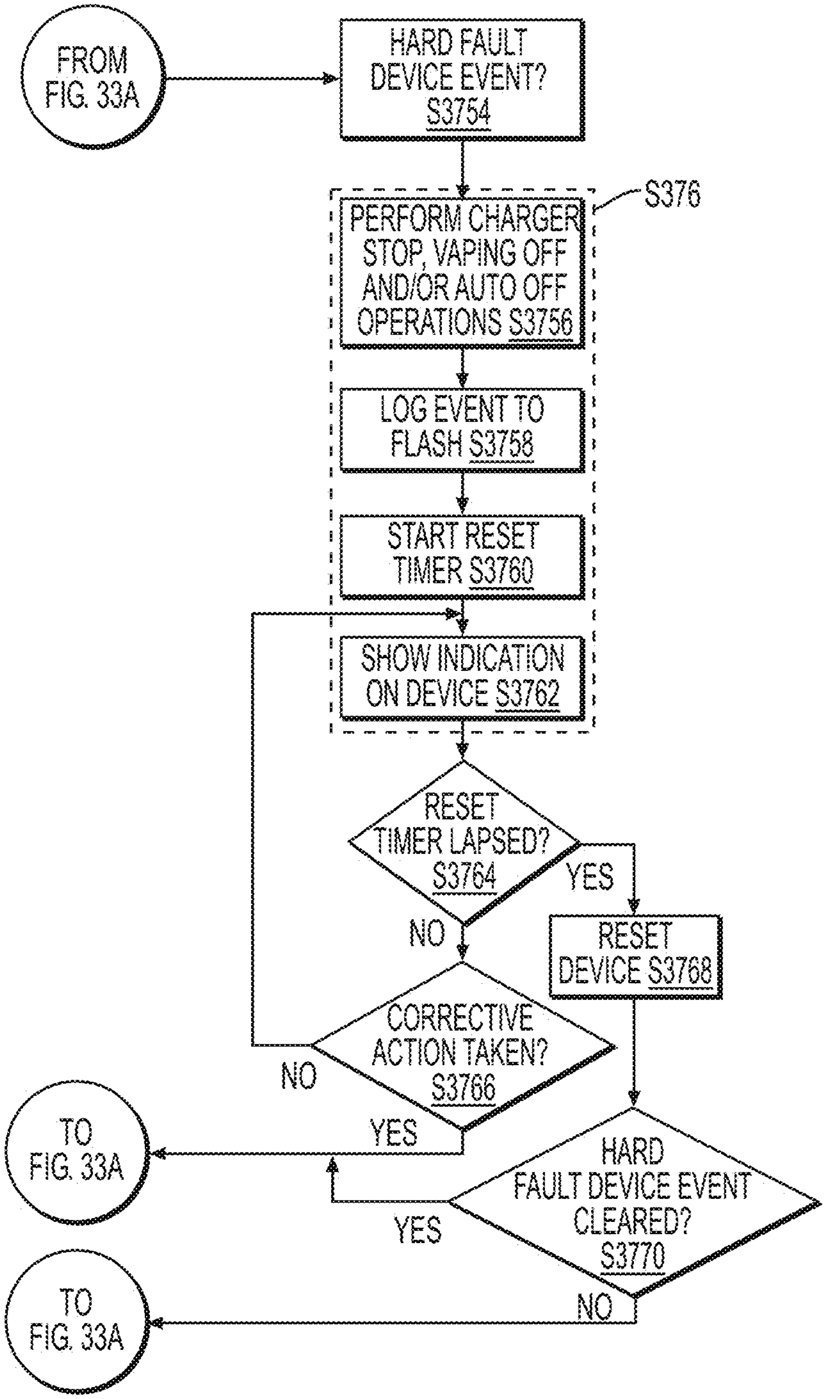

FIGS. 33A and 33B illustrate an auto shutdown control method according to one or more example embodiments.

For example purposes, the flow chart shown in FIGS. 33A and 33B will be discussed with regard to the electrical systems shown in FIG. 29. It should be understood, however, that example embodiments should not be limited to this example. Rather, example embodiments may be applicable to other non-nicotine e-vaping devices and electrical systems thereof. Moreover, the example embodiment shown in FIGS. 33A and 33B will be described mostly with regard to operations performed by the auto shutdown decision sub-system 2650. However, it should be understood that the example embodiment may be described similarly with regard to the auto shutdown control system 2300 and/or the controller 2105 performing one or more of the functions/operations shown in FIGS. 33A and 33B.

Referring to FIGS. 33A and 33B, at step S3702, the auto shutdown decision sub-system 2650 determines whether a fault event has occurred at the non-nicotine e-vaping device 500. According to one or more example embodiments, the auto shutdown decision sub-system 2650 determines that a fault event has occurred in response to receiving a fault alert from the fault detection sub-system 2630.

If the auto shutdown decision sub-system 2650 determines that a fault event has occurred, then at step S3704 the auto shutdown decision sub-system 2650 classifies the fault event as one of a normal fault event, a soft fault pod event, a hard fault pod event, a soft fault device event or a hard fault device event. According to one or more example embodiments, the auto shutdown decision sub-system 2650 may classify the fault event by utilizing a lookup table storing fault event classifications in association with specific fault events and/or fault error codes associated therewith. In this example, the fault detection sub-system 2630 may output an indication of the fault event that has triggered the fault alert to be sent to the auto shutdown decision sub-system 2650.

In at least one example embodiment, the classification may be implemented using a 'switch' programming statement to select the fault type based on the enumerated value of the fault.

As mentioned similarly above, normal fault events may include an interrupt from the charger 2132 indicating that charging of the power supply 2110 is complete, adult vaper input (e.g., to shut down the vaping sub-system or the non-nicotine e-vaping device) via the on-product controls 2150, an idling event in which the non-nicotine e-vaping device 500 has remained idle for at least a threshold time interval (e.g., as discussed above with regard to FIG. 31), a combination thereof, or the like.

If the auto shutdown decision sub-system 2650 classifies the fault event as a normal fault event, then at step S3710 the auto shutdown decision sub-system 2650 causes the non-nicotine e-vaping device 500 to perform one or more consequent actions depending on the fault event that has occurred. For example, the auto shutdown decision sub-system 2650 may output one or more device power state signals to control the non-nicotine e-vaping device 500 to perform one or more consequent actions (e.g., a charger stop operation, a vaping off operation, an auto off operation, a heater off operation, a combination thereof, or the like).

In an example in which the normal fault event is an interrupt from the charger 2132 indicating that charging of the power supply 2110 is complete, the fault detection sub-system 2630 may receive the interrupt from the charger 2132. In response to receiving the interrupt from the charger 2132, the fault detection sub-system 2630 may output a fault alert (charging complete fault alert) to the auto shutdown decision sub-system 2650 indicating that the interrupt has been received. In response to the fault alert, the auto shutdown decision sub-system 2650 determines that a normal fault event has occurred, and initiates/performs a charger stop operation.

As discussed in more detail later, the charger 2132 may include a dedicated charging IC including a number of input/outputs (I/O) that are used to manage and control charging of the power supply 2110. The charger stop operation may disable or suspend charging of the power supply 2110 at the non-nicotine e-vaping device 500. As discussed in more detail later, the controller 2105 may control the charger 2132 to disable or suspend charging of the power supply 2110 by outputting a charger stop signal BATT_SUSP (e.g., having a logic high level) to the dedicated charging IC at the charger 2132.

In an example in which the normal fault event is an interrupt generated in response to input via the on-product controls 2150 (e.g., requesting disable of vaping function, disabling power to the heater 336, or to power down the non-nicotine e-vaping device 500), the fault detection sub-system 2630 may receive the interrupt from the on-product controls 2150. In response to receiving the interrupt, the fault detection sub-system 2630 may output a fault alert (adult vaper fault alert) to the auto shutdown decision sub-system 2650 indicating that the interrupt has been received. In response to the fault alert, the auto shutdown decision sub-system 2650 determines that a normal fault event has occurred, and initiates/performs a vaping off operation, a heater off operation, an auto off operation, a combination thereof, or the like, as needed.

According to at least some example embodiments, the auto shutdown decision sub-system 2650 (or controller 2105) may perform the auto off operation by outputting a multitude or plurality of GPIO control lines (signals) to turn off all or substantially all peripherals of the non-nicotine e-vaping device 500 and cause the controller 2105 to enter a sleep state.

A vaping off operation may disable all energy to the heater 336, thereby preventing vaping until corrective action is taken (e.g., by an adult vaper). As discussed in more detail later, the auto shutdown decision sub-system 2650 may control the heating engine control circuit 2127 to disable all energy to the heater 336 by outputting a vaping shutdown signal COIL_SHDN having a logic high level (FIG. 38) or by de-asserting (or stopping output of) a vaping enable signal COIL_VGATE_PWM (FIG. 39). In at least one example, at least the vaping enable signal COIL_VGATE_PWM may be a pulse width modulation (PWM) signal.

The heater off operation may cut power to the heater 336, ending any current puff event, but otherwise allowing the non-nicotine e-vaping device 500 to remain ready for vaping. As discussed in more detail later, the auto shutdown decision sub-system 2650 (or more generally the controller 2105) may control the heating engine control circuit 2127 to cut power to the heater 336 by outputting a heater activation signal GATE_ON (FIG. 38) having a logic low level or by outputting one or more of a first heater enable signal GATE_ENB or a second heater enable signal COIL_Z (FIG. 39) having a logic low level.

In yet another example, the fault detection sub-system 2630 may determine that an idling event has occurred in accordance with the example embodiment shown in FIG. 31. In this example, in response to determining that the idling event has occurred, the fault detection sub-system 2630 may output a fault alert (idling alert) to the auto shutdown decision sub-system 2650 indicating that the idling event has occurred. In response to the fault alert, the auto shutdown decision sub-system 2650 classifies the idling event as a normal fault event, and may perform a heater off operation, a vaping off operation, an auto off operation, or the like, as needed.

Returning now to step S3706, if the fault event is not a normal fault event, then at step S3722 the auto shutdown decision sub-system 2650 determines whether the fault event is a soft fault pod event.

As discussed above, a soft fault pod event may include a temperature event in which the temperature of the non-nicotine pod assembly electrical system 2200 or a component thereof (e.g., the heater 336) exceeds a maximum temperature threshold. In a more specific example, the fault detection sub-system may determine whether a heater temperature fault event has occurred according to one or more of the example embodiments shown in FIGS. 32A and 32B. Example embodiments should not, however, be limited to these examples.

If the auto shutdown decision sub-system 2650 identifies the fault event as a soft fault pod event, then at step S372 the auto shutdown decision sub-system 2650 performs one or more consequent actions for the soft fault pod event.

For example purposes, a more detailed example will be described with regard to one or more consequent actions in response to a heater temperature fault event.

As shown in FIGS. 33A and 33B, at step S3724 the auto shutdown decision sub-system 2650 controls the heating engine control circuit 2127 to perform the heater off operation as discussed earlier and also in more detail below.

At step S3726, the auto shutdown decision sub-system 2650 logs the occurrence of the soft fault pod event in the memory 2130. In one example, the controller 2105 may store an identifier of the soft fault pod event (e.g., a heater temperature fault event) in association with an identification of the heater off operation and the time at which the soft fault pod event and heater off operation occurred.

At step S3727, the auto shutdown decision sub-system 2650 controls the vaper indicators 2135 to output an indication that the fault event (e.g., heater temperature fault event) has occurred. In one example, the indication may be in the form of a sound, visual display and/or haptic feedback to an adult vaper. For example, the indication may be a blinking red LED, a software message containing an error code that is sent (e.g., via Bluetooth) to a connected "App" on a remote electronic device.

At step S3728, the auto shutdown decision sub-system 2650 determines whether to return the non-nicotine e-vaping device 500 to normal operation (a non-fault state of the FSM). In the example in which the soft fault pod event is a heater temperature fault event, the auto shutdown decision sub-system 2650 may determine whether to return to normal operation based on whether the temperature of the heater 336 has fallen below the threshold maximum temperature value.

If the auto shutdown decision sub-system 2650 determines that the non-nicotine e-vaping device 500 should not return to normal operation (e.g., the temperature of the heater 336 has not fallen below the threshold maximum temperature value), then the process returns to step S3727, and continues to wait for an indication that the non-nicotine e-vaping device 500 should return to normal operation.

If, however, the auto shutdown decision sub-system 2650 determines that the non-nicotine e-vaping device 500 should return to normal operation at step S3728, then at step S3729 the auto shutdown decision sub-system 2650 returns the non-nicotine e-vaping device 500 to normal operation in which the non-nicotine e-vaping device 500 is ready for vaping when vaping conditions are subsequently presented (e.g., in response to application of negative pressure by an adult vaper). In the example in which the heater temperature fault event has occurred, the auto shutdown decision sub-system 2650 may control the heating engine control circuit 2127 to enable power to the heater 336 by outputting a heater activation signal GATE_ON (FIG. 38) having a logic high level or by outputting both the first heater enable signal GATE_ENB and the second heater enable signal COIL_Z (FIG. 39) having a logic high level.

Although the example embodiment shown in FIGS. 33A and 33B is discussed as including step S3728, it should be understood that this step may be omitted and the process may proceed directly from step S3727 to step S3729 in which the auto shutdown decision sub-system 2650 returns to normal operation. Because the soft fault pod events are of relatively low importance, while also intermittent and self-clearing, in a simpler implementation these faults are not actively monitored nor is any state information about them maintained within the decision system. Instead, the fault just recurs (and is handled again) if still present when vaping conditions are again presented at the non-nicotine e-vaping device. For example, if the temperature of the heater 336 is still above a threshold maximum temperature value and the adult vaper applies negative pressure to the non-nicotine e-vaping device, then the heater off operation is again performed.

Returning to step S3722, if the fault event is not a soft fault pod event, then at step S3730 the auto shutdown decision sub-system 2650 determines whether the fault event is a hard fault pod event.

As discussed above, a hard fault pod event may include an open circuit failure in the non-nicotine pod assembly electrical system 2200, depletion of non-nicotine pre-vapor formulation in the non-nicotine pod assembly 300 (pod empty), dry puff detection of the non-nicotine pod assembly 300, a combination thereof, or the like.

If the auto shutdown decision sub-system 2650 identifies the fault event as a hard fault pod event, then at step S3730 the auto shutdown decision sub-system 2650 performs one or more consequent actions for the hard fault pod event.

As shown in FIGS. 33A and 33B, in at least one example embodiment, at step S3732 the auto shutdown decision sub-system 2650 may perform the vaping off operation as discussed above with regard to step S3710 in response to a hard fault pod event.

At step S3734, the auto shutdown decision sub-system 2650 logs or stores the occurrence of the hard fault pod event in the memory 2130. The auto shutdown decision sub-system 2650 may log or store the occurrence of the hard fault pod event in the same or substantially the same manner as discussed above with regard to step S3726.

At step S3736, the auto shutdown decision sub-system 2650 controls the vaper indicators 2135 to output an indication that the hard fault pod event has occurred. The auto shutdown decision sub-system 2650 may control the vaper indicators 2135 to output an indication in the same or substantially the same manner as discussed above with regard to step S3727.

At step S3738, the auto shutdown decision sub-system 2650 determines whether corrective action has been taken (e.g., by an adult vaper within a threshold time period after the hard fault pod event is detected) in response to the hard fault pod event. Corrective action may include removing the non-nicotine pod assembly 300 from the device body 100 within (prior to expiration of) a removal threshold time interval after (e.g., in response to) indicating the hard fault pod event to the adult vaper.

In this example, the auto shutdown decision sub-system 2650 may determine that the non-nicotine pod assembly 300 has been removed from the device body 100 digitally by checking that the set of five contacts 326 of the non-nicotine pod assembly 300 have been removed. In another example, the auto shutdown decision sub-system 2650 may determine that the non-nicotine pod assembly 300 has been removed from the device body 100 by sensing that the electrical contacts 324_a_, 324_b_ and/or 326 of the non-nicotine pod assembly 300 have been disconnected from the device electrical connector 132 of the device body 100.

If the auto shutdown decision sub-system 2650 determines that corrective action has been taken (e.g., the non-nicotine pod assembly 300 has been removed from the device body 100 within the removal threshold time interval after indicating the hard fault pod event), then the process proceeds to step S3729 and continues as discussed above. In this case, although energy to the heater 336 is still disabled because the non-nicotine pod assembly 300 has been removed, the non-nicotine e-vaping device 500 is otherwise ready to vape in response to application of negative pressure by an adult vaper once a new non-nicotine pod assembly has been inserted.

If the auto shutdown decision sub-system 2650 determines that the non-nicotine pod assembly 300 is not removed within the removal threshold time interval (corrective action has not been taken within the threshold time interval), then the auto shutdown decision sub-system 2650 outputs another one or more control signals to perform the auto off operation.

By performing the auto-off operation, discharge of the power supply 2110 of the non-nicotine e-vaping device 500 resulting from displaying the fault for a prolonged period may be prevented.

Returning to step S3730, if the fault event is not a hard fault pod event, then at step S3742 the auto shutdown decision sub-system 2650 determines whether the fault event is a soft fault device event. As mentioned above, an example of a soft fault device event may be a power supply low voltage fault event when the voltage or charge of the power supply 2110 falls below a minimum threshold level. In this example, the fault detection sub-system 2630 may determine that a power supply low voltage fault event has occurred, and output a fault alert to the auto shutdown decision sub-system 2650 indicating the occurrence of the power supply low voltage fault event. In response to the fault alert, the auto shutdown decision sub-system 2650 classifies the power supply low voltage fault event as a soft fault device event. More generally, the fault detection sub-system 2630 may output a soft fault device event alert to the auto shutdown decision sub-system 2650 indicating that the soft fault device event has occurred at the non-nicotine e-vaping device 500.

If the auto shutdown decision sub-system 2650 identifies the fault event as a soft fault device event, then at step S374 the auto shutdown decision sub-system 2650 performs one or more consequent actions for the soft fault device event.

As shown in FIGS. 33A and 33B, in at least one example embodiment, at step S3744 the auto shutdown decision sub-system 2650 outputs one or more device power state signals to initiate/perform the vaping off operation and/or the auto off operation. The auto shutdown decision sub-system 2650 may determine whether to initiate the vaping off operation and/or the auto off operation based on the current voltage of the power supply. For example, if the voltage of the power supply 2110 is less than a first threshold level, then the auto shutdown decision sub-system 2650 may initiate the vaping off operation. If, however, the voltage of the power supply 2110 falls below a second threshold level, which is lower than the first threshold level, then the auto shutdown decision sub-system 2650 may initiate the auto off operation.

At step S3746, the auto shutdown decision sub-system 2650 logs or stores the occurrence of the soft fault device event in the memory 2130. The auto shutdown decision sub-system 2650 may log or store the occurrence of the soft fault device event in the same or substantially the same manner as discussed above with regard to step S3726.

At step S3748, the auto shutdown decision sub-system 2650 controls the vaper indicators 2135 to output an indication that the soft fault device event has occurred. The auto shutdown decision sub-system 2650 may control the vaper indicators 2135 to output an indication in the same or substantially the same manner as discussed above with regard to step S3727.

At step S3750, the auto shutdown decision sub-system 2650 determines whether corrective action has been taken (e.g., by an adult vaper within a threshold time interval) in response to the soft fault device event. In the example in which the soft fault device event is a power supply low voltage fault event, corrective action may include charging of the power supply 2110 above the first threshold level.

If the auto shutdown decision sub-system 2650 determines that corrective action has been taken (e.g., voltage of the power supply 2110 has increased above the first (minimum) threshold level), then the process proceeds to step S3729 at which the non-nicotine e-vaping device 500 returns to normal operation. In this case, the auto shutdown decision sub-system 2650 may allow the controller 2105 to exit the sleep state (e.g., if the auto off operation is performed) and/or enable vaping functions at the non-nicotine e-vaping device 500 as discussed above with regard to step S3729.

Returning to step S3750, if corrective action is not taken in response to the soft fault device event, then the process returns to S3748 and the indication of the soft fault device event is continually output to the adult vaper until corrective action is taken or the non-nicotine e-vaping device 500 is powered off manually. In case the auto off operation is initiated at step S3744, the indication of the soft fault device event may be repeatedly output via the vaper indicators 2135 in response to interaction with the non-nicotine e-vaping device 500 by an adult vaper (e.g., pressing one or more buttons on the device) until corrective action is taken.

Returning to step S3742, if the auto shutdown decision sub-system 2650 determines that the fault event is not a soft fault device event, then the auto shutdown decision sub-system 2650 determines that the fault event is a hard fault device event at step S3754. As discussed above, hard fault device events may include power supply charging failure events, the presence of current flowing through the heater when not in a vaping state ('unexpected heater current'), and power supply temperature faults indicating that the temperature of the power supply 2110 is outside an acceptable range, a combination thereof, or the like. An 'unexpected heater current' is a hard fault device event in which the software (or hardware) has left the heater 336 energized (e.g., after vaping conditions are no longer present at the non-nicotine e-vaping device 500), and is an example of why the non-nicotine e-vaping device 500 is reset at step S3768 as part of its consequent actions.

According to at least one example embodiment, the auto shutdown decision sub-system 2650 may determine that a power supply temperature fault has occurred based on whether an estimated temperature of the power supply 2110 is greater than or equal to a maximum power supply temperature threshold value or less than or equal to a minimum power supply temperature threshold value. The auto shutdown decision sub-system 2650 may estimate the temperature of the power supply 2110 based on output from the power supply temperature measurement circuit 21254, which will be discussed in more detail later.

If the auto shutdown decision sub-system 2650 identifies the fault event as a hard fault device event, then at step S376 the auto shutdown decision sub-system 2650 performs one or more consequent actions for the hard fault device event.

As shown in FIGS. 33A and 33B, in at least one example embodiment, in response to the hard fault device event, at step S3756 the auto shutdown decision sub-system 2650 initiates/performs one or more of the vaping off operation, the charger stop operation and/or the auto off operation.

At step S3758, the auto shutdown decision sub-system 2650 logs or stores the occurrence of the hard fault device event in the memory 2130. The auto shutdown decision sub-system 2650 may log or store the occurrence of the hard fault device event in the same or substantially the same manner as discussed above with regard to step S3726.

At step S3760, the auto shutdown decision sub-system 2650 initiates a reset timer. The reset timer may be a time interval after which the auto shutdown decision sub-system 2650 causes the non-nicotine e-vaping device 500 to perform a soft (software) reset. In this case, the reset timer may be countdown timer executed utilizing the clock circuit 2128.

At step S3762, the auto shutdown decision sub-system 2650 controls the vaper indicators 2135 to output an indication that the hard fault device event has occurred. The auto shutdown decision sub-system 2650 may control the vaper indicators 2135 to output an indication in the same or substantially the same manner as discussed above with regard to step S3727.

After outputting the indication, at step S3764 the auto shutdown decision sub-system 2650 determines whether the reset timer initiated at step S3760 has lapsed at step S3764.

If the reset timer has lapsed, then at step S3768 the auto shutdown decision sub-system 2650 performs a soft reset of the non-nicotine e-vaping device 500 in an effort to clear the hard fault device event. The soft reset may include closing all software applications running on the controller 2105, possibly clearing the Random Access Memory (RAM) and/or any persistent memory, and restarting the non-nicotine e-vaping device 500.

Although discussed with regard to a soft reset, the reset at step S3768 may be a soft (software) reset, a hard (hardware) reset, or a power on reset (POR).

After performing the soft reset, at step S3770 the auto shutdown decision sub-system 2650 determines whether the hard fault device event has been cleared (e.g., the soft reset has corrected the fault state).

If the hard fault device event has been cleared by the soft reset at step S3768, then the process proceeds to step S3729 and the auto shutdown decision sub-system 2650 returns the non-nicotine e-vaping device 500 to normal operation, for example, by enabling charging, enabling vaping, etc., as needed.

According to one or more example embodiments, the hard fault device event may at least cover unexpected cases (e.g., software crashes), which are generally only recoverable by performing a reset.

Returning to step S3770, if the hard fault device event has not been cleared by the soft reset at step S3768, then at step S3772 the auto shutdown decision sub-system 2650 causes the non-nicotine e-vaping device 500 to shutdown. In this example, similar to the auto off operation, the auto shutdown decision sub-system 2650 may output one or more device power state signals to the sub-systems of the non-nicotine e-vaping device 500 to power down the non-nicotine e-vaping device 500.

According to at least one example embodiment, the reset at step S3768 may be attempted three times before shutting down the non-nicotine e-vaping device 500 at step S3772.

According to at least some other example embodiments, if three reset attempts do not clear the hard fault device event, then the auto shutdown decision sub-system 2650 may set a persistent bit in memory that prevents the non-nicotine e-vaping device 500 from turning on.

Returning now to step S3764, if the reset timer has not lapsed, then the auto shutdown decision sub-system 2650 determines whether corrective action has been taken at step S3766.

In the example in which the hard fault device event is a power supply temperature fault, corrective action may include moving the non-nicotine e-vaping device 500 to a warmer location (in case the power supply temperature falls below a minimum threshold value), or moving the non-nicotine e-vaping device 500 to a cooler location (in case the power supply temperature rises above a maximum threshold value). In this example, the auto shutdown decision sub-system 2650 may determine whether the corrective action has been taken based on whether the temperature of the power supply 2110 rises or falls as necessary.

If corrective action has been taken, then the process proceeds to step S3729 and continues as discussed above.

Returning to step S3766, if the reset timer has not lapsed and corrective action has not yet been taken, then the process returns to S3762 and the indication of the hard fault device event is continually output until corrective action is taken or the non-nicotine e-vaping device 500 is powered off manually. The process then continues as discussed herein.

Figure 34:
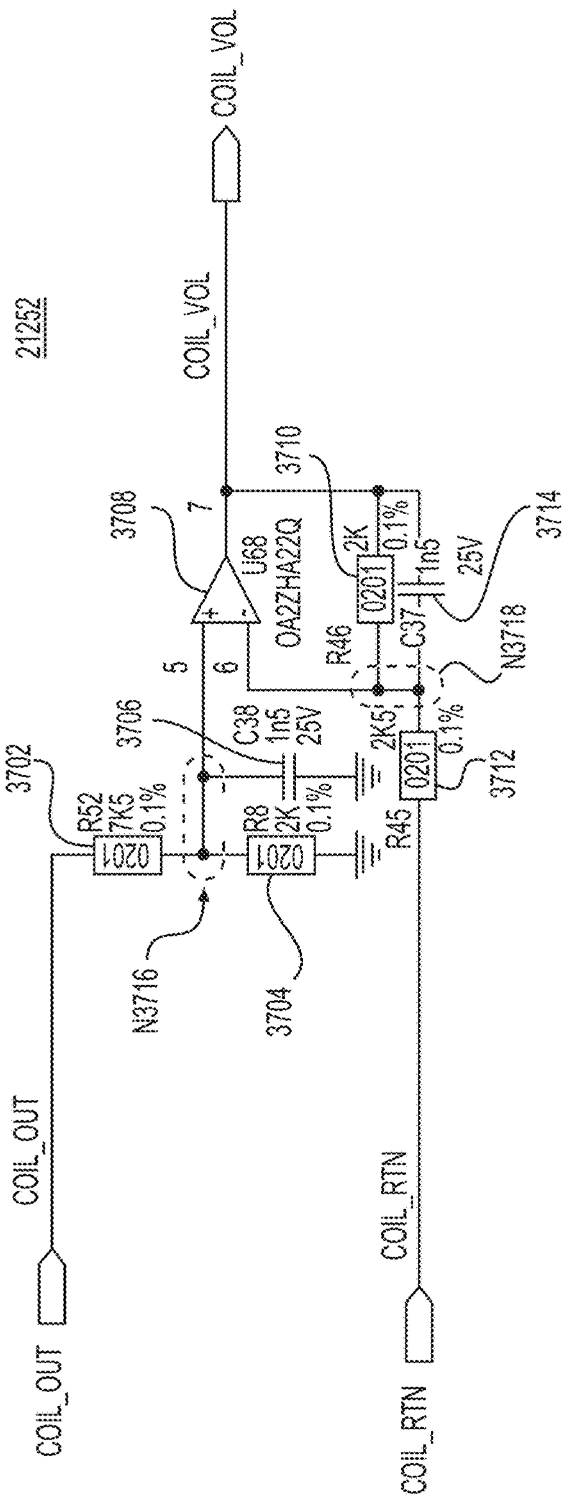
FIG. 34 illustrates an example embodiment of the heater voltage measurement circuit 21252.

FIG. 34 illustrates an example embodiment of the heater voltage measurement circuit 21252.

Referring to FIG. 34, the heater voltage measurement circuit 21252 includes a resistor 3702 and a resistor 3704 connected in a voltage divider configuration between a terminal configured to receive an input voltage signal COIL_OUT and ground. The input voltage signal COIL_OUT is the voltage input to (voltage at the input terminal of) the heater 336. A node N3716 between the resistor 3702 and the resistor 3704 is coupled to a positive input of an operational amplifier (Op-Amp) 3708. A capacitor 3706 is connected between the node N3716 and ground to form a low-pass filter circuit (an R/C filter) to stabilize the voltage input to the positive input of the Op-Amp 3708. The filter circuit may also reduce inaccuracy due to switching noise induced by PWM signals used to energize the heater 336, and have the same phase response/group delay for both current and voltage.

The heater voltage measurement circuit 21252 further includes resistors 3710 and 3712 and a capacitor 3714. The resistor 3712 is connected between node N3718 and a terminal configured to receive an output voltage signal COIL_RTN. The output voltage signal COIL_RTN is the voltage output from (voltage at the output terminal of) the heater 336.

Resistor 3710 and capacitor 3714 are connected in parallel between node N3718 and an output of the Op-Amp 3708. A negative input of the Op-Amp 3708 is also connected to node N3718. The resistors 3710 and 3712 and the capacitor 3714 are connected in a low-pass filter circuit configuration.

The heater voltage measurement circuit 21252 utilizes the Op-Amp 3708 to measure the voltage differential between the input voltage signal COIL_OUT and the output voltage signal COIL_RTN, and output a scaled heater voltage measurement signal COIL_VOL that represents the voltage across the heater 336. The heater voltage measurement circuit 21252 outputs the scaled heater voltage measurement signal COIL_VOL to an ADC pin of the controller 2105 for digital sampling and measurement by the controller 2105.

The gain of the Op-Amp 3708 may be set based on the surrounding passive electrical elements (e.g., resistors and capacitors) to improve the dynamic range of the voltage measurement. In one example, the dynamic range of the Op-Amp 3708 may be achieved by scaling the voltage so that the maximum voltage output matches the maximum input range of the ADC (e.g., about 1.8V). In at least one example embodiment, the scaling may be about 267 mV per V, and thus, the heater voltage measurement circuit 21252 may measure up to about 1.8V/0.267V=6.74V.

Figure 35:
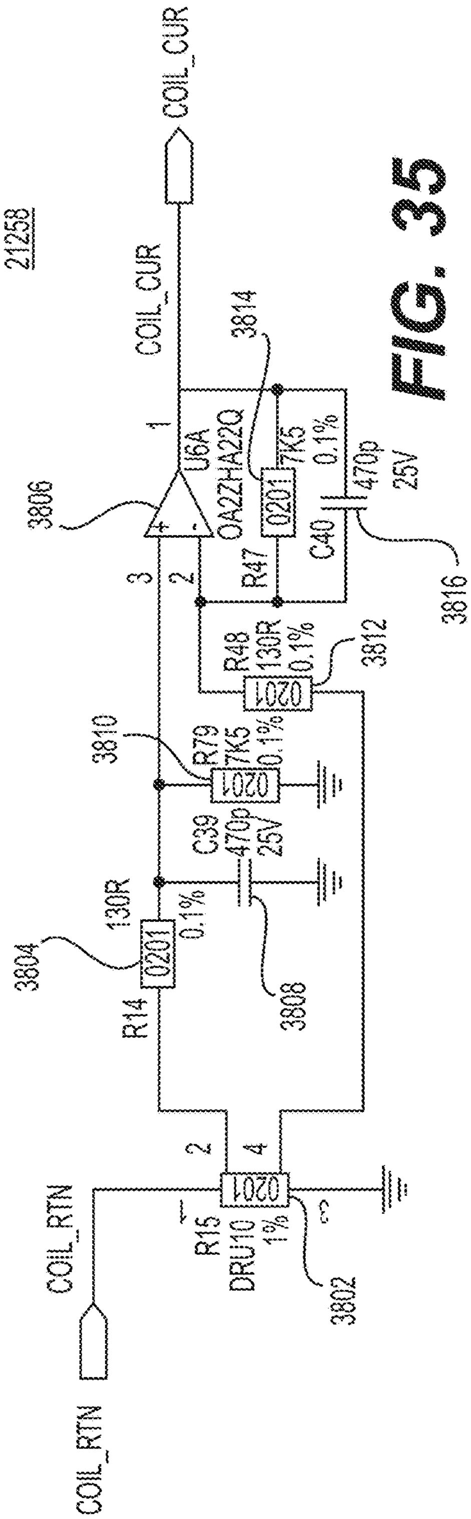
FIG. 35 illustrates an example embodiment of the heater current measurement circuit 21258 shown in FIG. 29.

FIG. 35 illustrates an example embodiment of the heater current measurement circuit 21258 shown in FIG. 29.

Referring to FIG. 35, the output voltage signal COIL_RTN is input to a four terminal (4T) measurement resistor 3802 connected to ground. The differential voltage across the four terminal measurement resistor 3802 is scaled by an Op-Amp 3806, which outputs a heater current measurement signal COIL_CUR indicative of the current through the heater 336. The heater current measurement signal COIL_CUR is output to an ADC pin of the controller 2105 for digital sampling and measurement of the current through the heater 336 at the controller 2105.

In the example embodiment shown in FIG. 35, the four terminal measurement resistor 3802 may be used to reduce error in the current measurement using a 'Kelvin Current Measurement' technique. In this example, separation of the current measurement path from the voltage measurement path may reduce noise on the voltage measurement path.

The gain of the Op-Amp 3806 may be set to improve the dynamic range of the measurement. In this example, the scaling of the Op-Amp 3806 may be about 0.577 V/A, and thus, the heater current measurement circuit 21258 may measure up to about $$\frac{1.8\ \text{V}}{0.577\ \text{V/A}} = 3.12\ \text{A}.$$

Referring to FIG. 35 in more detail, a first terminal of the four terminal measurement resistor 3802 is connected to a terminal of the heater 336 to receive the output voltage signal COIL_RTN. A second terminal of the four terminal measurement resistor 3802 is connected to ground. A third terminal of the four terminal measurement resistor 3802 is connected to a low-pass filter circuit (R/C filter) including resistor 3804, capacitor 3808 and resistor 3810. The output of the low-pass filter circuit is connected to a positive input of the Op-Amp 3806. The low-pass filter circuit may reduce inaccuracy due to switching noise induced by the PWM signals applied to energize the heater 336, and may also have the same phase response/group delay for both current and voltage.

The heater current measurement circuit 21258 further includes resistors 3812 and 3814 and a capacitor 3816. The resistors 3812 and 3814 and the capacitor 3816 are connected to the fourth terminal of the four terminal measurement resistor 3802, a negative input of the Op-Amp 3806 and an output of the Op-Amp 3806 in a low-pass filter circuit configuration, wherein the output of the low-pass filter circuit is connected to the negative input of the Op-Amp 3806.

The Op-Amp 3806 outputs a differential voltage as the heater current measurement signal COIL_CUR to an ADC pin of the controller 2105 for sampling and measurement of the current through the heater 336 by the controller 2105.

According to at least this example embodiment, the configuration of the heater current measurement circuit 21258 is similar to the configuration of the heater voltage measurement circuit 21252, except that the low-pass filter circuit including resistors 3804 and 3810 and the capacitor 3808 is connected to a terminal of the four terminal measurement resistor 3802 and the low-pass filter circuit including the resistors 3812 and 3814 and the capacitor 3816 is connected to another terminal of the four terminal measurement resistor 3802.

The controller 2105 may average multiple samples (e.g., of voltage) over a time window (e.g., about 1 ms) corresponding to the 'tick' time used in the non-nicotine e-vaping device 500, and convert the average to a mathematical representation of the voltage and current across the heater 336 through application of a scaling value. The scaling value may be determined based on the gain settings implemented at the respective Op-Amps, which may be specific to the hardware of the non-nicotine e-vaping device 500.

The controller 2105 may filter the converted voltage and current measurements using, for example, a three tap moving average filter to attenuate measurement noise. The controller 2105 may then use the filtered measurements to calculate: resistance $R_{HEATER}$ of the heater 336

$$\left(R_{HEATER} = \frac{V_{HEATER}}{I_{HEATER}}\right),$$

power $P_{HEATER}$ applied to the heater 336

$$(P_{HEATER} = V_{HEATER} * I_{HEATER}),$$

power supply current $$\left(I_{BATT} = \frac{P_{in}}{V_{BATT}}\right),$$

where $$\left(P_{in} = P_{HEATER} * \frac{1}{\text{Efficiency}}\right),$$

or the like. Efficiency is the ratio of power $P_{in}$ delivered to the heater 336 across all operating conditions. In one example, Efficiency may be at least 85%.

According to one or more example embodiments, the gain settings of the passive elements of the circuits shown in FIGS. 34 and/or 35 may be adjusted to match the output signal range to the input range of the controller 2105.

The fault detection sub-system 2630 may utilize the heater voltage measurements and/or the heater current measurements to determine, for example, whether a hard fault pod event such as an open circuit failure in the heater 336 has occurred.

Figure 36:
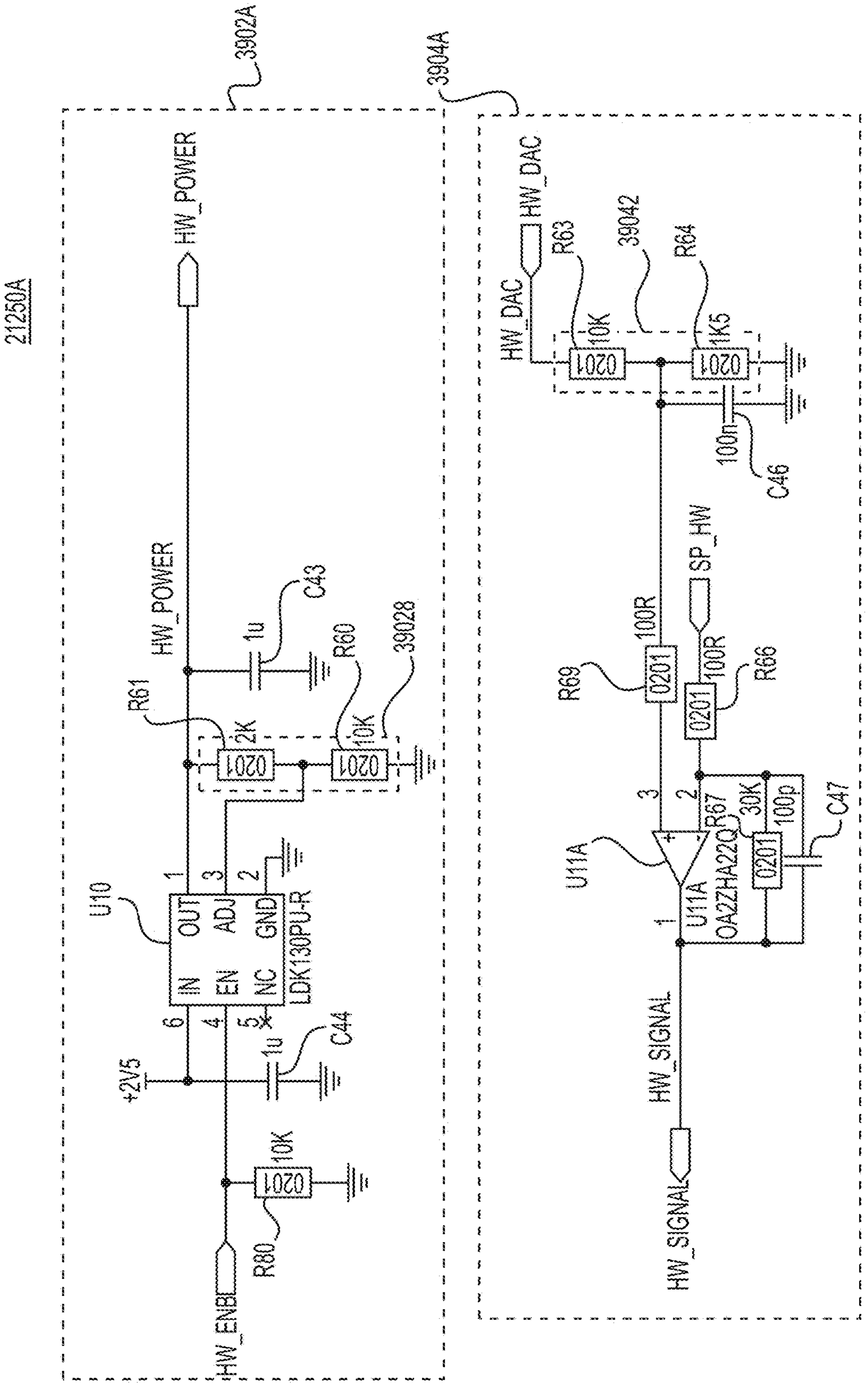
FIG. 36 illustrates a pod temperature measurement circuits according to an example embodiment.
Figure 37:
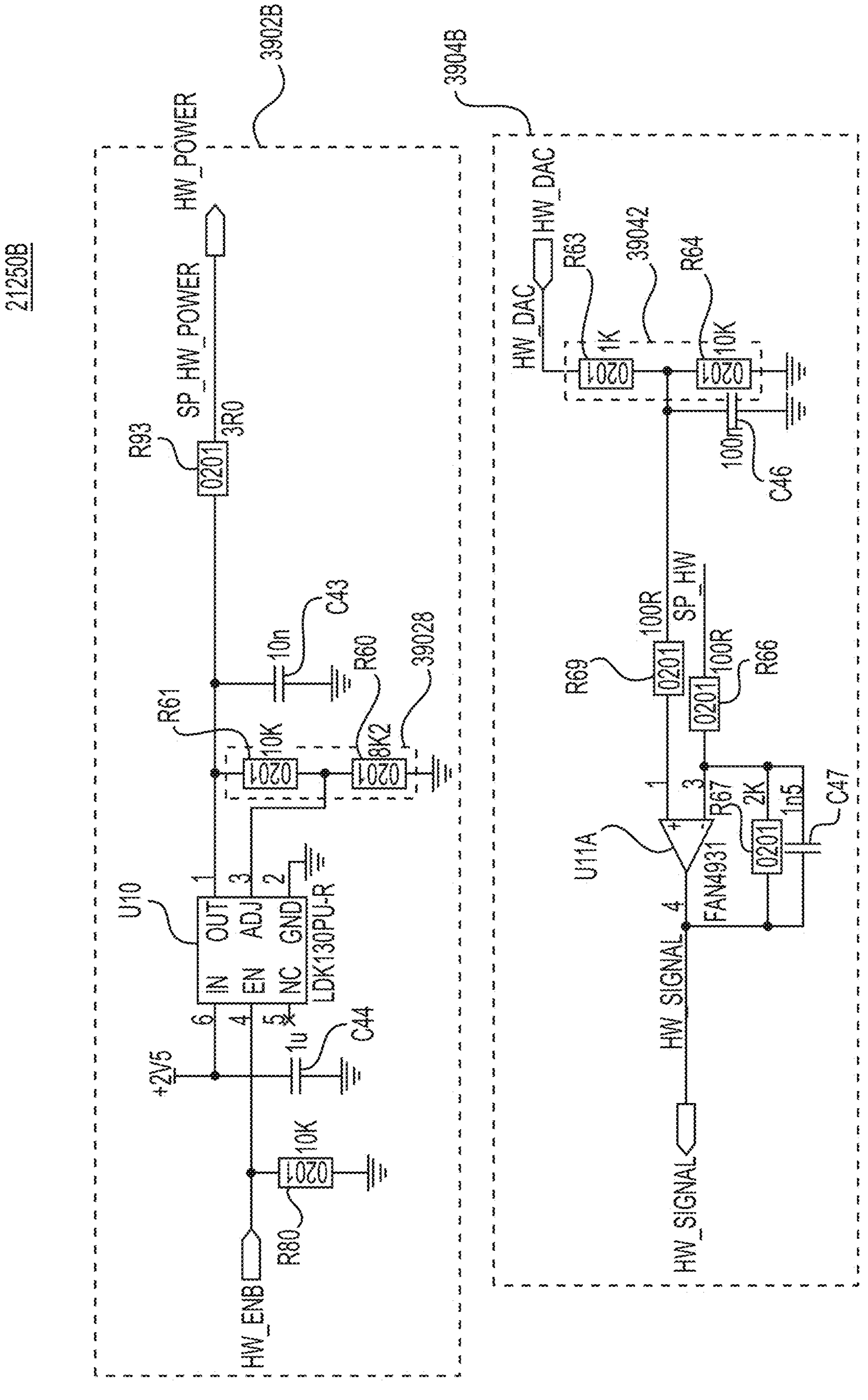
FIG. 37 illustrates a pod temperature measurement circuits according to another example embodiment.

FIGS. 36 and 37 illustrate pod temperature measurement circuits according to example embodiments.

Referring to FIG. 36, the pod temperature measurement circuit 21250A includes a driver stage 3902A and a measurement stage 3904A. The driver stage 3902A is configured to generate a pod temperature measurement power signal HW_POWER to deliver power to the pod sensor 2220 in response to a pod temperature measurement control signal HW_ENB. The pod temperature measurement power signal HW_POWER may be a PWM signal. The measurement stage 3904A is configured to generate a pod temperature measurement output signal HW_SIGNAL based on a DAC comparison signal HW_DAC from the DAC (not shown) at the controller 2105 and a pod sensor signal SP_HW from the pod sensor 2220. The pod temperature measurement output signal HW_SIGNAL may be a differential voltage signal indicative of a temperature of one or more elements (e.g., the heater 336) of the non-nicotine pod assembly 300. Input to and output from an example embodiment of a pod sensor 2220 will be discussed in more detail later.

In more detail with regard to FIG. 36, the driver stage 3902A receives the pod temperature measurement control signal HW_ENB from the controller 2105. In this example, the pod temperature measurement control signal HW_ENB may be a PWM signal having a duty cycle regulated by the controller 2105 to vary power based on the pod sensor signal SP_HW from the pod sensor 2220. When the pod temperature measurement control signal HW_ENB is asserted (active), the driver stage 3902A may be enabled and output the pod temperature measurement power signal HW_POWER, otherwise the output of the driver stage 3902A may be disabled.

The pod temperature measurement control signal HW_ENB is input into an enable pin EN of a Low Dropout voltage regulator (LDO) U10, which translates the pod temperature measurement control signal HW_ENB, which is a low current drive strength processor signal, into the pod temperature measurement power signal HW_POWER, which is a high current drive strength PWM signal.

A resistor R80 is connected as a pull-down resistor between the enable pin EN of the LDO U10 and ground to ensure that the output of the driver stage 3902A is disabled if the pod temperature measurement control signal HW_ENB is in an indeterminate state.

The driver stage 3902A further includes capacitors C43 and C44. Capacitor C44 is connected to an input pin IN of the LDO U10 and a voltage source to provide a reservoir and filter, which may improve the speed at which the pod temperature measurement power signal HW_POWER reaches its ON voltage. The capacitor C43 is connected between the output pin and ground to provide filtering and a reservoir for the pod temperature measurement power signal HW_POWER.

Resistors R60 and R61 form a feedback network 39028 in the form of a voltage divider circuit. The feedback network 39028 outputs a feedback voltage to an adjustment or feedback terminal ADJ of the LDO U10. The LDO U10 sets the precision voltage output of the pod temperature measurement power signal HW_POWER based on the feedback voltage input to the feedback terminal ADJ. According to at least some example embodiments, the relationship between precision voltage output for the pod temperature measurement power signal HW_POWER and the feedback voltage $V_{ADJ}$ output is given by $$V_{HW\_POWER} = V_{ADJ}\left(1 + \frac{R_{61}}{R_{60}}\right).$$

In this example, the resistances of resistors R60 and R61 have known resistances, and the voltage $V_{ADJ}$ is also known based on the type of the LDO U10.

At the measurement stage 3904A, the pod sensor signal SP_HW from the pod sensor 2220 is input to the negative input of an Op-Amp U11A via resistor R66 to gain scale the voltage of the pod sensor signal SP_HW for measurement by the ADC at the controller 2105. The Op-Amp U11A is an inverting amplifier with a gain set according to the resistance of resistor R66 and a resistance of resistor R67, which is connected between the negative input and the output of the Op-Amp U11A. The capacitor C47 is connected in parallel with resistor R67 to form a low-pass filter circuit to filter out high-frequency noise from the pod sensor signal SP_HW.

The DAC comparison signal HW_DAC from the DAC at the controller 2105 is input to the positive input of the Op-Amp U11A through a voltage divider circuit 39042 including resistors R63 and R64. The DAC comparison signal HW_DAC sets a reference voltage level for the Op-Amp U11A, which in effect selects the differential voltage applied to the Op-Amp U11A and suppresses or prevents saturation of the Op-Amp U11A. In other words, the DAC comparison signal HW_DAC sets an operating point for the Op-Amp U11A to suppress saturation of the pod temperature measurement output signal HW_SIGNAL output by the Op-Amp U11A. The voltage divider circuit 39042 reduces each DAC step in voltage to provide finer control of the range setting. The ratio of the resistors R63 and R64 may approximate the balance resistor and pod sensor 2220 (e.g., at its max temperature). A capacitor C46 is connected in parallel with the resistor R64 to form a low-pass filter circuit to filter out noise from the DAC comparison signal HW_DAC. A resistor R69 is connected between the output of the voltage divider circuit 39042 and the positive input of the Op-Amp U11A.

The pod sensor signal SP_HW from the pod sensor 2220 may have a relatively small voltage level (e.g., about 2 mV), and thus, the relatively high gain of the Op-Amp U11A may be used to match the pod temperature measurement signal HW_SIGNAL to the dynamic signal range of the ADC at the controller 2105 (e.g., about 1.8V). Accordingly, the Op-Amp U11A amplifies the pod sensor signal SP_HW and outputs the amplified signal as the pod temperature measurement output signal HW_SIGNAL to the ADC for sampling and measurement at the controller 2105.

Referring to FIG. 37, the pod temperature measurement circuit 21250B includes a driver stage 3902B and a measurement stage 3904B. In the example embodiment shown in FIG. 37, the driver stage 3902B and the measurement stage 3904B are similar to the driver stage 3902A and the measurement stage 3904A, respectively, shown in FIG. 36, except that the driver stage 3902B further includes a measurement balancing resistor R93 and the capacitance of the capacitor C43 may be reduced in value to increase the rise/fall time of the pod sensor signal SP_HW. In at least one example, the measurement balancing resistor R93 may have a resistance of about 3 Ohms and may be moved from the non-nicotine pod assembly electrical system 2200 to the device body electrical system 2100 to reduce cost of the non-nicotine pod assembly 300. Additionally, in at least the example embodiment shown in FIG. 37, the passive elements may be arranged and adjusted to configure the gain settings such that the output signal range is matched to the input signal range of the controller 2105.

According to one or more example embodiments, the fault detection sub-system 2630 may utilize the temperature measurements at the controller 2105 to, for example, estimate a temperature of the heater 336 or other portion of the non-nicotine pod assembly 300 and determine whether a soft fault pod event (e.g., a heater temperature fault event) has occurred.

Figure 38:
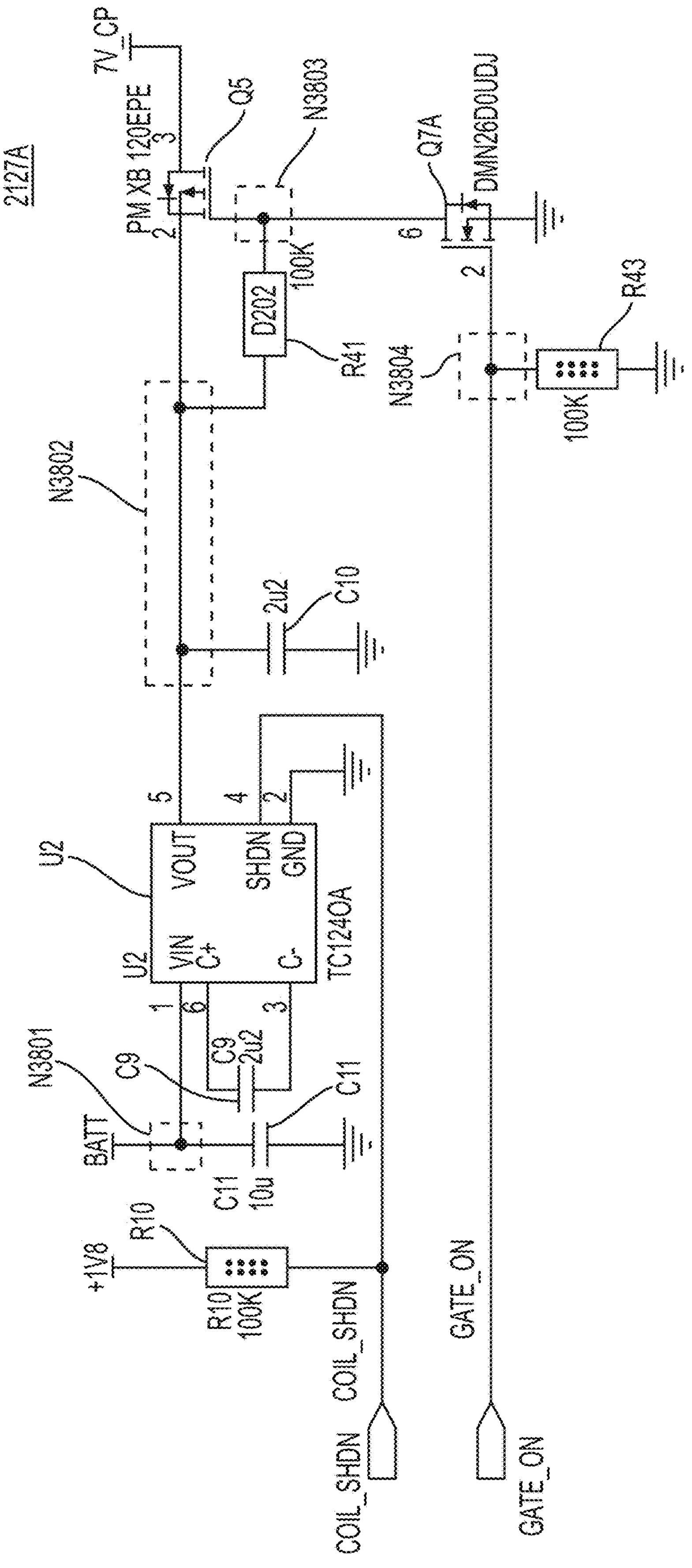
FIG. 38 is a circuit diagram illustrating a heating engine control circuit according to an example embodiment.
Figure 39:
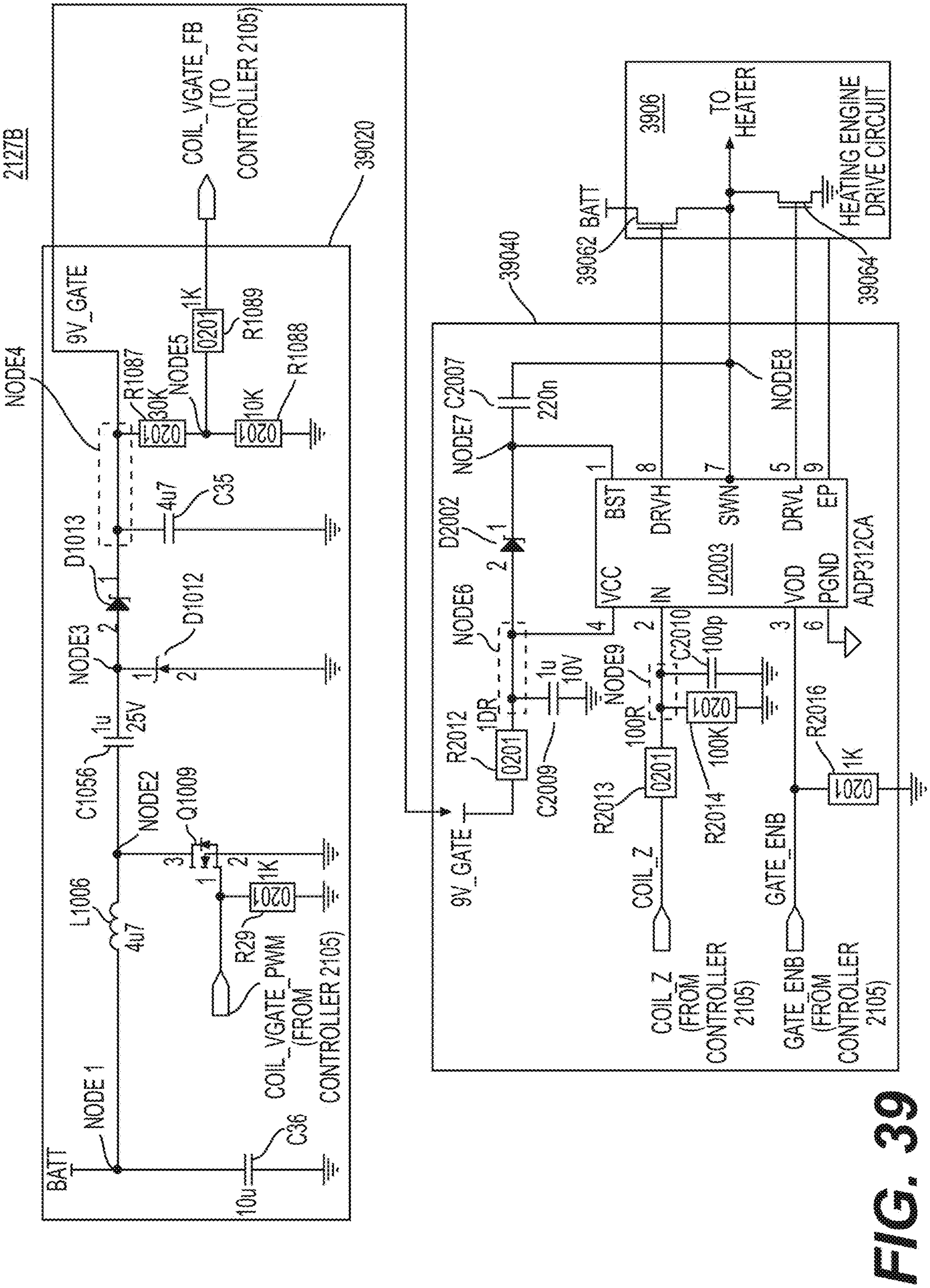
FIG. 39 is a circuit diagram illustrating another heating engine control circuit according to an example embodiment.

FIG. 38 is a circuit diagram illustrating a heating engine control circuit according to an example embodiment. The heating engine control circuit shown in FIG. 38 is an example of the heating engine control circuit 2127 shown in FIG. 29.

Referring to FIG. 38, the heating engine control circuit 2127A includes a CMOS charge pump U2 configured to supply a power rail (e.g., about 7V power rail (7V_CP)) to one or more gate driver integrated circuits (ICs) to control the power FETs (heater power control circuitry, also referred to as a heating engine drive circuit or circuitry, not shown in FIG. 38) that energize the heater 336 in the non-nicotine pod assembly 300.

In example operation, the charge pump U2 is controlled (selectively activated or deactivated) based on the vaping shutdown signal COIL_SHDN (device power state signal; also referred to as a vaping enable signal) from the controller 2105. In the example shown in FIG. 38, the charge pump U2 is activated in response to output of the vaping shutdown signal COIL_SHDN having a logic low level, and deactivated in response to output of the coil shutdown signal COIL-SHDN having a logic high level. Once the power rail 7V_CP has stabilized after activation of the charge pump U2 (e.g., after a settling time interval has expired), the controller 2105 may enable the heater activation signal GATE_ON to provide power to the heater power control circuitry and the heater 336.

According to at least one example embodiment, the controller 2105 (or auto shutdown decision sub-system 2650) may perform the vaping off operation by outputting (enabling) the vaping shutdown signal COIL_SHDN having a logic high level to disable all power to the heater 336 until the vaping shutdown signal COIL_SHDN is disabled (transitioned to a logic low level) by the controller 2105.

The controller 2105 may output the heater activation signal GATE_ON (another device power state signal) having a logic high level in response to detecting the presence of vaping conditions at the non-nicotine e-vaping device 500. In this example embodiment, the transistors (e.g., field-effect transistors (FETs)) Q5 and Q7A' are activated when the controller 2105 enables the heater activation signal GATE_ON to the logic high level. The controller 2105 may output the heater activation signal GATE_ON having a logic low level to disable power to the heater 336, thereby performing a heater off operation.

If a power stage fault event (a hard fault device event) occurs, where the transistors Q5 and Q7A' are unresponsive to the heater activation signal GATE_ON, then the controller 2105 may perform the vaping off operation by outputting the vaping shutdown signal COIL_SHDN having a logic high level to cut-off power to the gate driver, which in turn also cuts off power to the heater 336.

In another example, if the controller 2105 fails to boot properly resulting in the vaping shutdown signal COIL_SHDN having an indeterminate state (boot fault), then the heating engine control circuit 2127A automatically pulls the vaping shutdown signal COIL_SHDN to a logic high level to automatically cut-off power to the heater 336.

In more detail with regard to FIG. 38, capacitor C9, charge pump U2 and capacitor C10 are connected in a positive voltage doubler configuration. The capacitor C9 is connected between pins C− and C+ of the charge pump U2 and serves as a reservoir for the charge pump U2. The input voltage pin VIN of the charge pump U2 is connected to voltage source BATT at node N3801, and capacitor C10 is connected between ground and the output voltage pin VOUT of the charge pump U2 at node N3802. The capacitor C10 provides a filter and reservoir for the output from the charge pump U2, which may ensure a more stable voltage output from the charge pump U2.

The capacitor C11 is connected between node N3801 and ground to provide a filter and reservoir for the input voltage to the charge pump U2.

Resistor R10 is connected between a positive voltage source and the shutdown pin SHDN. The resistor R10 serves as a pull-up resistor to ensure that the input to the shutdown pin SHDN is high, thereby disabling the output (VOUT) of the charge pump U2 and cutting off power to the heater 336, when the vaping shutdown signal COIL_SHDN is in an indeterminate state.

Resistor R43 is connected between ground and the gate of the transistor Q7A' at node N3804. The resistor R43 serves as a pull-down resistor to ensure that the transistor Q7A' is in a high impedance (OFF) state, thereby disabling power rail 7V_CP and cutting off power to the heater 336, if the heater activation signal GATE_ON is in an indeterminate state.

Resistor R41 is connected between node N3802 and node N3803 between the gate of the transistor Q5 and the drain of the transistor Q7A'. The resistor R41 serves as a pull-down resistor to ensure that the transistor Q5 switches off more reliably.

Transistor Q5 is configured to selectively isolate the power rail 7V_CP from the VOUT pin of charge pump U2. The gate of the transistor Q5 is connected to node N3803, the drain of the transistor Q5 is connected to the output voltage terminal VOUT of the charge pump U2 at node N3802, and the source of the transistor Q5 serves as the output terminal for the power rail 7V_CP. This configuration allows the capacitor C10 to reach an operating voltage more quickly by isolating the load, and creates a fail-safe insofar as the vaping shutdown signal COIL_SHDN and heater activation signal GATE_ON must both be in the correct state to provide power to the heater 336.

Transistor Q7A is configured to control operation of the transistor Q5 based on the heater activation signal GATE_ON. For example, when the heater activation signal GATE_ON is logic high level (e.g., above ~2V), the transistor Q7A in is in its low impedance (ON) state, which pulls the gate of the transistor Q5 to ground thereby resulting in the transistor Q5 transitioning to a low impedance (ON) state. In this case, the heating engine control circuit 2127A outputs the power rail 7V_CP to the heating engine drive circuit (not shown), thereby enabling power to the heater 336.

If the heater activation signal GATE_ON has a logic low level, then transistor Q7A transitions to a high impedance (OFF) state, which results in discharge of the gate of the transistor Q5 through resistor R41, thereby transitioning the transistor Q5 into a high impedance (OFF) state. In this case, the power rail 7V_CP is not output and power to the heating engine drive circuit (and heater 336) is cut-off.

In the example shown in FIG. 38, since the transistor Q5 requires a gate voltage as high as the source voltage (~7V) to be in the high impedance (OFF) state, the controller 2105 does not control the transistor Q5 directly. The transistor Q7A provides a mechanism for controlling the transistor Q5 based on a lower voltage from the controller 2105.

FIG. 39 is a circuit diagram illustrating another heating engine control circuit according to an example embodiment. The heating engine control circuit shown in FIG. 39 is another example of the heating engine control circuit 2127 shown in FIG. 29.

Referring to FIG. 39, the heating engine control circuit 2127B includes a rail converter circuit 39020 (also referred to as a boost converter circuit) and a gate driver circuit 39040. The rail converter circuit 39020 is configured to output a voltage signal 9V_GATE (also referred to as a power signal or input voltage signal) to power the gate driver circuit 39040 based on the vaping enable signal COIL_VGATE_PWM (also referred to as a vaping shutdown signal). The rail converter circuit 39020 may be software defined, with the vaping enable signal COIL_VGATE_PWM used to regulate the 9V_GATE output.

The gate driver circuit 39040 utilizes the input voltage signal 9V_GATE from the rail converter circuit 39020 to drive the heating engine drive circuit 3906.

In the example embodiment shown in FIG. 39, the rail converter circuit 39020 generates the input voltage signal 9V_GATE only if the vaping enable signal COIL_VGATE_PWM is asserted (present). The controller 2105 may disable the 9V rail to cut power to the gate driver circuit 39040 by de-asserting (stopping or terminating) the vaping enable signal COIL_VGATE_PWM. Similar to the vaping shutdown signal COIL_SHDN in the example embodiment shown in FIG. 38, the vaping enable signal COIL_VGATE_PWM may serve as a device state power signal for performing a vaping off operation at the non-nicotine e-vaping device 500. In this example, the controller 2105 may perform a vaping off operation by de-asserting the vaping enable signal COIL_VGATE_PWM, thereby disabling all power to the gate driver circuit 39040, heating engine drive circuit 3906 and heater 336. The controller 2105 may then enable vaping at the non-nicotine e-vaping device 500 by again asserting the vaping enable signal COIL_VGATE_PWM to the rail converter circuit 39020.

Similar to the heater activation signal GATE_ON in FIG. 38, the controller 2105 may output the first heater enable signal GATE_ENB having a logic high level to enable power to the heating engine drive circuit 3906 and the heater 336 in response to detecting vaping conditions at the non-nicotine e-vaping device 500. The controller 2105 may output the first heater enable signal GATE_ENB having a logic low level to disable power to the heating engine drive circuit 3906 and the heater 336, thereby performing a heater off operation.

Referring in more detail to the rail converter circuit 39020 in FIG. 39, a capacitor C36 is connected between the voltage source BATT and ground. The capacitor C36 serves as a reservoir for the rail converter circuit 39020.

A first terminal of inductor L1006 is connected to node Node1 between the voltage source BATT and the capacitor C36. The inductor L1006 serves as the main storage element of the rail converter circuit 39020.

A second terminal of the inductor L1006, a drain of a transistor (e.g., an enhancement mode MOSFET) Q1009 and a first terminal of a capacitor C1056 are connected at node Node2. The source of the transistor Q1009 is connected to ground, and the gate of the transistor Q1009 is configured to receive the vaping enable signal COIL_VGATE_PWM from the controller 2105.

In the example shown in FIG. 39, the transistor Q1009 serves as the main switching element of the rail converter circuit 39020.

A resistor R29 is connected between the gate of the transistor Q1009 and ground to act as a pull-down resistor to ensure that transistor Q1009 switches off more reliably and that operation of the heater 336 is prevented when the vaping enable signal COIL_VGATE_PWM is in an indeterminate state.

A second terminal of the capacitor C1056 is connected to a cathode of a Zener diode D1012 and an anode of a Zener diode D1013 at node Node3. The anode of the Zener diode D1012 is connected to ground.

The cathode of the Zener diode D1013 is connected to a terminal of the capacitor C35 and an input of a voltage divider circuit including resistors R1087 and R1088 at node Node4. The other terminal of the capacitor C35 is connected to ground. The voltage at node Node4 is also the output voltage 9V_GATE output from the rail converter circuit 39020.

A resistor R1089 is connected to the output of the voltage divider circuit at node Node5.

In example operation, when the vaping enable signal COIL_VGATE_PWM is asserted and at a logic high level, the transistor Q1009 switches to a low impedance state (ON), thereby allowing current to flow from the voltage source BATT and capacitor C36 to ground through inductor L1006 and transistor Q1009. This stores energy in inductor L1006, with the current increasing linearly over time.

When the vaping enable signal COIL_VGATE_PWM is at a logic low level, the transistor Q1009 switches to a high impedance state (OFF). In this case, the inductor L1006 maintains current flow (decaying linearly), and the voltage at node Node2 rises.

The duty cycle of the vaping enable signal COIL_VGATE_PWM determines the amount of voltage rise for a given load. Accordingly, the vaping enable signal COIL_VGATE_PWM is controlled by the controller 2105 in a closed loop using feedback signal COIL_VGATE_FB output by the voltage divider circuit at node Node5 as feedback. The switching described above occurs at a relatively high rate (e.g., about 2 MHz, however different frequencies may be used depending on the parameters required and element values).

Still referring to the rail converter circuit 39020 in FIG. 39, the capacitor C1056 is an AC coupling capacitor that provides a DC block to remove the DC level. The capacitor C1056 blocks current flow from voltage source BATT through the inductor L1006 and the diode D1013 to the gate driver circuit 39040 when the vaping enable signal COIL_VGATE_PWM is low to save battery life (e.g., when the non-nicotine e-vaping device 500 is in a standby mode). The capacitance of the capacitor C1056 may be chosen to provide a relatively low impedance path at the switching frequency.

The Zener diode D1012 establishes the ground level of the switching signal. Since capacitor C1056 removes the DC level, the voltage at node Node3 may normally be bipolar. In one example, the Zener diode D1012 may clamp the negative half cycle of the signal to about 0.3V below ground.

The capacitor C35 serves as the output reservoir for the rail converter circuit 39020. The Zener diode D1013 blocks current from the capacitor C35 from flowing through capacitor C1056 and transistor Q1009 when the transistor Q1009 is ON.

As the decaying current from inductor L1006 creates a voltage rise at node Node4 between Zener diode D1013 and capacitor C35, current flows into capacitor C35. The capacitor C35 maintains the 9V_GATE voltage while energy is being stored in the inductor L1006.

The voltage divider circuit including resistors R1087 and R1088 reduces the voltage to an acceptable level for measurement at the ADC at the controller 2105. This reduced voltage signal is output as the feedback signal COIL_VGATE_FB.

In the circuit shown in FIG. 39, the feedback signal COIL_VGATE_FB voltage is scaled at about 0.25×, therefore the 9V output voltage is reduced to about 2.25V for input to the ADC at the controller 2105.

The resistor R1089 provides a current limit for an over-voltage fault at the output of the rail converter circuit 39020 (e.g., at node Node4) to protect the ADC at the controller 2105.

The 9V output voltage signal 9V_GATE is output from the rail converter circuit 39020 to the gate driver circuit 39040 to power the gate driver circuit 39040.

Referring now to the gate driver circuit 39040 in more detail, the gate driver circuit 39040 includes, among other things, an integrated gate driver U2003 configured to convert low-current signal(s) from the controller 2105 to high-current signals for controlling switching of the transistors (e.g., MOSFETs) of the heating engine drive circuit 3906. The integrated gate driver U2003 is also configured to translate voltage levels from the controller 2105 to voltage levels required by the transistors of the heating engine drive circuit 3906. In the example embodiment shown in FIG. 39, the integrated gate driver U2003 is a half-bridge driver. However, example embodiments should not be limited to this example.

In more detail, the 9V output voltage from the rail converter circuit 39020 is input to the gate driver circuit 39040 through a filter circuit including resistor R2012 and capacitor C2009. The filter circuit including the resistor R2012 and the capacitor C2009 is connected to the VCC pin (pin 4) of the integrated gate driver U2003 and the anode of Zener diode 52002 at node Node6. The second terminal of the capacitor C2009 is connected to ground. The anode of the Zener diode D2002 is connected to a first terminal of capacitor C2007 and a boost pin BST (pin 1) of the integrated gate driver U2003 at node Node7. A second terminal of the capacitor C2007 is connected to the switching node pin SWN (pin 7) of the integrated gate driver U2003 and the heating engine drive circuit 3906 (e.g., between two MOSFETs) at node Node8. In the example embodiment shown in FIG. 39, the Zener diode D2002 and the capacitor C2007 form part of a boot-strap charge-pump circuit connected between the input voltage pin VCC and the boost pin BST of the integrated gate driver U2003. Because the capacitor C2007 is connected to the 9V input voltage signal 9V_GATE from the rail converter circuit 39020, the capacitor C2007 charges to a voltage almost equal to the voltage signal 9V_GATE through the diode D2002.

Still referring to FIG. 39, a high side gate driver pin DRVH (pin 8), a low side gate driver pin DRVL (pin 5) and an EP pin (pin 9) of the integrated gate driver U2003 are also connected to the heating engine drive circuit 3906.

A resistor R2013 and a capacitor C2010 form a filter circuit connected to the input pin IN (pin 2) of the integrated gate driver U2003. The filter circuit is configured to remove high frequency noise from the second heater enable signal COIL_Z input to the input pin. The second heater enable signal COIL_Z may be a PWM signal from the controller 2105.

A resistor R2014 is connected to the filter circuit and the input pin IN at node Node9. The resistor R2014 is used as a pull-down resistor, such that if the second heater enable signal COIL_Z is floating (or indeterminate), then the input pin IN of the integrated gate driver U2003 is held at a logic low level to prevent activation of the heating engine drive circuit 3906 and the heater 336.

The first heater enable signal GATE_ENB from the controller 2105 is input to the OD pin (pin 3) of the integrated gate driver U2003. A resistor R2016 is connected to the OD pin of the integrated gate driver U2003 as a pull-down resistor, such that if the first heater enable signal GATE_ENB from the controller 2105 is floating (or indeterminate), then the OD pin of the integrated gate driver U2003 is held at a logic low level to prevent activation of the heating engine drive circuit 3906 and the heater 336.

In the example embodiment shown in FIG. 39, the heating engine drive circuit 3906 includes a transistor (e.g., a MOSFET) circuit including transistors (e.g., MOSFETs) 39062 and 39064 connected in series between the voltage source BATT and ground. The gate of the transistor 39064 is connected to the low side gate driver pin DRVL (pin 5) of the integrated gate driver U2003, the drain of the transistor 39064 is connected to the switching node pin SWN (pin 7) of the integrated gate driver U2003 at node Node8, and the source of the transistor 39064 is connected to ground GND.

When the low side gate drive signal output from the low side gate driver pin DRVL is high, the transistor 39064 is in a low impedance state (ON), thereby connecting the node Node8 to ground.

As mentioned above, because the capacitor C2007 is connected to the 9V input voltage signal 9V_GATE from the rail converter circuit 39020, the capacitor C2007 charges to a voltage equal or substantially equal to the 9V input voltage signal 9V_GATE through the diode D2002.

When the low side gate drive signal output from the low side gate driver pin DRVL is low, the transistor 39064 switches to the high impedance state (OFF), and the high side gate driver pin DRVH (pin 8) is connected internally to the boost pin BST within the integrated gate driver U2003. As a result, transistor 39062 is in a low impedance state (ON), thereby connecting the switching node SWN to the voltage source BATT to pull the switching node SWN (Node 8) to the voltage of the voltage source BATT.

In this case, the node Node7 is raised to a boost voltage V(BST) V(9V_GATE)+V(BATT), which allows the gate-source voltage of the transistor 39062 to be the same or substantially the same as the voltage of the 9V input voltage signal 9V_GATE (e.g., V(9V_GATE)) regardless (or independent) of the voltage from the voltage source BATT. As a result, the switching node SWN (Node 8) provides a high current switched signal that may be used to generate a voltage output to the heater 336 that is substantially independent of the voltage output from the battery voltage source BATT.

Figure 41:
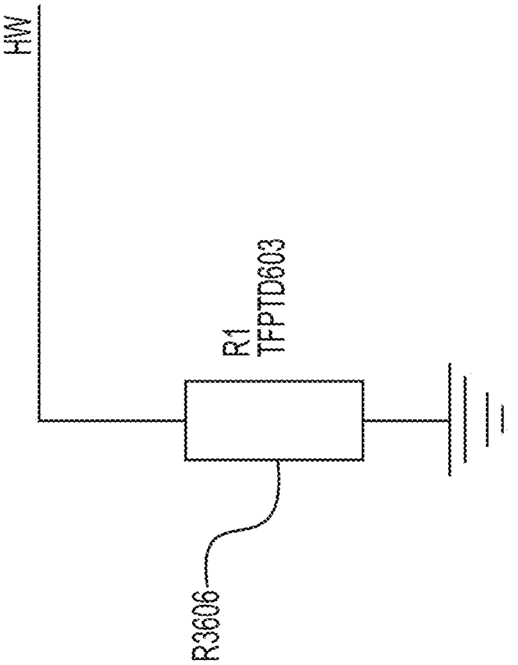
FIG. 41 illustrates a temperature sensing transducer according to another example embodiment.
Figure 40:
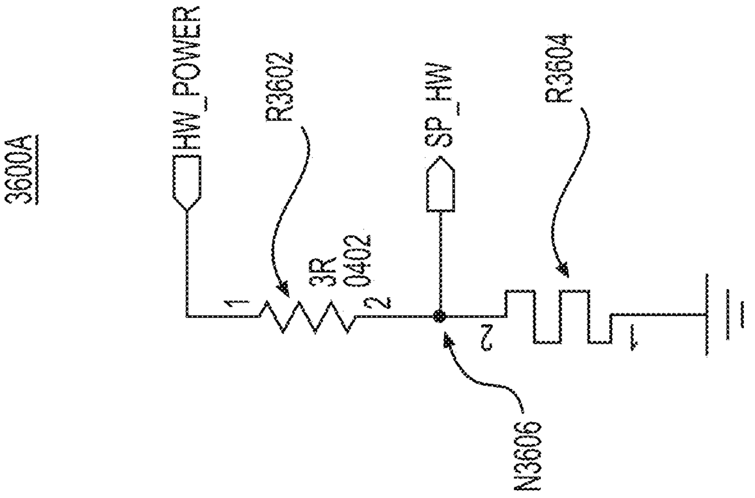
FIG. 40 illustrates a temperature sensing transducer according to an example embodiment.

FIGS. 40 and 41 illustrate example embodiments of temperature sensing transducers included in the pod sensors 2220.

Referring to FIG. 40, the temperature sensing transducer 3600A includes a resistor R3602 and a sensor transducer R3604. In at least one example embodiment the resistor R3602 may have a fixed resistance of about 3 Ohms. The sensor transducer R3604 may be a resistor having a variable resistance that varies with temperature. The resistor R3602 and the sensor transducer R3604 are arranged in a voltage divider circuit so that the voltage across the sensor transducer R3604 (voltage at measurement node N3606) may be output to the pod temperature measurement circuit 21250 for scaling and then use in measuring the temperature of the non-nicotine pod assembly 300 or one or more elements of the non-nicotine pod assembly 300, such as the heater 336.

In example operation, a driver stage 3902A of the pod temperature measurement circuit 21250A (FIG. 36) applies a pod temperature measurement power signal HW_POWER to the temperature sensing transducer 3600A and a measurement stage 3904A of the pod temperature measurement circuit 21250A scales the sensed voltage of the pod sensor signal SP_HW at the measurement node N3606, and outputs the scaled voltage to the controller 2105 as the pod temperature measurement output signal HW_SIGNAL. The controller 2105 (or the fault detection sub-system 2630) may then determines the temperature of the non-nicotine pod assembly 300 or one or more elements of the non-nicotine pod assembly 300 based on the pod temperature measurement output signal HW_SIGNAL.

In at least one example embodiment, the voltage of the pod temperature measurement power signal HW_POWER may be fixed, and thus, the pod temperature measurement circuit 21250A may also calculate the current through resistors R3602 and R3604 because the resistance of the resistor R3602 is a known resistance.

Referring to the example embodiment shown in FIG. 41, the temperature sensing transducer 3600B is similar to the temperature sensing transducer 3600A in FIG. 40, except that, as mentioned above with regard to FIG. 37, the resistor R3602 is omitted from the temperature sensing transducer 3600B and relocated to the driver stage 3902B of the pod temperature measurement circuit 21250B in FIG. 37. By relocating the resistor R3602 to the driver stage 3902B of the pod temperature measurement circuit 21250B, the cost of the non-nicotine pod assembly electrical system 2200 and/or the number of pins required for the interface between the device body 100 and the non-nicotine pod assembly 300 may be reduced. Moreover, the resistance of the sensor transducer R3606 in the example embodiment shown in FIG. 41 may be larger than the resistance of the sensor transducer R3604 in FIG. 40 to reduce current consumption by the temperature sensing transducer 3600B.

Figure 42B:
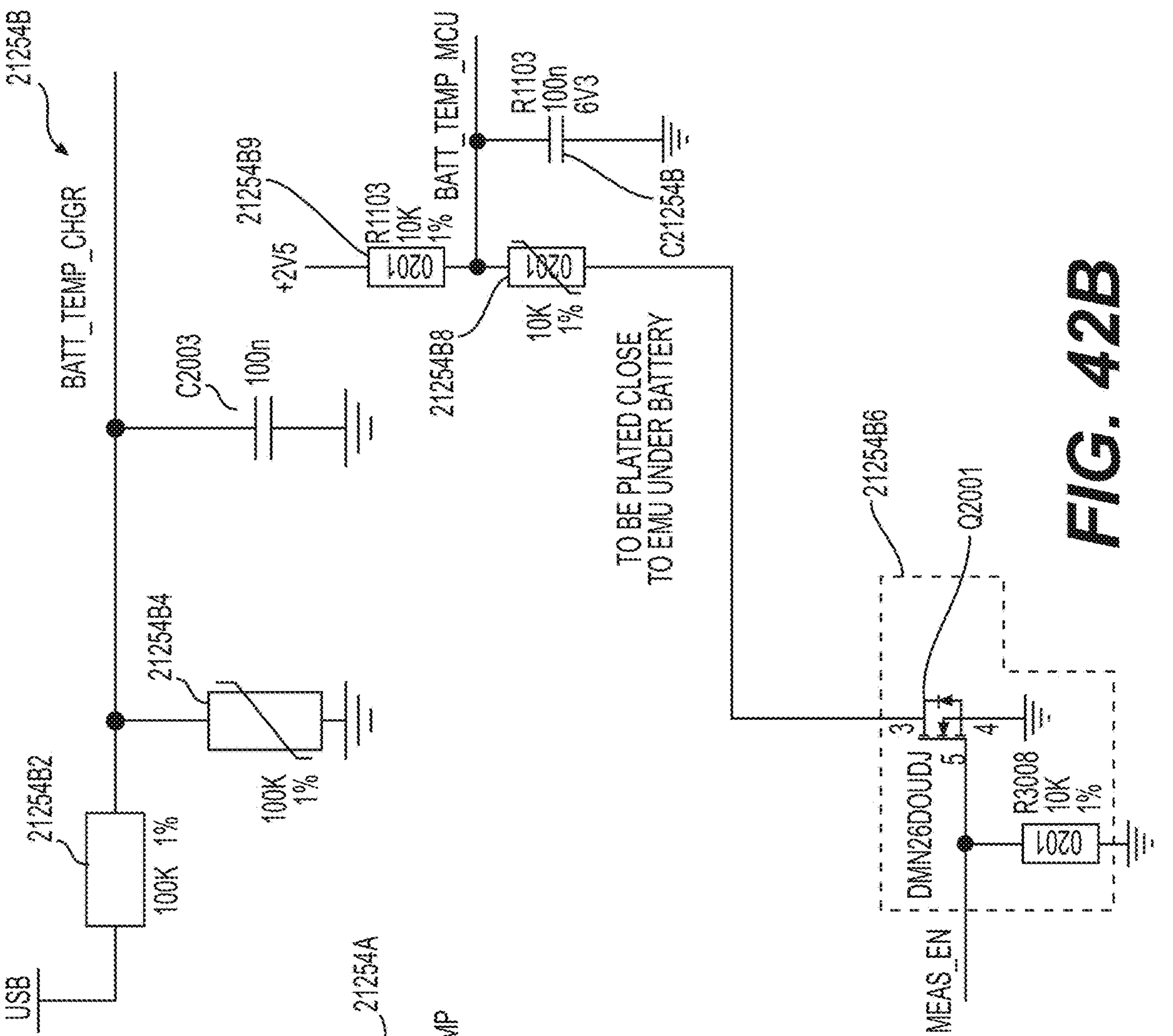
FIG. 42B illustrates a power supply temperature measurement circuit according to another example embodiment.
Figure 42A:
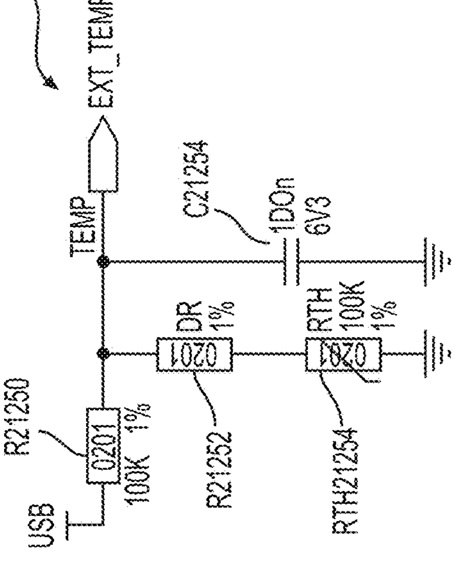
FIG. 42A illustrates a power supply temperature measurement circuit according to an example embodiment.

FIG. 42A illustrates an example embodiment of the power supply temperature measurement circuit 21254.

Referring to FIG. 42A, the power supply temperature measurement circuit 21254A is configured to measure the temperature of the power supply 2110, for example, during charging. The power supply temperature measurement circuit 21254A utilizes a thermistor RTH21254, which is placed relatively close (near) the power supply, to estimate the temperature of the battery. The power supply temperature measurement circuit 21254A outputs the TEMP signal as temperature signal EXT_TEMP to a dedicated charger IC, which may terminate charging, and notify the fault detection sub-system 2630 of the fault, if the temperature signal EXT_TEMP indicates that the temperature of the power supply 2110 exceeds a maximum temperature threshold.

The permitted temperature may be set by changing the ratio of resistors R21250 and R21252 to bias the resistance of the voltage divider circuit including resistors R21250 and R21252. A capacitor C21254 is connected in parallel with resistors R21250, R21252 and thermistor RTH21254.

The power supply temperature measurement circuit 21254A may be powered by a USB voltage through the charger 2132 in order to eliminate any dependency on other system voltages (e.g., the power supply voltage) when charging.

The power supply temperature measurement circuit 21254A may be a dedicated temperature measurement circuit for the charger IC at the charger 2132.

FIG. 42B illustrates another example embodiment of the power supply temperature measurement circuit 21254.

Referring to FIG. 42B, the power supply temperature measurement circuit 21254B is functionally equivalent to the circuit shown in FIG. 42A, but further includes a second power supply temperature sensor circuit configured to output a temperature signal BATT_TEMP_MCU to the controller 2105 for determining whether the temperature of the power supply 2110 is outside its operational limits (e.g., above a threshold maximum or below a threshold minimum), and whether a power supply temperature fault event has occurred.

In more detail, the power supply temperature measurement circuit 21254B includes a first power supply temperature sensor circuit that utilizes a thermistor 21254B4, which is placed relatively close to (near) the power supply 2110, to estimate the temperature of the power supply 2110. The first power supply temperature sensor circuit outputs the temperature signal BATT_TEMP_CHGR to the dedicated charger IC, which may terminate charging, and notify the fault detection sub-system 2630 of the fault, when the temperature of the power supply 2110 exceeds a maximum temperature threshold.

The power supply temperature measurement circuit 21254B further includes a second power supply temperature sensor circuit. The second power supply temperature sensor circuit is similar to the first power supply sensor circuit, except that the second power supply temperature sensor circuit outputs a temperature signal BATT_TEMP_MCU to the controller 2105.

In more detail, the second power supply temperature sensor circuit utilizes a thermistor 21254B8, which is placed relatively close to (near) the power supply 2110, to estimate the temperature of the power supply 2110. The second power supply temperature sensor circuit then outputs the temperature signal BATT_TEMP_MCU indicative of the sensed temperature to the controller 2105. The fault detection sub-system 2630 may determine whether a power supply temperature fault event has occurred at the non-nicotine e-vaping device 500 based on the temperature signal BATT_TEMP_MCU. A capacitor C21254B is connected between ground and a node between resistor 21254B9 and thermistor 21254B8.

The second power supply temperature sensor circuit also includes a temperature measurement control circuit 21254B6 configured to disable the measurement of the temperature of the power supply 2110 and isolate the voltage dividers included therein in a low power mode (e.g., after the auto off operation) to conserve power. As shown in FIG. 42B, the temperature measurement control circuit 21254B6 may include a transistor Q2001 connected between the thermistor 21254B8 and ground. The transistor Q2001 may be selectively enabled and disabled based on a power supply measurement enable signal MEAS_EN from the controller 2105 to selectively enable and disable the second power supply temperature sensor circuit.

Figure 43A:
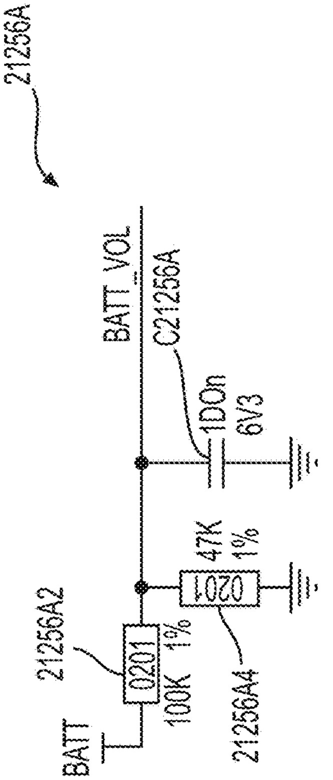
FIG. 43A illustrates a power supply voltage measurement circuit according to an example embodiment.

FIG. 43A illustrates an example embodiment of the power supply voltage measurement circuit 21256.

Referring to FIG. 43A, the power supply voltage measurement circuit 21256A utilizes a voltage divider circuit including resistors 21256A2 and 21256A4 to scale the power supply voltage measurement signal BATT_VOL to match the input range of the ADC in the controller 2105 (e.g., about 1.8V). The controller 2105 may determine the voltage level of the power supply 2110 based on the power supply voltage measurement signal BATT_VOL.

A capacitor C21256A is connected between ground and a node between resistors 21256A2 and 21256A4.

The power supply voltage measurement circuit 21256A may utilize a relatively large total resistance value (e.g., about 147 kΩ) to reduce added drain on the power supply 2110.

The controller 2105 may scale the power supply voltage measurement signal BATT_VOL to represent an actual voltage of the power supply 2110. The fault detection sub-system 2630 may determine that a power supply voltage fault has occurred if the power supply voltage drops below a minimum threshold level (e.g., about ~-3.6V).

Figure 43B:
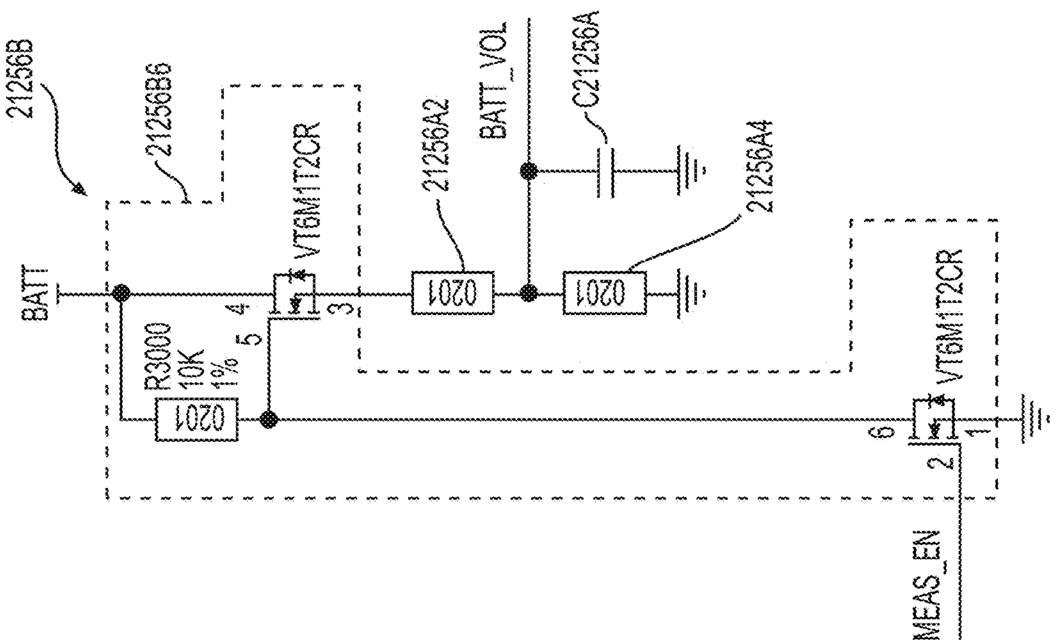
FIG. 43B illustrates a power supply voltage measurement circuit according to an example embodiment.

FIG. 43B illustrates another example embodiment of the power supply voltage measurement circuit 21256. The example embodiment shown in FIG. 43B is similar to the example embodiment shown in FIG. 43A, but further includes a voltage measurement control circuit 21256B6 configured to disable the measurement of the voltage of the power supply 2110 and isolate the voltage dividers included therein in a low power mode to conserve power. As shown in FIG. 43B, the voltage measurement control circuit 21256B6 may include a transistor circuit including transistors Q3001 and Q3002 configured to be selectively enabled and disabled based on the power supply measurement enable signal MEAS_EN to selectively enable and disable the power supply voltage sensor circuit 21256B.

Figure 44A:
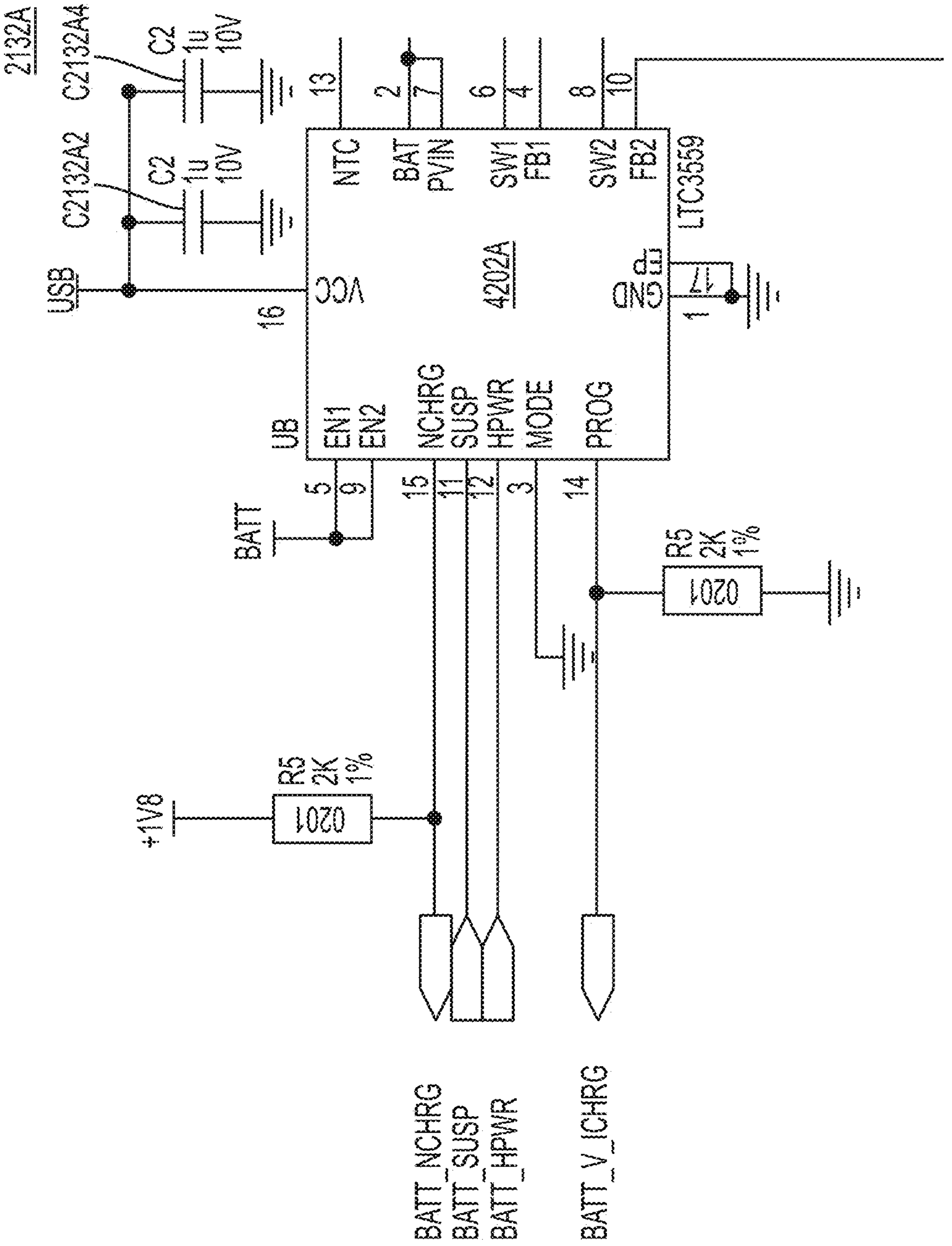
FIG. 44A illustrates a charger according to an example embodiment.

FIG. 44A illustrates an example embodiment of the charger 2132.

Referring to FIG. 44A, the charger 2132A includes a dedicated charging IC 4202A, which provides a plurality of input/outputs (I/O) to manage charging of the power supply 2110. Capacitors C2132A2 and C2132A4 are connected in parallel with one another between the VCC input of the dedicated charging IC 4202A and ground.

The dedicated charging IC 4202A is configured to output a power supply charging signal BATT_NCHRG to the controller 2105. The power supply charging signal BATT_NCHRG may be a PWM modulated output configured to communicate four states: Charging Underway, Charging Complete, Dead Battery or Battery Temperature Out of Range. The fault detection sub-system 2630 may determine whether a fault event has occurred based on the power supply charging signal BATT_NCHRG. In one example, the power supply charging signal BATT_NCHRG having a Charging Complete state may indicate a normal fault event (e.g., charging complete fault event) to the fault detection sub-system 2630, in response to which the fault detection sub-system 2630 may output a normal fault event alert to the auto shutdown decision sub-system 2650. In another example, the power supply charging signal BATT_NCHRG having a Dead Battery state may indicate a hard fault device event (e.g., a power supply fault event) to the fault detection sub-system 2630, in response to which the fault detection sub-system 2630 may output a hard fault device event alert to the auto shutdown decision sub-system 2650. In yet another example, the power supply charging signal BATT_NCHRG having a Battery Temperature Out of Range state may indicate a hard fault device event to the fault detection sub-system 2630, in response to which the fault detection sub-system 2630 may output a hard fault device event alert to the auto shutdown decision sub-system 2650. The dedicated charging IC 4202A may output the power supply charging signal BATT_NCHRG having a Battery Temperature Out of Range in response to receiving the temperature signal BATT_TEMP_CHGR indicating the same from the power supply temperature measurement circuit 21254.

A power supply control signal BATT_SUSP is an example of a device power state signal output by the controller 2105 to the dedicated charging IC 4202A to cause the charger 2132A to perform a charger stop operation thereby suspending charging of the power supply 2110 by the charger 2132A.

The charger 2132A is also configured to output a charging voltage signal BATT_V_ICHRG to the controller 2105. The charging voltage signal BATT_V_ICHRG represents an amount of current currently being supplied to the power supply 2110 by the charger 2132A. Based on the charging voltage signal BATT_V_CHRG, the fault detection sub-system 2630 may monitor the current being supplied to the power supply 2110 by the charger 2132 to determine whether the charging current is outside of a range of values (e.g., less than a minimum threshold or greater than a maximum threshold, each of which may be determined based on empirical data). If the fault detection sub-system 2630 determines that the charging current is outside of the range of values, then the fault detection sub-system 2630 may output a hard fault device event alert to the auto shutdown decision sub-system 2650.

According to at least some example embodiments, a maximum over-current of about 105% of the specified maximum may be utilized as an upper limit of the range of values. In one example, for a 900 mA maximum charging rate expected for the non-nicotine e-vaping device 500, the hard fault device event alert would be output to the auto shutdown decision sub-system 2650 at about 945 mA.

A lower limit of the range values need not necessarily be specified since the charge current will reduce as the battery approaches fully charged.

Figure 44B:
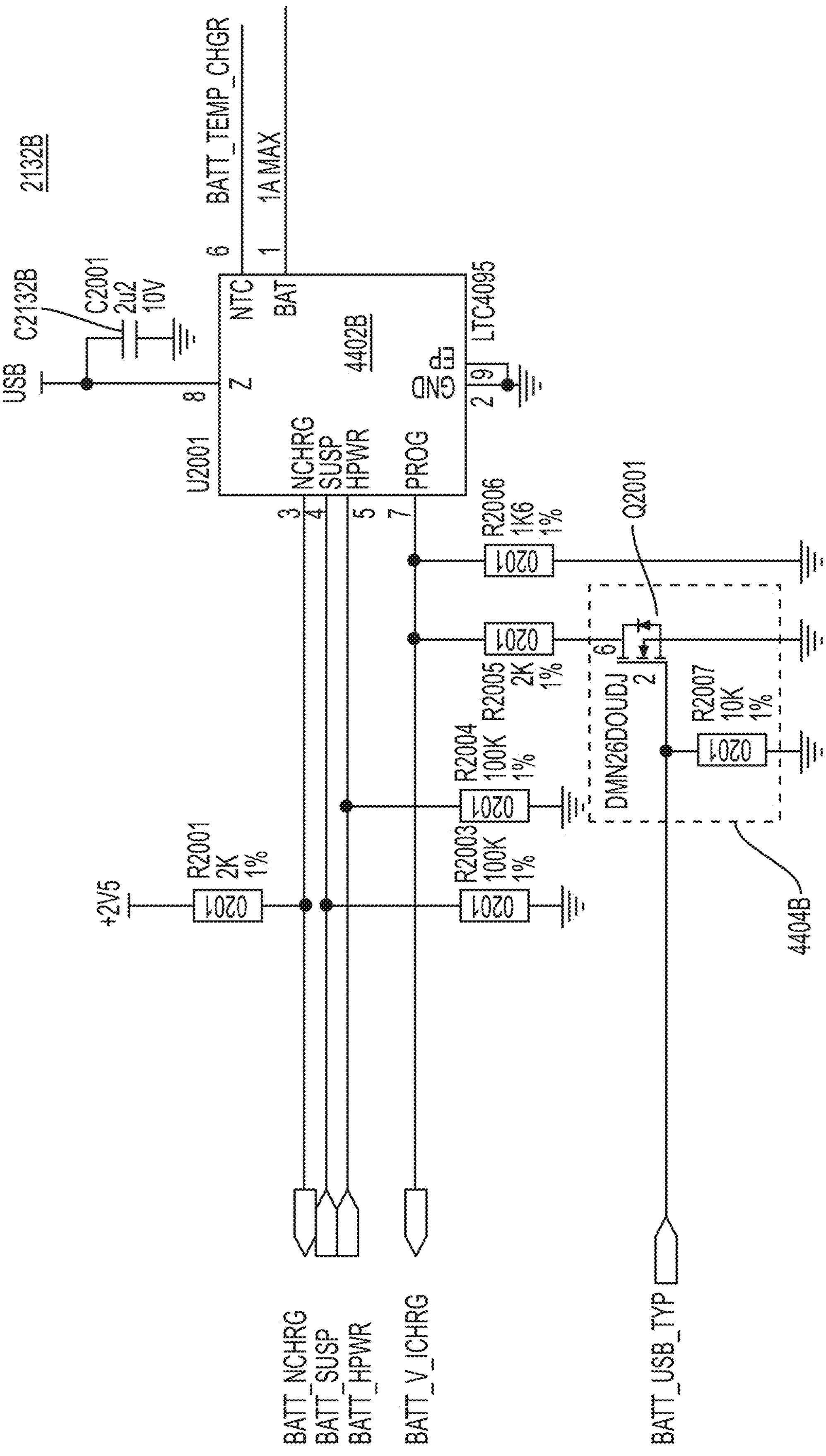
FIG. 44B illustrates a charger according to another example embodiment.

FIG. 44B illustrates another example embodiment of the charger 2132. The charger 2132B is similar to the circuit shown in FIG. 44A, except that a different IC is utilized and the circuit further includes a charge rate selector 4404B. In the example embodiment shown in FIG. 44B, a capacitor 2132B is connected between input IN and ground.

In the example embodiment shown in FIG. 44B, the dedicated charging IC 4402B maintains the same control and monitoring signals (e.g., BATT_NCHRG, BATT_SUSP, BAT_V_ICHRG, etc.) described above with regard to FIG. 44A, but removes the built in voltage regulators from the dedicated charging IC 4202A shown in FIG. 44A.

The charge rate selector 4404B includes a transistor Q2001A, and allows the controller 2105 to select different charge currents using charging current adjustment signal BATT_USB_TYP.

Example embodiments have been disclosed herein, it should be understood that other variations may be possible. Such variations are not to be regarded as a departure from the spirit and scope of the present disclosure, and all such modifications as would be obvious to one skilled in the art are intended to be included within the scope of the following claims.

What is claimed is:

1. A non-nicotine electronic vaping device comprising:

a non-nicotine pod assembly including
- a non-nicotine reservoir to hold non-nicotine pre-vapor formulation, and
- a heater configured to vaporize non-nicotine pre-vapor formulation drawn from the non-nicotine reservoir; and a device body configured to engage with the non-nicotine pod assembly, the device body including a controller configured to
- detect a plurality of types of fault events within the non-nicotine electronic vaping device, the plurality of types of fault events including a soft fault pod event, a hard fault pod event, a soft fault device event, and a hard fault device event,
- perform a first consequent action based on a detected fault event being a soft fault pod event, the first consequent action being a heater off operation that cuts power to the heater to end a current puff event such that the non-nicotine electronic vaping device remains enabled for a next puff event subsequent to the current puff event, and perform a second consequent action based on the detected fault event being a hard fault pod event, the second consequent action being a vaping off operation executed by outputting a vaping shutdown signal having a first logic level to a heating engine control circuit to disable all power to the heater and prevent further vaping until a corrective action is taken, and the hard fault pod event being an abnormal condition within the non-nicotine pod assembly, electrically sense that electrical contacts of the non-nicotine pod assembly have been disconnected from a device electrical connector of the device body, and reset the vaping shutdown signal to a second logic level, in response to the electrical contacts of the non-nicotine pod assembly being disconnected from the device body, wherein the heater off operation and the vaping off operation are different.

2. The non-nicotine electronic vaping device of claim 1, wherein the soft fault pod event is an abnormal condition at the non-nicotine pod assembly, and the soft fault device event and the hard fault device event are abnormal conditions at the device body.

3. The non-nicotine electronic vaping device of claim 1, wherein the device body further comprises:

at least one vaper indicator configured to output an indication that a fault event has occurred.

4. The non-nicotine electronic vaping device of claim 3, wherein the device body further includes a memory; and in response to the hard fault pod event, the controller is configured to disable a vaping function at the non-nicotine electronic vaping device, log an occurrence of the fault event in the memory, and cause the at least one vaper indicator to output the indication that the fault event has occurred.

5. The non-nicotine electronic vaping device of claim 4, wherein the controller is further configured to detect disengaging of the non-nicotine pod assembly from the device body, and disable the vaping function at the non-nicotine electronic vaping device in response to detecting disengaging of the non-nicotine pod assembly from the device body.

6. The non-nicotine electronic vaping device of claim 4, wherein the controller is further configured to determine that a corrective action has not been taken in response to the hard fault pod event, and cause the device body to enter a sleep mode in response to determining that the corrective action has not occurred within a threshold time period.

7. The non-nicotine electronic vaping device of claim 3, wherein the device body further includes a memory; and the controller is configured to perform at least one consequent action based on the detected fault event and a determination that a corrective action has not been taken by initiating an auto off operation in which the non-nicotine electronic vaping device enters a sleep mode, logging an occurrence of the fault event in the memory, and causing the at least one vaper indicator to output the indication that the fault event has occurred.

8. The non-nicotine electronic vaping device of claim 1, wherein the non-nicotine pod assembly includes a memory configured to store a threshold temperature value; and the controller is configured to detect a fault event by obtaining the threshold temperature value from the memory, estimating a temperature of the heater during operation of the non-nicotine electronic vaping device, and detecting the fault event in response to determining that the temperature of the heater is greater than or equal to the threshold temperature value.

9. The non-nicotine electronic vaping device of claim 1, wherein a power supply charging failure is a power supply failure at a charger; and a power stage fault is a presence of current flowing through the heater after vaping conditions are no longer present at the non-nicotine electronic vaping device.

10. The non-nicotine electronic vaping device of claim 1, wherein the heater off operation cuts power to the heater to end a current puff event such that the non-nicotine electronic vaping device remains ready for vaping.

11. The non-nicotine electronic vaping device of claim 1, wherein the vaping off operation disables all energy to the heater to prevent vaping until a corrective action is taken.

* * * * *